US011096955B2

(12) United States Patent
Surace et al.

(10) Patent No.: US 11,096,955 B2
(45) Date of Patent: Aug. 24, 2021

(54) SYNTHETIC PROMOTERS AND USES THEREOF

(71) Applicant: FONDAZIONE TELETHON, Rome (IT)

(72) Inventors: Enrico Maria Surace, Rome (IT); Mariangela Lupo, Rome (IT); Salvatore Botta, Rome (IT); Elena Marrocco, Rome (IT); Nicola De Prisco, Rome (IT)

(73) Assignee: Fondazione Telethon, Rome (IT)

( * ) Notice: Subject to any disclaimer, the term of this patent is extended or adjusted under 35 U.S.C. 154(b) by 101 days.

(21) Appl. No.: 16/075,236

(22) PCT Filed: Feb. 9, 2017

(86) PCT No.: PCT/EP2017/052858
§ 371 (c)(1),
(2) Date: Aug. 3, 2018

(87) PCT Pub. No.: WO2017/137493
PCT Pub. Date: Aug. 17, 2017

(65) Prior Publication Data
US 2019/0038660 A1 Feb. 7, 2019

(30) Foreign Application Priority Data
Feb. 9, 2016 (EP) .................. 16154950

(51) Int. Cl.
C07H 21/02 (2006.01)
A61K 48/00 (2006.01)
A61K 31/7105 (2006.01)
C07K 14/72 (2006.01)
C12N 15/113 (2010.01)
A61P 27/00 (2006.01)
C12N 15/67 (2006.01)
C12N 15/85 (2006.01)
C12N 15/62 (2006.01)
C07K 14/00 (2006.01)

(52) U.S. Cl.
CPC .......... A61K 31/7105 (2013.01); A61P 27/00 (2018.01); C07K 14/00 (2013.01); C07K 14/72 (2013.01); C12N 15/113 (2013.01); C12N 15/625 (2013.01); C12N 15/67 (2013.01); C12N 15/8509 (2013.01); C12N 2830/008 (2013.01)

(58) Field of Classification Search
CPC ..... A61K 2300/00; C12N 9/22; C12N 15/113
See application file for complete search history.

(56) References Cited

FOREIGN PATENT DOCUMENTS

| WO | 2008125846 A2 | 10/2008 | |
| WO | WO 2008/125846 A2 * | 10/2008 | ......... A61K 2300/00 |
| WO | 2015075154 A2 | 5/2015 | |

OTHER PUBLICATIONS

May et al., "In vitro comparison studies of truncated rhodopsin promoter fragments from various species in human cell lines", Clinical and Experimental Ophthalmology, 2003, vol. 31, No. 5, pp. 445-450.
International Search Report and Written Opinion for Corresponding International Application No. PCT/EP2017/052858 (18 Pages) (dated Jun. 26, 2017).

* cited by examiner

Primary Examiner — Amy H Bowman
(74) Attorney, Agent, or Firm — Lucas & Mercanti, LLP

(57) ABSTRACT

The present invention relates to the treatment and/or prevention of a retinal disease by using a polynucleotide promoter wherein the polynucleotide or a variant thereof consists of the sequence (hRHOs-wt; SEQ ID NO. 1)
TCCTCCTAGTGTCACCTTGGCCCCTCTTAGAAGCCAATTAGGCCCTCAG TTTCTGCAGCGGGGATTAATATGATTA<u>TGAACACCCCCAATCTCCCAGA</u>

<u>TGCT</u>GATTCAGCCAGGAGCTTAGGAGGGGGAGGTCACTTTATAAGGGTC

TGGGGGGGTCAGAACCCAGAGTCATCCAGCTGGAGCCCTGAGTGGCTGA

GCTCAGGCCTTCGCAGCATTCTTGGGTGGGAGCAGCCACGGGTCAGCCA

CAAGGGCCACAGCC wherein the fragment TGAACACCCCCAATCTCCCAGATGCT which is the sequence from nucleotide 77 to nucleotide 102 of SEQ ID NO. 1, is substituted. The invention is also directed to the use of relative vector, vector systems, host cells and pharmaceutical compositions.

25 Claims, 8 Drawing Sheets
Specification includes a Sequence Listing.

| | |
|---|---|
| hRHOs-wt | GGGATTAATATGATTATGAACACCCCCAATCTCCCAGATGCTGATTCAGCCAGGAGCTTAGG |
| Prom A | GGGATTAATATGATTATGAACACCCCCAATC-----GATGCTGATTCAGCCAGGAGCTTAGG |
| Prom B | GGGATTAATATGATTATGAACACCCCCAATCTCAACTCGTAGGATTCAGCCAGGAGCTTAGG |
| Prom C | GGGATTAATATGATTATGAACACCCCCACGAGAAACTCTGCTGATTCAGCCAGGAGCTTAGG |
| Prom D | GGGATTAATATGATTAGTCCACACCCCACGAGAAACTCTGCTGATTCAGCCAGGAGCTTAGG |
| Prom E | GGGATTAATATGATTATGAACACATGATATCTCCCAGATGCTGATTCAGCCAGGAGCTTAGG |
| Prom F | GGGATTAATATGATTATGAACA-----CATCTCCCAGATGCTGATTCAGCCAGGAGCTTAGG |
| hRHO-s-ΔZF6 | GGGATTAATATGATTATGAA--------ATCTCCCAGATGCTGATTCAGCCAGGAGCTTAGG |
| Prom G | GGGATTAATATGATTAGTCCACACCCCAATCTCCCAGATGCTGATTCAGCCAGGAGCTTAGG |
| Prom H | GGGATTAATATGATTACGACCGTATCGGGGTTAGGGAGTGCTGATTCAGCCAGGAGCTTAGG |
| Prom I | GGGATTAATATGATTAT**-----CCCCCAATCTCCCAGATGCT**GATTCAGCCAGGAGCTTAGG |
| Prom L | GGGATTAATATGATTAGAGGGATTGGTGCTATGCCAGCTGCTGATTCAGCCAGGAGCTTAGG |

Fig. 1

SYNTHETIC PROMOTERS AND USES THEREOF

CROSS-REFERENCE TO RELATED APPLICATIONS

This application is a 371 of PCT/EP2017/052858, filed Feb. 9, 2017, which claims the benefit of European Patent Application No. 16154950.6, filed Feb. 9, 2016.

TECHNICAL FIELD

The present invention relates to the treatment and/or prevention of a pathology or disease characterized by a retinal degeneration by using a polynucleotide promoter wherein said polynucleotide consists of the sequence

TCCTCCTAGTGTCACCTTGGCCCCTCTTAGAAGCCAATTAGGCCCTCAGT

TTCTGCAGCGGGGATTAATATGATTA<u>TGAACACCCCCAATCTCCCAGATG</u>

<u>CT</u>GATTCAGCCAGGAGCTTAGGAGGGGAGGTCACTTTATAAGGGTCTGG

GGGGGTCAGAACCCAGAGTCATCCAGCTGGAGCCCTGAGTGGCTGAGCTC

AGGCCTTCGCAGCATTCTTGGGTGGGAGCAGCCACGGGTCAGCCACAAGG

GCCACAGCC (hRHOs-wt; SEQ ID NO. 1)

wherein the fragment

<u>TGAACACCCCCAATCTCCCAGATGCT</u> (sequence from nucleotide 77 to nucleotide 102 of SEQ. ID NO. 1)

is substituted, to the use of relative vector, vector systems, host cells and pharmaceutical compositions.

BACKGROUND ART

A wide variety of eye diseases causes visual impairment, including macular degeneration, diabetic retinopathies, inherited retinal degeneration disorders such as retinitis pigmentosa, glaucoma, retinal detachment or injury and retinopathies (including those that are inherited, induced by surgery, trauma, a toxic compound or an agent).

A structure in the eye particularly affected by disease is the retina, found at the back of the eye, which is a specialized light-sensitive tissue that contains photoreceptor cells (rods and cones) and neurons connected to a neural network for the processing of visual information. More specifically, the retina is a layered structure composed of six neuronal and one glial cell type, which are organized in three cellular layers: the ganglion cell layer, comprising retinal ganglion (RGC) and displaced amacrine cells, the inner nuclear layer (INL), which contains bipolar, horizontal and amacrine interneurons and Müller glial cells, and the outer nuclear layer (ONL), where rod and cone photoreceptors are located. Rod and cone photoreceptors both have the same basic structure. Closest to the visual field (and farthest from the brain) is the axon terminal. Farther back is the cell body, which contains the cell's organelles. Farther back still is the inner segment (IS), a specialized part of the cell full of mitochondria. Finally, closest to the brain (and farthest from the field of view) is the outer segment (OS), the part of the photoreceptor that absorbs light. The retina is immediately adjacent to the retinal pigment epithelium (RPE), a pigmented cell layer that nourishes retinal visual cells, and is firmly attached to the underlying choroid and overlying retinal visual cells.

Inherited retinal dystrophies (IRDs) represent one of the most frequent causes of genetic blindness in the western world. The primary condition that underlies this group of diseases is the degeneration of photoreceptors, i.e., the cells that convert the light information into chemical and electrical signals that are then transmitted to the brain through the visual circuits. Rods represent about 95% of photoreceptor cells in the human retina and are responsible for sensing contrast, brightness and motion, whereas fine resolution, spatial resolution and color vision are perceived by cones.

IRDs can be subdivided into different groups of diseases, namely Retinitis Pigmentosa (RP), Leber Congenital Amaurosis (LCA), cone-rod dystrophies and cone dystrophies.

RP is the most frequent form of inherited retinal dystrophy with an approximate frequency of about 1 in 4,000 individuals. At its clinical onset, RP is characterized by night blindness and progressive degeneration of photoreceptors accompanied by bone spicule-like pigmentary deposits and a reduced or absent electroretinogram (ERG). RP can be either isolated or syndromic, i.e., associated with extraocular manifestations such as in Usher syndrome or in Bardet-Biedle syndrome. From a genetic point of view, RP is highly heterogeneous, with autosomal dominant, autosomal recessive and X-linked patterns of inheritance. A significant percentage of RP patients, however, are apparently sporadic. To date, around 50 causative genes/loci have been found to be responsible for non-syndromic forms of RP and over 25 for syndromic RPs (RETnet web site: http://www.sph.uth.tmc.edu/RetNet/).

Retinitis pigmentosa (RP), which results in the destruction of photoreceptor cells, the retinal pigmented epithelium (RPE) and the choroid, typifies inherited retinal degenerations.

Autosomal dominant retinitis pigmentosa (ADRP) is the most genetically heterogeneous inherited disease in humans. Dominant forms of retinitis pigmentosa include those that are molecularly owed to gain of function mutation but either those due to aplo-insufficiency or dominant negative effect. This genetic heterogeneity is associated with differences in rate and extent of the degeneration.

Accounting for 30%-40% of all cases of retinitis pigmentosa, autosomal dominant retinitis pigmentosa (ADRP) is the consequence of mutations in more than twenty known genes (Table 1) (Rossmiller et al. Molecular Vision 2012; 18:2479-2496). Approximately 30% of ADRP arises from mutations in the rhodopsin gene.

TABLE 1

Known gene causing ADRP and associated proteins names.
References are at RetNet: https://sph.uth.edu/retnet/.

| Protein | Disease Gene |
|---|---|
| Bestrophin-1 | BEST1 |
| Carbonic anhydrase IV | CA4, RP17 |
| Cone-Rod Homeobox | CRX |
| Fascin homolog 2 | FSCN2, RP30 |
| Guanylate cyclase activator 1B | GUCA1B, RP48 |
| Inosine monophosphate dehydrogenase 1 | IMPDH1, RP10 |
| kelch-like protein 7 | KLHL7, RP42 |
| Nuclear receptor subfamily 2 group E member 3 | NR2E3 |
| Neural retina leucine zipper | NRL, RP27 |
| OSBP-related protein 1 | ORP1, DCDC4A, RP1 |
| pre-mRNA processing factor 3 | PRPF3, RP18 |

TABLE 1-continued

Known gene causing ADRP and associated proteins names.
References are at RetNet: https://sph.uth.edu/retnet/.

| Protein | Disease Gene |
| --- | --- |
| pre-mRNA processing factor 31 homolog | PRPF31 |
| pre-mRNA processing factor 6 | PRPF6, rp60 |
| pre-mRNA processing factor 8 | PRPF8 |
| Peripherin 2 | PRPH2, RDS, RP7 |
| Rhodopsin | RHO |
| Retinal outer segment membrane protein 1 | ROM1 |
| Retinitis pigmentosa 1 protein | RP1, L1 |
| Unknown | RP63 |
| Retinitis pigmentosa 9 protein | RP9 |
| Retinal pigment epithelium-specific protein | RPE65, RP20 |
| Semiphorin | SEMA4A, RP35 |
| Proto-oncogene tyrosine-protein kinase MER | MERTK, RP33 |
| Topoisomerase I-binding arginine/serine-rich protein | TOPORS |
| hexokinase 1 | HK1 |
| pre-mRNA processing factor 4 | PRPF4 |
| retinol dehydrogenase 12 | RDH12, LCA13, RP53 |
| small nuclear ribonucleoprotein 200 kDa (U5) | SNRNP200, ASCC3L1, BRR2, HECIC2, RP33 |

Currently, there are no effective treatments for RP, although gene therapy approaches are promising for treating blinding diseases.

LCA has a prevalence of about 2-3 in 100,000 individuals and is characterized by a severe visual impairment that starts in the first months/years of life. LCA has retinal, ocular as well as extraocular features, and occasionally systemic associations. LCA is inherited as an autosomal recessive trait in the large majority of patients, while autosomal dominant inheritance has been described only in a limited number of cases. LCA is genetically heterogeneous and, to date, mutations have been identified in 15 different genes: GUCY2D (locus name: LCA1), RPE65 (LCA2), SPATA7 (LCA3), AIPL1 (LCA4), LCA5 (LCA5), RPGRIP1 (LCA6), CRX (LCA7), CRB1 (LCA8), CEP290 (LCA10), IMPDH1 (LCA11), RD3 (LCA12), NMNAT1 (LCA9), LRAT (LCA14), TULP1 (LCA15), and RDH12 (LCA13). The diagnosis of LCA is established by clinical findings. Molecular genetic testing is clinically available for the 15 genes currently known to be associated with LCA. Collectively, mutations in these genes are estimated to account for approximately 40%-50% of all LCA cases, depending on the survey.

Cone-rod dystrophies (CRDs) have a prevalence of 1/40,000 individuals and are characterized by retinal pigment deposits visible upon fundus examination, predominantly localized to the macular region. In contrast to typical RP, which is characterized by primary loss in rod photoreceptors, later followed by the secondary loss in cone photoreceptors, CRDs reflect the opposite sequence of events. CRD is characterized by a primary cone involvement, or, sometimes, by concomitant loss of both cones and rods that explains the predominant symptoms of CRDs: decreased visual acuity, color vision defects, photo-aversion and decreased sensitivity in the central visual field, later followed by progressive loss in peripheral vision and night blindness. Mutations in at least 20 different genes have been associated with CRD (RETnet web site: http://www.sph.uth.tmc.edu/RetNet/).

Cone dystrophies (CD) are conditions in which cone photoreceptors display a selective dysfunction that does not extend to rods. They are characterized by visual deficit, abnormalities of color vision, visual field loss, and a variable degree of nystagmus and photophobia. In CDs, cone function is absent or severely impaired on electroretinography (ERG) and psychophysical testing. Similar to the other forms of inherited retinal dystrophies, CDs are heterogeneous conditions that can be caused by mutations in at least 10 different genes (RETnet web site: http://www.sph.uth.tmc.edu/RetNet/).

As also mentioned above, IRDs are due to the degeneration and subsequent death of photoreceptor cells, primarily rods in the case of RP and LCA and primarily cones in the case of CRDs and CDs. Of interest, in RP and in most forms of LCA, rod degeneration is followed by a secondary degeneration of cones. The vast majority of genes responsible for IRDs are expressed predominantly in photoreceptors (either rods or cones). Some IRD genes are prevalently expressed in the retinal pigment epithelium. However, also in the latter case, the main consequence that derives from the dysfunction of these genes is a damage of photoreceptor function, which then translates into photoreceptor degeneration and death. For most forms of the above mentioned diseases an effective therapy is currently unavailable. Gene therapy typically includes viral delivery of vectors carrying one or more transgene(s), whose expression is driven by cell type specific promoter.

In general, transgenes are transfected into the target cells, cell populations or tissues, as DNA constructs in the context of an expression cassette to allow transcription of the transgene. The DNA construct is recognized by the cellular transcription machinery in a process that involves the activity of many trans-acting transcription factors (TF) at cis-regulatory elements including enhancers, silencers, insulators and promoters (herein globally referred to as "promoters"). Promoters comprise short regions of noncoding DNA that contain binding sites for transcriptional activators and repressors, which can act in a combinatorial manner to dictate the spatial, temporal and quantitative levels of the gene whose expression they control.

A promoter is thus a sequence of DNA that can initiate and regulate the transcription of a gene or functional transcripts (small RNAs for instance).

In a cell, a promoter may relate to a genomic region located upstream of a structural gene and may function in the transcription of said structural gene, for example, into mRNA. It may be activated by binding of general transcription factors, and it may include base sequences such as a TATA box and/or CAT box which may assist to regulate gene expression.

Gene promoters are involved in every level of regulation of gene expression, serving as the determinant in gene transcription by integrating the influences of the DNA sequence, transcription factor binding and epigenetic features.

Cell-specific diversity is generated by regulatory combinatorial properties contained in genomic regulatory regions, promoters and/or fragments thereof (herein globally referred to as "promoters"), eventually modulating genes sets.

The promoters may determine the strength of e.g. transgene expression which is encoded by a plasmid vector, as well as in which cell type(s) said transgene will be expressed.

According to what occurs endogenously, spatial and regional expression of a transgene in a cell, for example by means of expression vectors, is strictly regulated by the promoter under which the transgene is cloned. Promoters also regulate the level of expression of a transgene. The most common promoters used for driving heterologous gene expression in mammalian cells are the human and mouse cytomegalovirus (CMV) major immediate early promoter. It has proved robust in several cell types, conferring strong expression.

Recently, eukaryotic promoters are also being used, instead of viral promoters, in view of several advantages, such as long-term expression in vivo, cell specificity and hence safety to gene transfer protocols by minimizing ectopic transgene expression through 'transcriptional targeting', avoidance of the induction of an immune response to otherwise immunogenic transgenes (see Papadakis et al. 2004).

One of the main drawbacks of the use of endogenous eukaryotic promoters for transgene expression is their size, which may hamper their use in viral vectors, in particular in those of reduced capacity, such as Adeno-Associated Vectors (AAVs), or in multicistronic vectors. Furthermore, eukaryotic promoter are generally weak, in terms of downstream genes expression intensity.

Eukaryotic gene expression is highly complex, being controlled by a complex machinery of cis- and trans-acting regulatory elements. It thus requires a precise coordination of many different factors. Most cellular promoters suffer from a lack of extensive functional characterization, which makes their use uneasy.

Eukaryotic promoters are usually located upstream of their transcribed sequence: the core promoter immediately surrounds the transcription start site (TSS) which is sufficient to be recognized by the transcription machinery and serves as the point of transcriptional initiation. The proximal promoter comprises the region upstream of the core promoter, the TSS and other sequence features required for transcriptional regulation.

Transcription factors act sequence-specific by binding to regulatory motifs in the promoter and enhancer sequence, thereby activating chromatin and histone modifying enzymes that alter nucleosome structure and its position which finally allows initiation of transcription.

A key requirement for successful gene therapy is accurate targeting of the construct or vector bearing the transgene to the cells in need of therapy. Such targeting is affected by a number of different factors including delivery of the gene therapy vector to the correct anatomical location, the cellular tropism of the viral vector and the promoters used to drive expression of the transgene (Corbo, 2008) at adequate expression levels, in the desired cell type and/or at the right time.

Therefore, isolation or generation of an appropriate promoter is a crucial step in the process of optimizing expression cassettes to improve transgene expression in vivo.

Optimization of transgene expression in vivo or ex vivo thus requires provision of optimized promoters, exhibiting regulated activity for expression of transgenes in the target cells.

In particular, the availability of promoters with differential strength (promoter activity) to regulate expression of a transgene is highly desirable, in particular in vectors for gene therapy. In the gene therapy field, it may be required to achieve high transduction efficiency; however, the use of a vector at high doses may lead to reduction in cell specificity, increased toxicity, etc. Therefore, the provision of an expression cassette with reduced expression strength and high cell type specificity may be highly desirable when willing to use high vector doses. Conversely, high and specific expression of a transgene may be needed in other conditions.

In gene therapy of retinal-specific disorders, gene modulation by the use of synthetic promoters, which warrant photoreceptor-specific expression, preferably rod-specific expression, with differential strength, is highly desirable.

Improving knowledge of the functional architecture of cell type specific promoters is an essential step towards rational design of synthetic promoters that drive a desired pattern or level of expression within photoreceptors or other retinal cell types, permitting to customize gene therapy vectors depending e.g. on the particular mutation to be treated or the stage of disease.

In a previous study, described in WO2015075154, the inventors generated constructs including a short human rhodopsin (RHO) proximal promoter of 259 bp (164 bp from the TSS and the 95 bp of the 5' UTR; hRHOs wt; SEQ ID No 1) and showed that the sole short proximal promoter of RHO was sufficient to achieve suitable expression of the downstream transgene.

SUMMARY OF THE INVENTION

Surprisingly, the inventors have found that promoters consisting in short RHO proximal promoters bearing mutations and/or deletions within a specific portion of the wild-type sequence, can be successfully used for gene therapy of retinal diseases.

The promoters of the invention share structural and functional features. All of the promoters of the inventions are useful for the treatment of retinal diseases, all derive from the wild-type RHO promoter, all modulate RHO promoter activity.

The modified RHO proximal promoters of the present invention are retina-specific promoters, in particular rod-specific promoters, with weaker or stronger activity on the expression of the downstream transgene, compared to the wild-type RHO proximal promoter (hRHO-s wt). This characteristic makes the promoters of the invention advantageous when cloned within vectors for gene therapy, in the aim of fine tuning a transgene expression in the retina, in particular in the rods.

The promoters of the invention address the need for optimized expression cassettes for gene therapy of eye diseases, preferably retinal diseases such as retinal dystrophy, in particular for the gene therapy of inherited retinal dystrophy, preferably of retinitis pigmentosa.

The promoters of the invention further address a need in the art for retinal cells specific promoter to develop systems for the study of neurodegenerative disorders, vision restoration, drug discovery, tumor therapies and diagnosis of disorders. Preferably the eye disease is a rod-specific disorder.

Moreover, the invention provides a set of promoters having differential strength (i.e. promoters having weaker or stronger promoter activity compared to the wild-type promoter), that can be advantageously used in single or multiple independent expression cassettes vectors (including multicistronic vectors, which allow multiple proteins expression from a single transcript), since promoters of different expression cassettes may differentially express different polynucleotides. Inventors thus surprisingly found that the promoters of the invention can address several needs in the field of gene therapy, such as the provision of cell-specificity of transgene expression, providing a novel tool for regulating intensity of transgenes expression, different from usual regulation based on the dose of gene therapy agent administered.

In a first embodiment, the invention provides a polynucleotide promoter or a variant thereof for use in a gene therapy method for the treatment and/or prevention of a retinal disease wherein said polynucleotide consists of the sequence

TCCTCCTAGTGTCACCTTGGCCCCTCTTAGAAGCCAATTAGGCCCTCAGT

TTCTGCAGCGGGGATTAATATGATTA<u>TGAACACCCCCAATCTCCCAGATG</u>

<u>CT</u>GATTCAGCCAGGAGCTTAGGAGGGGAGGTCACTTTATAAGGGTCTGG

GGGGGTCAGAACCCAGAGTCATCCAGCTGGAGCCCTGAGTGGCTGAGCTC

AGGCCTTCGCAGCATTCTTGGGTGGGAGCAGCCACGGGTCAGCCACAAGG

GCCACAGCC (hRHOs-wt; SEQ ID NO. 1)

wherein the fragment TGAACACCCCCAATCTCCCA-GATGCT (sequence from nucleotide 77 to nucleotide 102 of SEQ ID NO. 1) is substituted with a sequence selected from the group consisting of:

(SEQ ID NO. 12)

a) TGAAATCTCCCAGATGCT (hRHO-s-ΔZF6)

(SEQ ID NO. 2)

b) TGAACACCCCCAATCGATGCT (Prom A)

(SEQ ID NO. 3)

c) TGAACACCCCCAATCTCAACTCGTAG (Prom B)

(SEQ ID NO. 4)

d) TGAACACCCCCACGAGAAACTCTGCT (Prom C)

(SEQ ID NO. 5)

e) GTCCACACCCCACGAGAAACTCTGCT (Prom D)

(SEQ ID NO. 6)

f) TGAACACATGATATCTCCCAGATGCT (Prom E)

(SEQ ID NO. 7)

g) TGAACACATCTCCCAGATGCT (Prom F)

(SEQ ID NO. 8)

h) GTCCACACCCCAATCTCCCAGATGCT (Prom G)

(SEQ ID NO. 9)

i) CGACCGTATCGGGGTTAGGGAGTGCT (Prom H)

(SEQ ID NO. 10)

j) TCCCCCAATCTCCCAGATGCT (Prom I)

(SEQ ID NO. 11)

k) GAGGGATTGGTGCTATGCCAGCTGCT (Prom L)

and
l) a sequence having an identity of at least 90% (preferably 92%, 95%, 97% or 99%) with anyone sequence selected from the group consisting of SEQ ID NO. 2 to 12.

and wherein the variant has at least 70% identity with any of SEQ ID NO 13 to 23. The variant comprises respectively SEQ ID NO. 2 to 12 or comprises a sequence having an identity of at least 90% (preferably 92%, 95%, 97% or 99%) with anyone sequence selected from the group consisting of SEQ ID NO. 2 to 12.

The identity with SEQ ID NO. 13 to 23 refer to the identity with a sequence not including the substituted sequence (SEQ ID No. 2 to 12).

Preferably the variant has at least 75%, 80%, 85%, 90%, 95%, 99% identity with any of SEQ ID NO 13 to 23 and comprises respectively SEQ ID NO. 2 to 12 or comprises a sequence having an identity of at least 90% (preferably 92%, 95%, 97% or 99%) with anyone sequence selected from the group consisting of SEQ ID NO. 2 to 12.

The variant is a functional variant of the polypeptide that maintains the promoter activity of the polypeptide.

Preferably said promoter or a variant thereof has a promoter activity at least 40% higher or at least 25% lower than the wild-type promoter of SEQ ID No. 1.

Preferably the retinal disease is characterized by a retinal degeneration, preferably the retinal disease is inherited.

Preferably the fragment TGAACACCCC-CAATCTCCCAGATGCT (sequence from nucleotide 77 to nucleotide 102 of SEQ ID NO. 1) is substituted with a sequence selected from the group consisting of:

a) (hRHO-s-ΔZF6)

(SEQ ID NO. 12)

TGAAATCTCCCAGATGCT or
b) a sequence having an identity of at least 90% (preferably 92%, 95%, 97% or 99%) with sequence SEQ ID NO. 12.

The invention also provides a polynucleotide promoter or a variant thereof consisting of the sequence (SEQ ID No. 1)

TCCTCCTAGTGTCACCTTGGCCCCTCTTAGAAGCCAATTAGGCCCTCAGT

TTCTGCAGCGGGGATTAATATGATTA<u>TGAACACCCCCAATCTCCCAGATG</u>

<u>CT</u>GATTCAGCCAGGAGCTTAGGAGGGGAGGTCACTTTATAAGGGTCTGG

GGGGGTCAGAACCCAGAGTCATCCAGCTGGAGCCCTGAGTGGCTGAGCTC

AGGCCTTCGCAGCATTCTTGGGTGGGAGCAGCCACGGGTCAGCCACAAGG

GCCACAGCC wherein the fragment TGAACACCCCCAATCTCCCA-GATGCT (sequence from nucleotide 77 to nucleotide 102 of SEQ ID NO. 1) is substituted with a sequence selected from the group consisting of:

a) (Prom A)

(SEQ ID NO. 2)

TGAACACCCCCAATCGATGCT b) (Prom B)

(SEQ ID NO. 3)

TGAACACCCCCAATCTCAACTCGTAG c) (Prom C)

(SEQ ID NO. 4)

TGAACACCCCCACGAGAAACTCTGCT d) (Prom D)

(SEQ ID NO. 5)

GTCCACACCCCACGAGAAACTCTGCT e) (Prom E)

(SEQ ID NO. 6)

TGAACACATGATATCTCCCAGATGCT f) (Prom F)

(SEQ ID NO. 7)

TGAACACATCTCCCAGATGCT g) (Prom G)

(SEQ ID NO. 8)

GTCCACACCCCAATCTCCCAGATGCT h) (Prom H)

(SEQ ID NO. 9)

CGACCGTATCGGGGTTAGGGAGTGCT i) (Prom I)
(SEQ ID NO. 10)
TCCCCCAATCTCCCAGATGCT j) (Prom L)
(SEQ ID NO. 11)
GAGGGATTGGTGCTATGCCAGCTGCT k) a sequence having an identity of at least 90% (preferably 92%, 95%, 97% or 99%) with anyone sequence selected from the group consisting of SEQ ID NO. 2 to 11, and wherein the variant has at least 70% identity with any of SEQ ID NO 13 to 22. The variant comprises respectively SEQ ID NO. 2 to 11 or comprises a sequence having an identity of at least 90% (preferably 92%, 95%, 97% or 99%) with anyone sequence selected from the group consisting of SEQ ID NO. 2 to 12.

Preferably the variant has at least 75%, 80%, 85%, 90%, 95%, 99% identity with any of SEQ ID NO 13 to 22 and comprises respectively SEQ ID NO. 2 to 11 or comprises a sequence having an identity of at least 90% (preferably 92%, 95%, 97% or 99%) with anyone sequence selected from the group consisting of SEQ ID NO. 2 to 11.

The variant is a functional variant of the polypeptide that maintains the promoter activity of the polypeptide.

Preferably the fragment is substituted with a sequence selected from the group consisting of:

a) (Prom A)
(SEQ ID NO. 2)
TGAACACCCCCAATCGATGCT b) (Prom B)
(SEQ ID NO. 3)
TGAACACCCCCAATCTCAACTCGTAG c) (Prom C)
(SEQ ID NO. 4)
TGAACACCCCCACGAGAAACTCTGCT d) (Prom D)
(SEQ ID NO. 5)
GTCCACACCCCACGAGAAACTCTGCT e) (Prom E)
(SEQ ID NO. 6)
TGAACACATGATATCTCCCAGATGCT f) (Prom F)
(SEQ ID NO. 7)
TGAACACATCTCCCAGATGCT g) (Prom G)
(SEQ ID NO. 8)
GTCCACACCCCAATCTCCCAGATGCT h) a sequence having an identity of at least 90% (preferably 92%, 95%, 97% or 99%) with anyone sequence selected from the group consisting of SEQ ID NO. 2 to 8 and wherein said polynucleotide or a variant thereof has a promoter activity weaker than SEQ ID No. 1.

More preferably the fragment is substituted with a sequence selected from the group consisting of:

i) (Prom H)
(SEQ ID NO. 9)
CGACCGTATCGGGGTTAGGGAGTGCT j) (Prom I)
(SEQ ID NO. 10)
TCCCCCAATCTCCCAGATGCT k) (Prom L)
(SEQ ID NO. 11)
GAGGGATTGGTGCTATGCCAGCTGCT l) a sequence having an identity of at least 90% (preferably 92%, 95%, 97% or 99%) with anyone sequence selected from the group consisting of SEQ ID NO. 9 to 11 and wherein said polynucleotide or a variant thereof has a promoter activity stronger than SEQ ID No. 1.

Preferably said polynucleotide or a variant thereof shows a promoter activity in retina cells, preferably in photoreceptors, more preferably in rods.

The invention also provides a vector comprising the polynucleotide or a variant thereof as defined above. Preferably the vector is for use in the treatment and/or prevention of a retinal disease.

The invention also provides a vector comprising a first expression cassette comprising the polynucleotide or a variant thereof as defined above and a first transgene under the control of said polynucleotide.

Preferably said first transgene encodes for a transcriptional repressor. Preferably said transcriptional repressor is selected from the group consisting of: an antisense oligonucleotide, a siRNA, a shRNA or a miRNA, targeting a RHO transcript; an artificial transcription factor (ATF) comprising a DNA Binding domain coupled to one or more effector domains, targeting a sequence of the hRHO promoter; an isolated DNA Binding domain (DNA binding domain or DBD), targeting a sequence of the hRHO promoter.

Preferably the vector comprises at least one further expression cassette, said at least one further expression cassette comprises a further promoter and a further transgene under control of said further promoter, preferably wherein said further promoter is a polynucleotide as defined above and it is the same or it is different from the polynucleotide of the first expression cassette.

Preferably the further transgene is a nucleotide sequence encoding a protein able to correct a retinal disease.

Still preferably the further promoter is a retina specific promoter, preferably a rod-specific promoter, preferably the rhodopsin kinase (RHOK) or the GNAT1 promoter, more preferably wherein the rod-specific promoter is GNAT1 promoter of sequence SEQ ID NO. 52.

Yet preferably the further transgene is the coding sequence of a gene selected from the group consisting of: GUCY2D (locus name: LCA1), RPE65 (LCA2), SPATA7 (LCA3), AIPL1 (LCA4), LCA5 (LCA5), RPGRIP1 (LCA6), CRX (LCA7), CRB1 (LCA8), CEP290 (LCA10), IMPDH1 (LCA11), RD3 (LCA12), NMNAT1 (LCA9), LRAT (LCA14), TULP1 (LCA15), and RDH12 (LCA13), BEST1, CA4, RP17, CRX, FSCN2, RP30, GUCA1B, RP48, IMPDH1, RP10, KLHL7, RP42, NR2E3, NRL, RP27, ORP1, DCDC4A, RP1, PRPF3, RP18, PRPF31, PRPF6, rp60, PRPF8, PRPH2, RDS, RP7, RHO, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2, RP33, preferably wherein the coding sequence is the coding sequence of human RHO (SEQ ID NO 49).

Still preferably the first expression cassette comprises SEQ ID No. 23 and SEQ ID No. 24. Preferably the vector has sequence SEQ ID NO. 32 or has a sequence having an identity of at least 70% with SEQ ID NO. 32, or at least 75%, 80%, 85%, 90%, 95%, 99% with SEQ ID NO. 32.

The invention also provides a vector system comprising:
a) the vector as defined above, and
b) a second vector containing the at least one further expression cassette as defined above.

Preferably the vectors are viral vectors, preferably adeno virus vectors or adeno-associated virus (AAV) vectors.

Preferably the first and second vector are adeno-associated virus (AAV) vectors selected from the same or different AAV serotypes.

The invention also provides a host cell transformed with the vector as defined above or with the vector system as defined above.

The invention also provides a pharmaceutical composition comprising the polynucleotide as defined above, the vector as defined above, the vector system as defined above or the host cell as defined above and pharmaceutically acceptable vehicle.

The invention also provides the polynucleotide, the vector, the vector system, the host cell, or the pharmaceutical composition for medical use, preferably for use in gene therapy, preferably for use in the treatment and/or prevention of a retinal disease, preferably the retinal disease is characterized by a retinal degeneration, preferably the retinal disease is inherited.

Preferably the disease is selected from the group consisting of: retinitis pigmentosa (RP), Leber congenital amaurosis (LCA), rod-cone dystrophy, cone dystrophy.

The invention also provides a method for treating and/or preventing a retinal disease comprising administering to a subject in need thereof an effective amount of the polynucleotide, the vector, the vector system, the host cell, or the pharmaceutical composition as defined above.

Promoters obtained by substitution of fragment TGAACACCCCCAATCTCCCAGATGCT (sequence from nucleotide 77 to nucleotide 102 of SEQ ID NO. 1) in hRHOs wild-type (wt) promoter (sequence from nucleotide 77 to nucleotide 102 of SEQ ID NO. 1) with the above listed fragments (SEQ ID NO 12, 2 to 11) are promoters consisting of sequence, respectively:
a) SEQ ID NO. 23 (Prom hRHO-s-ΔZF6)
b) SEQ ID NO. 13 (Prom A)
c) SEQ ID NO. 14 (Prom B)
d) SEQ ID NO. 15 (Prom C)
e) SEQ ID NO. 16 (Prom D)
f) SEQ ID NO. 17 (Prom E)
g) SEQ ID NO. 18 (Prom F)
h) SEQ ID NO. 19 (Prom G)
i) SEQ ID NO. 20 (Prom H)
j) SEQ ID NO. 21 (Prom I)
k) SEQ ID NO. 22 (PROM L)
or they are promoters having at least 70% with each of SEQ ID NO 13 to 23, or at least 75%, 80%, 85%, 90%, 95%, 99% with each of SEQ ID NO 13 to 23 (promoter variants).

The promoter variant comprises the fragment TGAACACCCCCAATCTCCCAGATGCT (sequence from nucleotide 77 to nucleotide 102 of SEQ ID NO. 1) substituted with a sequence selected from the group consisting of SEQ ID NO. 2 to 12 or substituted with a sequence having an identity of at least 90% (preferably 92%, 95%, 97% or 99%) with any of SEQ ID NO. 2 to 12.

Consequently, the present invention is directed to polynucleotide promoters for use in a gene therapy method, said polynucleotide promoters having sequence selected from the group consisting of:

a) SEQ ID NO. 23
b) SEQ ID NO. 13
c) SEQ ID NO. 14
d) SEQ ID NO. 15
e) SEQ ID NO. 16
f) SEQ ID NO. 17
g) SEQ ID NO. 18
h) SEQ ID NO. 19
i) SEQ ID NO. 20
j) SEQ ID NO. 21
k) SEQ ID NO. 22
or having an identity of at least 70% with each of SEQ ID NO 13 to 23, or at least 75%, 80%, 85%, 90%, 95%, 99% with each of SEQ ID NO 13 to 23 (promoter variant). Preferably the polynucleotide shows a promoter activity in retina cells, preferably in photoreceptors, more preferably in rods. The promoters are synthetic.

BRIEF DESCRIPTION OF THE FIGURES

FIG. 1: Partial sequences (nucleotide 61 to 122) from human rhodopsin short (hRHOs) promoters, either wild-type (hRHOs-wt, SEQ ID NO 1) and modified (SEQ ID NO 13 to 23). The wild-type promoter fragment substituted in promoters Prom A to L and Prom hRHO-s-ΔZF6 is in bold. Mutagenized nucleotides are underlined in each modified promoter. Only partial sequences of the promoters are herein displayed, in order to focus on the mutagenized regions of each modified promoter.

DETAILED DESCRIPTION OF THE INVENTION

Figure 2:
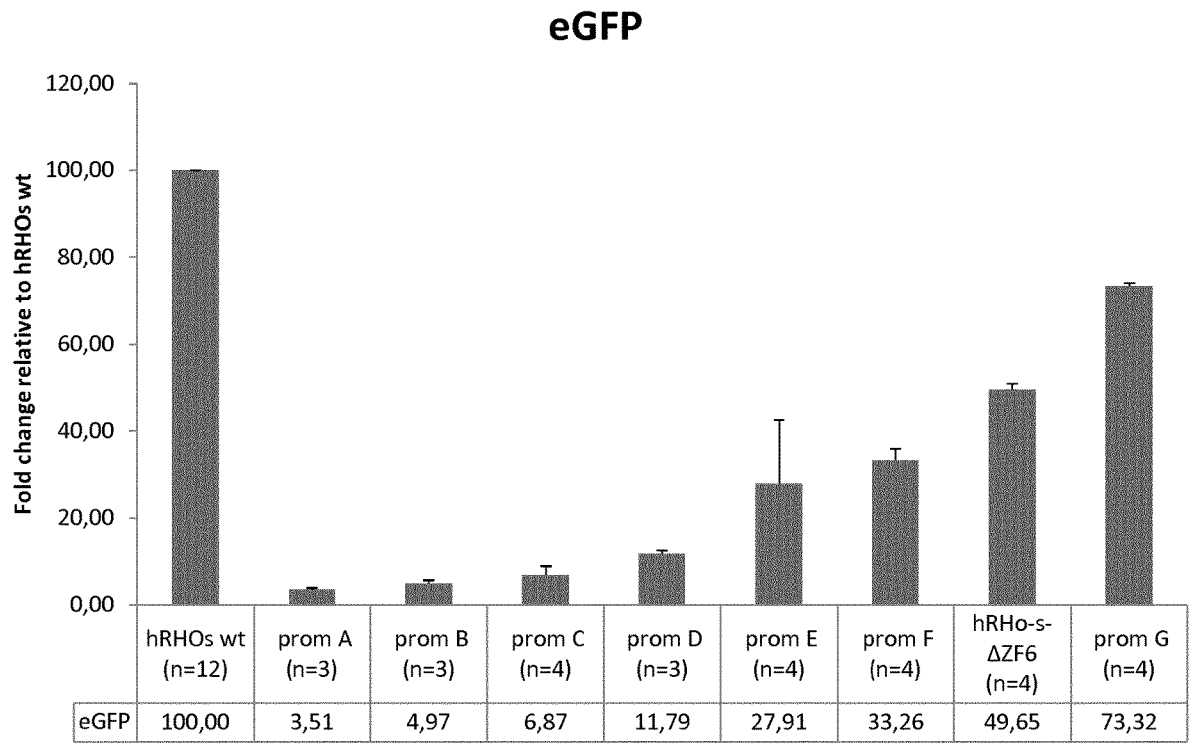
FIG. 2: Histogram from quantitative RT-PCR analysis of retinae of five weeks old C57 Bl6/J mice injected with AAV 2/8 (dose 3×10$^9$ gc) delivering vectors bearing eGFP under the control of different promoters, according to preferred embodiments of the invention. Mice were sacrificed after 15 days. In particular, the figure shows the eGFP expression driven by the hRHOs wt promoter or by each of eight modified promoters, according to preferred embodiments of the invention, having weaker activity compared to the wt. The promoter activities are all normalized to that of hRHOs-wt whose value is set to 100.

The term "promoter" is used herein to define a DNA polynucleotide capable of initiating transcription of a gene under its control; generally the gene under control of a promoter is located in a DNA region downstream said promoter. The terms "polynucleotide promoter" or "promoter" can be used interchangeably.

The term "modified promoter" is used herein to indicate the promoters of the invention, consisting in a hRHO short promoter wherein a fragment of the wild-type sequence has been substituted with a different (mutagenized) fragment.

Thus, the present invention provides the following polynucleotides as promoters showing modulatory (enhancing or repressing when compared to wild type promoter) activity in retina cells.

The polynucleotide may be selected selected from the group consisting of (a) to (c) shown below:
(a) a polynucleotide which contains the promoter sequence of the present invention (SEQ ID No. 2 to 12) or a sequence having an identity of at least 90% (preferably ate least 92%, 95%, 97% or 99%) with anyone sequence selected from the group consisting of SEQ ID NO. 2 to 12;
(b) a polynucleotide which has a nucleotide sequence sharing an identity of 70% or more with the promoter sequence of the present invention (SEQ ID No. 13 to 23) and which shows promoter activity in eukaryotic cells; and
(c) a polynucleotide which is hybridizable under stringent conditions with a polynucleotide consisting of a nucleotide sequence complementary to the promoter sequence of the present invention and which shows promoter activity in retina cells.

The above polynucleotides shown in (a) to (c) are each hereinafter referred to as "the polynucleotide of the present invention."

An additional sequence(s) (e.g., an enhancer sequence) other than the promoter sequence of the present invention may be added to the upstream (5'-terminal side) or downstream (3'-terminal side) of the promoter sequence of the present invention. Such an additional sequence may be added to the promoter sequence of the present invention via a nucleotide sequence of 1 to 1000 bp, 1 to 900 bp, 1 to 800 bp, 1 to 700 bp, 1 to 600 bp, 1 to 500 bp, 1 to 400 bp, 1 to 300 bp, 1 to 200 bp, 1 to 100 bp, 1 to 75 bp, 1 to 50 bp, 1 to 25 bp or 1 to 10 bp, or alternatively, may be directly added to the promoter sequence of the present invention (i.e., the number of nucleotide residues located between the promoter sequence of the present invention and the additional sequence is zero).

As used herein, the term "polynucleotide" is intended to mean DNA or RNA. As used herein, the expression "polynucleotide which is hybridizable under stringent conditions" is intended to mean, for example, a polynucleotide that can be obtained by means of, e.g., colony hybridization, plaque hybridization or Southern hybridization using, as a probe, the whole or a part of a polynucleotide consisting of a nucleotide sequence complementary to the promoter sequence of the present invention. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997." As used herein, the term "high stringent conditions" is intended to mean, for example, conditions of (1) 5×SSC, 5×Denhardt's solution, 0.5% SDS, 50% formamide and 50° C., (2) 0.2×SSC, 0.1% SDS and 60° C., (3) 0.2×SSC, 0.1% SDS and 62° C., (4) 0.2×SSC, 0.1% SDS and 65° C., or (5) 0.1×SSC, 0.1% SDS and 65° C., without being limited thereto. Under these conditions, it can be expected that DNA having a higher sequence identity is more efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that a commercially available kit is used for hybridization, an Alkphos Direct Labelling and Detection System (GE Healthcare) may be used for this purpose, by way of example. In this case, hybridization may be accomplished in accordance with the protocol attached to the kit, i.e. a membrane may be incubated overnight with a labeled probe and then washed with a primary washing buffer containing 0.1% (w/v) SDS under conditions of 55° C. to detect the hybridized DNA. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to the promoter sequence of the present invention, a DIG nucleic acid detection kit (Roche Diagnostics) may be used for detection of hybridization.

In addition to those listed above, other hybridizable polynucleotides include polynucleotides sharing an identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the promoter sequence of the present invention, as calculated by homology search software such as FASTA or BLAST using default parameters.

It should be noted that the identity of nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, tblastn and tblastx have been developed (Altschul S F, et al: J Mol Biol 215: 403, 1990). If blastn is used for nucleotide sequence analysis, parameters may be set to, for example, score=100 and wordlength=12. If BLAST and Gapped BLAST programs are used, default parameters in each program may be used.

In the context of the present invention, the term "promoter activity" is intended to mean that when a protein-encoding gene sequence (hereinafter referred to as a "target gene" or "transgene") is inserted downstream of the promoter of the present invention, an expression product of this gene is obtained.

The term "expression product" used here is intended to mean either or both of RNA (e.g., hnRNA, mRNA, siRNA or miRNA) which is a transcribed product of the gene and a protein which is a translated product of the gene.

Insertion of a target gene may be accomplished such that the 5'-terminal end of the target gene is located in a region within 500 bp, 400 bp, 300 bp, 200 bp, 100 bp, 50 bp, 30 bp or 10 bp from the 3'-terminal end of the promoter sequence of the present invention. In the case of attempting to confirm the activity of the promoter sequence of the present invention, the target gene is not limited in any way, but is preferably a gene encoding a protein whose activity can be measured by established method.

Examples of such a gene include, but are not limited to, selection marker genes such as neomycin resistance gene, hygromycin B phosphotransferase gene and so on, as well as expression reporter genes such as LacZ, GFP or eGFP (Green Fluorescence Protein or enhanced Green Fluorescence Protein, respectively), luciferase genes, etc.

The promoters of the present invention preferably have an enhanced or decreased activity when compared to the wild-type RHO promoter activity. Preferably, the promoter of the invention have a promoter activity that is decreased by at least 20%, preferably at least 25%, preferably at least 30%, preferably at least 50%, preferably at least 70%, preferably up tp 90%, 95%, 96, 5% when compared to the wild-type RHO promoter activity.

Preferably, the promoter of the invention have a promoter activity that is increased by at least 40%, preferably at least 50%, preferably at least 60%, preferably at least 70%, preferably at least 80%, preferably at least 100% and up to 150%, 200%, 250% when compared to the wild-type RHO promoter activity.

Procedures for gene transfer into host cells are known in the art and any on them may be used. These include among others: transformation and transfection (transfer of foreign DNA into cultured host cells mediated through chemicals). In transfections the charged chemical substances such as cationic liposomes, calcium phosphate of DEAE dextran are taken and mixed with DNA molecules. The recipient host cells are overlayed by this mixture. Consequently the foreign DNA is taken up by the host cells. Electro poration (Electric Field-mediated Membrane Permeation). In electroporation an electric current at high voltage (about 350 V) is applied in a solution containing foreign DNA and fragile host cells. This creates transient microscopic pores in cell membrane. Consequently foreign DNA enters into the host through these pores. Other procedures include microinjection and Particle Bombardment Gun. In microinjection technique, foreign DNA is directly and forcibly injected into the nucleus of animal and plant cells through a glass micropipette containing very fine tip of about 0.5 mm diameter. Particle Bombardment Gun (Biolistics) was developed by Stanford in 1987. In this method macroscopic gold or tungusten particles are coated with desired DNA. A plastic micro-carrier containing DNA coated gold/tungusten particles are placed near rupture disc. The particles are bombarded onto target cells by the bombardment apparatus. Consequently foreign DNA is forcibly delivered into the host cells.

The polynucleotide of the present invention mentioned above can be obtained by known genetic engineering procedures or known synthesis procedures.

Vectors

In another embodiment, the present invention also provides an expression vector containing the polynucleotide of the present invention (hereinafter referred to as "the vector of the present invention").

The vector of the present invention is generally configured to comprise an expression cassette comprising: i) the promoter of the present invention; and ii) as constituent elements, signals that function in host cells for transcription termination and polyadenylation of an RNA molecule. According to a preferred embodiment, the present invention is directed to a vector comprising the polynucleotide promoter of the invention and a polynucleotide operatively linked to said promoter, preferably encoding for a transcriptional repressor. Preferably, said vector is an expression vector, suitable for nucleic acid expression in eukaryotic cells, more particularly in mammalian cells, or a viral vector, suitable for gene therapy. Preferably, said vector is for use in gene therapy.

According to a preferred embodiment, the present invention is directed to a vector suitable for repressing transcription of rhodopsin (RHO), said vector comprising a polynucleotide promoter of the invention and a polynucleotide encoding a rhodopsin (RHO) transcriptional repressor under the control of said promoter. Preferably said vector is for use in gene therapy. Preferably said vector is an expression vector or a viral vector.

Procedures for gene transfer into host cells therefore also include gene transfer by viral vectors.

The thus configured vector is introduced into host cells. Examples of appropriate host cells used in the present invention are indicated below.

The term "transgene" is used herein to indicate any polynucleotide cloned within an expression vector, under the control of a promoter. In exemplary non-limiting embodiments a transgene may be a polynucleotide of sequence comprising the full length sequence of a gene, preferably a full length sequence of a mammalian gene, or it may be a polynucleotide of sequence comprising the coding sequence of a gene, optionally further comprising regulatory sequences (e.g. UTR sequences or introns). Still, a transgene may comprise a small piece of nucleic acid flanked by homologous regions for use in a cell (i.e. for gene correction). The transgene may otherwise comprises a gene encoding a functional or structural component such as a shRNA, RNAi, miRNA, a DNA-binding protein, or the like, or it may comprise a gene encoding a regulatory element that binds to and/or modulates expression of a gene of interest. In certain embodiments, a transgene sequence comprises a sequence encoding an antibody, an antigen, an enzyme, a growth factor, a transcription factor (natural or artificial), a receptor (cell surface or nuclear), a hormone, a lymphokine, a cytokine, a reporter, functional fragments of any of the above and combinations of the above.

The term "expression cassette" is used herein to indicate a polynucleotide to be cloned or cloned in a vector and comprising a promoter and a transgene whose expression is controlled by said promoter. Multicistronic vectors comprise two or more "expression cassettes" as herein defined.

The "activity of a promoter" is used herein to indicate the strength of a promoter in driving expression of a downstream transgene, i.e. at which protein level a protein under regulation of a promoter is expressed. The activity of a promoter can be measured by analysing the expression level of a protein, whose coding sequence is cloned under control of said promoter, e.g. a reporter protein such as eGFP. For example, to evaluate the strength of a promoter, a first construct bearing a reporter gene under the control of said promoter can be delivered in vivo or in vitro to a cell, and a second reference construct bearing a second reporter gene under a different promoter (promoter of reference), can be delivered under the same conditions. Then, expression of the two reporter proteins can be assessed by quantitative RT-PCR analysis or western blot analysis and compared. When the first reporter shows higher expression level (e.g. higher levels of reporter mRNA or of reporter protein) compared to the second reporter, the first promoter is considered having stronger activity compared to the promoter of reference and vice versa. As shown hereafter in example 1, the inventors have retinally delivered in vivo, by means of AAV2/8 vector, a reference construct bearing eGFP under hRHOs-wt (SEQ ID NO. 1), at the dose of $3 \times 10^9$ gc and after 15 days the eGFP expression levels was evaluated by quantitative RT-PCR analysis. Then constructs bearing eGFP under the modified hRHOs promoters of the invention, according to the invention, have been systematically delivered subretinally, under the same conditions, and eGFP expression has been evaluated by quantitative RT-PCR analysis after 15 days. The strength of the promoters of the invention has been defined as: "ACTIVITY WEAKER THAN SEQ ID NO. 1", or "ACTIVITY STRONGER THAN SEQ ID NO. 1" compared to the activity of the hRHOs-wt (SEQ ID NO.1), by normalizing the activities of the promoters of the invention to that of hRHOs-wt, set as reference, whose activity value was set to 100. Therefore, "ACTIVITY WEAKER THAN SEQ ID NO. 1" means any normalized value below 100, while "ACTIVITY STRONGER THAN SEQ ID NO. 1" means any normalized value beyond 100.

The promoters of the present invention comprising SEQ ID No. 2 to 8 and 12 preferably have a promoter activity weaker than promoter of SEQ ID No. 1 of at least 20%, preferably at least 25%, preferably at least 30%, preferably at least 50%, preferably at least 70%, preferably up to 90%, 95%, 96, 5%.

Preferably, the promoter of the invention comprising SEQ ID No. 9 to 11 have a promoter activity stronger than promoter of SEQ ID No. 1 of at least 40%, preferably at least 50%, preferably at least 60%, preferably at least 70%, preferably at least 80%, preferably at least 100% and up to 150%, 200%, 250%.

A "transcriptional repressor" is herein defined as a molecule capable of reducing or abolishing expression of a transcript encoding for a protein or a functional transcript (small RNAs for instance), when expressed in a cell. Exemplary transcriptional repressors include: interfering polynucleotides, such as a siRNA, a shRNA, a miRNA a pre-miRNA, a pri-miRNA, or an antisense nucleotide, targeting a specific transcript; an artificial transcription factor (ATF), comprising a DNA binding domain coupled to effector domains, such as those described in Mussolino et al., or an artificial protein consisting in an isolated DNA binding domain (herein after "DNA Binding Domain or DBD), i.e. without any effector domain, such as those described in WO2015075154.

A "DNA-binding domain" (DBD) is an independently folded protein domain that contains at least one motif that recognizes double- or single-stranded DNA. A DBD can recognize a specific DNA sequence (a recognition or regulatory sequence) or have a general affinity to DNA. One or more DNA-binding domains are usually part of a so-called DNA binding protein, i.e. a larger protein consisting of additional domains with differing function. The additional domains often regulate the activity of the DNA-binding domain. The function of DNA binding is either structural or involving transcription regulation, with the two roles sometimes overlapping. Transcription factors (TFs) are DNA-binding proteins composed of two main functional domains, the effector domain and the DNA binding domain. The effector domains are responsible of transcription activation and repression. The activator-domain and repressor-domain work mainly by recruitment of large transcriptional coactivators and corepressors complexes via protein-protein interactions. Therefore in summary both natural transcription factors and artificial DNA-binding proteins have both one or more DBDs and effectors domains which attracts by protein-protein interactions a number of other proteins which can ultimately result in either transcriptional repression or transcriptional activation.

On the contrary, DBDs are external to the topology of the regulatory network and are transcriptionally independent from the endogenous cell-specific regulatory code (whole cell-specific transcriptome map). Therefore, artificial isolated DBDs (or DBDs) are suited to generate potent means to efficaciously and safely modulate transcription, then leading to generate therapeutics.

The DBDs that can be employed in the vectors of the present invention may be zinc finger domains (ZF) or transcription activator-like DNA binding domains (TAL) or RNA-guided DNA-binding domains (Crispr/cas 9), either synthetic or artificial. The DNA binding domain may be a functional fragment or a derivative of the above domain.

A functional fragment is a domain that lacks one or more modules and that nevertheless maintains the ability to recognize the specific regulatory sequence.

A derivative is a domain that contains mutations, substitutions and that nevertheless maintains the ability to recognize the specific regulatory sequence.

A man skilled in the art is well aware of the methods for designing ZF or TAL or Crispr/cas domains and fragments and derivative thereof and testing specificity.

A single ZF motif (also called module) consists of approximately 30 amino acids with a simple beta-beta-alpha fold that is stabilized by hydrophobic interactions and the chelation of a single zinc ion. Each ZF module primarily recognizes an overlapping 3-4-bp DNA sequence, where the last base pair is the first of the following target (the fourth base of each target is on the opposite strand). The binding takes place through key amino-acid residues, which can be exchanged to generate ZF modules with different sequence specificities. To obtain a DBD that is tailored to a unique target sequence one or more ZF modules can be consecutively linked, in particular at least two ZF modules, at least three ZF modules, at least four ZF modules, at least five ZF modules or six ZF modules.

The general structure of DNA-binding domains derived from transcription activator-like effectors (TALEs), which are derived from the plant pathogenic *Xanthomonas* spp. bacterium or TALE-like proteins from *Ralstonia* spp. can also be engineered to bind to predetermined DNA sequences (Li, L. et al. 2013). TAL-DBD are composed of tandem arrays of 33-35 amino acid repeats, each of which recognizes a single base-pair in the major groove.

The CRISPR (clustered regularly interspaced short palindromic repeats) system provides a potential platform for targeted gene regulation (Barrangou et al., 2007). CRISPR systems have been found in different organisms; one of the simplest is the type II CRISPR system from *Streptococcus pyogenes*. In this system, a single gene encoding the Cas9 protein and two RNAs, a mature CRISPR RNA (crRNA) and a partially complementary trans-acting RNA (tracrRNA), are necessary and sufficient for RNA-guided silencing of foreign DNAs. The mutant protein Cas9, which is defective in DNA cleavage, can actually act as a simple RNA-guided DNA-binding domain.

Therefore, the CRISPR/Cas system of *Streptococcus pyogenes* can be programmed to design DNA binding domain to specific eukaryotic regulatory sequences through the simple engineering of guide RNAs with base-pairing complementarity to such regulatory DNA sites. Cas9 can be used as a customizable RNA-guided DNA-binding platform.

A RHO transcriptional repressor is a molecule capable of reducing or abolishing expression of RHO protein, when expressed in a cell, preferably of human RHO protein (NP_000530.1). Preferred RHO transcriptional repressors, according to the present invention, include: an antisense oligonucleotide, a siRNA, a shRNA or a miRNA, targeting a RHO transcript; an artificial transcription factor (ATF) comprising a DNA Binding domain coupled to one or more effector domains, targeting a sequence of the hRHO promoter; an isolated DNA Binding domain (DNA binding domain or DBD), targeting a sequence of the hRHO promoter.

Preferably said ATF is a zinc-finger ATF (ZF-ATF), more preferably a ZF-ATF targeting the RHO promoter in any of the following sequences of the hRHO promoter (plus or minus strand): SEQ ID No. 34 to SEQ ID No. 42, as described also in Mussolino et al.

Preferably the effector domain of the ATF is human derived Krüppel-associated box (KRAB) repression domain (SEQ ID No. 50) (Margolin et al., 1994), or an effector domain having a sequence having at least 90% identity to SEQ ID No. 50.

Further suitable effector domains of the ATF include the herpes simplex virus-based transcriptional activator VP64 domain (Seipel et al, 1992).

According to a preferred embodiment, the polynucleotide encoding a RHO transcriptional repressor is a polynucleotide encoding a an isolated DNA binding domain (DBD). Preferably said DBD targets the RHO promoter in any of the following sequences (on its plus or minus strand): SEQ ID No. 34 to SEQ ID No. 42 (see also Mussolino et al).

More preferably said polynucleotide encoding a RHO transcriptional repressor has sequence selected from the group consisting of: ZF6-DBD, SEQ ID No. 24, ZF2, SEQ ID No. 26, TAL01, SEQ ID No. 28, TAL02, SEQ ID No. 30, ZF6-5F, SEQ ID No. 43, TALI-DBD, SEQ ID No. 45, TALRHO(02)DBD, SEQ ID No. 47.

More preferably the polynucleotide encoding a DNA Binding protein consisting in an isolated DNA binding domain (DBD) is of sequence consisting essentially of ZF6-DBD sequence (SEQ ID No. 24), or a fragment or derivative thereof.

In a further embodiment, the present invention relates to a vector that comprises a first expression cassette comprising a nucleotide encoding for a transcriptional repressor under the control of any of the promoters of the invention, and a second expression cassette comprising a polynucleotide encoding for a retinal gene whose mutation causes inherited retinal degeneration (replacement gene).

Said transcriptional repressor is preferably a DNA binding domain (DBD) targeting a DNA regulatory sequence controlling the expression of a gene (target gene) selected from the group consisting of: RHO, BEST1, CA4, RP17, CRX, FSCN2, RP30, GUCA1B, RP48, IMPDH1, RP10, KLHL7, RP42, NR2E3, NRL, RP27, ORP1, DCDC4A, RP1, PRPF3, RP18, PRPF31, PRPF6, rp60, PRPF8, PRPH2, RDS, RP7, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2 and RP33, more preferably said target gene is RHO. Preferably said gene is in a mutated form or a wild-type form. The mutated form of said gene is responsible for an inherited eye disease, preferably an autosomal dominant inherited eye disease, preferably an autosomal recessive inherited eye disease. It can be any mutation in the genes reported in Table 1.

Said retinal gene whose mutation causes inherited retinal degeneration (replacement gene) is preferably selected from the group consisting of: RHO, BEST1, CA4, RP17, CRX, FSCN2, RP30, GUCA1B, RP48, IMPDH1, RP10, KLHL7, RP42, NR2E3, NRL, RP27, ORP1, DCDC4A, RP1, PRPF3, RP18, PRPF31, PRPF6, rp60, PRPF8, PRPH2, RDS, RP7, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2, RP33. More preferably, said replacement gene is RHO.

In particular BEST1, NR2E3, NRL, RHO, RP1, RPE65 are genes that cause both autosomal dominant and recessive inherited eye disease, such as Autosomal Dominant Retinitis Pigmentosa and Autosomal Recessive Retinitis Pigmentosa.

Preferably said target gene and/or replacement gene is a mammalian gene, more preferably a human gene.

In a preferred embodiment, said second expression cassette further comprises a retina specific promoter upstream of said gene, preferably said retina specific promoter is a rod-specific promoter.

Preferably, the retina specific promoter is the rhodopsin kinase (RHOK) promoter or the transducin 1 (GNAT1) promoter; more preferably it is the human transducin 1 (GNAT1) promoter.

According to a preferred embodiment of the invention, said vector comprises a first expression cassette comprising hRHO-s-ΔZF6 promoter (SEQ ID No. 23) coupled to a polynucleotide encoding ZF6-DBD transcription repressor (SEQ ID No. 24); preferably said vector further comprises a second expression cassette comprising hGNAT1 promoter (SEQ ID NO. 52) coupled to a polynucleotide encoding for hRHO (SEQ ID NO 49). Preferably, said vector is of sequence SEQ ID NO 32 (DBD-R vector).

More preferably, said vector is for use in gene therapy.

A vector comprising a first expression cassette for the expression of a RHO transcriptional repressor, under the control of the promoter of the invention, and a second expression cassette for the expression of the wild-type form of rhodopsin (repression-replacement strategy) is particularly advantageous for the gene therapy of retinal diseases. In fact, the repression-replacement strategy, leads to: (i) mutational-independent silencing of the human rhodopsin gene (transcriptional silencing targeted to both wild-type and mutated RHO alleles) and (ii) gene replacement of the endogenous RHO copies by vector-mediated photoreceptor transgene transfer.

The use of a single vector ensures the simultaneous expression in the same transduced photoreceptor of any expression cassette comprised in said vector. Moreover, the use of the promoter of the invention allows the contemporary modulation of the expression of the first and second cassettes, independently from the vector dose used.

As an example, the inclusion of the promoters of the invention in the vector for repression-replacement allows the use of vector doses suitable for achieving therapeutic levels of the replacement gene, still maintaining the possibility to fine tuning of the expression of the repressor by selecting the appropriate promoter. It is in fact possible, as an example, to use a high vector titer, in order to achieve sufficient and specific expression of the replacement gene, and the repressor under the control of a promoter of the invention having weaker activity compared to the wild-type RHOs promoter, in order to achieve sufficient repression of the mutated gene, still maintaining high specificity in the expression of said transcriptional repressor (see example 2).

According to a preferred embodiment, the invention is directed to a vector comprising at least one expression cassette comprising the promoter of the invention. In a further preferred embodiment, said multicistronic vector comprises at least two expression cassettes, wherein each expression cassette comprises a promoter of the invention, and wherein said promoters are the same or different.

One can assemble in a single vector multiple copies of distinct promoters elements obtaining differential expression levels from distinct constructs to simultaneously modulate transcript and/or protein products: As an example, this is particularly relevant for treating photoreceptors (rod) and potentially other neurological and non-neurological disorders. Preferably a vector according to anyone of the embodiments of the invention is a viral vector. Preferably said vector is selected from the group consisting of: adenoviral vectors, lentiviral vectors, retroviral vectors, adeno associated viral vectors (AAV) or naked plasmid DNA vectors. Preferably said viral vectors show improved transduction in retinal cells, more preferably in photoreceptors, still preferably in rods.

According to a preferred embodiment, said vector is an adeno-associated viral vector. Preferably the adeno-associated viral vector is selected from AAV of serotype 2, serotype 4, serotype 5, serotype 6, serotype 7, serotype 8, or serotype 9; more preferably the AAV serotype is 2/2, 2/4, 2/5, 2/6, 2/7, 2/8, or 2/9.

According to a preferred embodiment of the invention, the AAV capside may include modifications, such as aminoacid substitutions or deletions, to improve transduction into cells. AAVs are by far the most commonly used vector for targeting therapy to photoreceptors. However, their use is limited by its small cloning capacity of only 4.7 kb. As the coding sequences of many disease genes are of this size or larger, using this vector to target such diseases is not easily achieved. Even when targeting genes whose coding sequence is 4.7 kb, relatively little space is left for inclusion of an appropriate promoter to drive transgene expression. The promoters of the invention are thus particularly advantageous when used within AAVs, in view of their small size.

The present invention also provides a viral particle containing any of the vectors of the invention.

The present invention further provides a host cell transformed by any of the vectors of the invention.

The present invention also provides a pharmaceutical composition comprising the polynucleotide or the host cell or the vector or the viral particle as defined above and a pharmaceutically acceptable excipient.

In the present invention any combination of the nucleic acid, host cell or vector or a viral particle as defined above may be used in the pharmaceutical composition.

Preferably the polynucleotide or the vector or the host cell or the viral particle or the pharmaceutical composition of the invention as defined above is for use in gene therapy, preferably for use in the treatment of an eye disease. Preferably, said eye disease is an inherited eye disease. The inherited eye disease may be an autosomal dominant inherited eye disease and/or an autosomal recessive inherited eye disease.

Still preferably, the polynucleotide or the vector or the host cell or the viral particle or the pharmaceutical composition of the invention as defined above is for use in the treatment of a retinal dystrophy. Preferably, the retinal dystrophy is characterized by photoreceptor degeneration. Preferably, the retinal dystrophy is selected from the group consisting of: Retinitis Pigmentosa (RP), Leber Congenital Amaurosis (LCA), cone-rod dystrophies and cone dystrophies. Preferably, the retinal dystrophy is an inherited retinal dystrophy.

According to a preferred embodiment, the retinal dystrophy is autosomal dominant retinitis pigmentosa (ADRP), autosomal recessive retinitis pigmentosa or Congenital Stationary Night Blindness.

Preferably the treatment is a gene therapy.

The present invention provides a method for the treatment of an eye disease, preferably of an inherited eye disease of a subject in need thereof, said method comprising administering a suitable amount of the protein or the nucleic acid or the vector or the host cell or the viral particle or the pharmaceutical composition as defined above.

Preferably the molecule or the composition of the invention is administered in the retina.

The vectors of the present invention may be administered to a patient. A skilled worker would be able to determine appropriate dosage rates. The term "administered" includes delivery by viral or non-viral techniques. The vectors may, for example, be plasmid vectors, mRNA vectors (e.g. in vitro transcribed mRNA vectors) or viral vectors. Viral delivery mechanisms include but are not limited to adenoviral vectors, adeno-associated viral (AAV) vectors, herpes viral vectors, retroviral vectors, lentiviral vectors, and baculoviral vectors vaccinia viruses, foamy viruses, cytomegaloviruses, Semliki forest virus, poxviruses, RNA virus vector and DNA virus vector. etc as described above. Such viral vectors are well known in the art. Non-viral delivery mechanisms include lipid mediated transfection, liposomes, immunoliposomes, lipofectin, cationic facial amphiphiles (CFAs) and combinations thereof.

The present invention also provides a pharmaceutical composition for treating an individual, wherein the composition comprises a therapeutically effective amount of the nucleic acid or vector or host cell of the present invention or a viral particle produced by or obtained from same. The pharmaceutical composition may be for human or animal usage. Typically, a physician will determine the actual dosage which will be most suitable for an individual subject and it will vary with the age, weight and response of the particular individual. The composition may optionally comprise a pharmaceutically acceptable carrier, diluent, excipient or adjuvant. The choice of pharmaceutical carrier, excipient or diluent can be selected with regard to the intended route of administration and standard pharmaceutical practice.

The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. In one aspect, the parenteral administration route may be intraocular administration. Intraocular administration of the present composition can be accomplished by injection or direct (e.g., topical) administration to the eye. In addition to the topical routes of administration to the eye described above, suitable intraocular routes of administration include intravitreal, intraretinal, subretinal, subtenon, peri- and retro-orbital, trans-corneal and trans-scleral administration. Such intraocular administration routes are within the skill in the art.

For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The man skilled in the art is well aware of the standard methods for incorporation of a polynucleotide or vector into a host cell, for example transfection, lipofection, electroporation, microinjection, viral infection, thermal shock, transformation after chemical permeabilisation of the membrane or cell fusion.

As used herein, the term "host cell or host cell genetically engineered" relates to host cells which have been transduced, transformed or transfected with the vector here described.

As representative examples of appropriate host cells, one can cites bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. The host cell can be a retinal cell, preferably a photoreceptor cell, more preferably a rod cell. Preferably, said host cell is an animal cell, and most preferably a human cell. The host cell can be a cultured cell or a primary cell, i.e., isolated directly from an organism, e.g., a human. The host cell can be an adherent cell or a suspended cell, i.e., a cell that grows in suspension. Administration of a therapeutically active amount of the pharmaceutical compositions of the present invention, or an "effective amount", is defined as an amount effective at dosages and for periods of time, necessary to achieve the desired result of increasing/decreasing the production of proteins. A therapeutically effective amount of a substance may vary according to factors such as the disease state/health, age, sex, and weight of the recipient, and the inherent ability of the particular polypeptide, nucleic acid coding therefore, or recombinant virus to elicit the desired response. Dosage regimen may be adjusted to provide the optimum therapeutic response. For example, several divided doses may be administered daily or at periodic intervals, and/or the dose may be proportionally reduced as indicated by the exigencies of the therapeutic situation. For instance, in general for viral vectors administration, suitable dosages will vary from $10^8$ to $10^{13}$ gc (genomes copies)/eye, preferably from $10^9$ to $10^{12}$ gc/eye, more preferably from $10^{10}$ to $10^{11}$ gc/eye.

EXAMPLES

Example 1

Preparation of hRHO Short Modified Promoters and Activity Analysis

Figure 3:
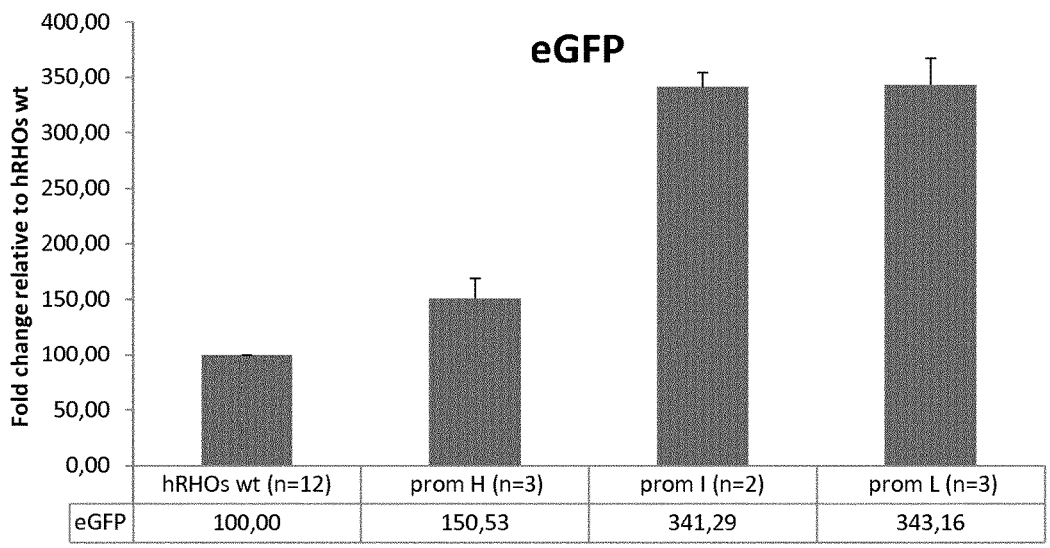
FIG. 3: Histogram from quantitative RT-PCR analysis retinae of five weeks old C57 Bl6/J mice injected with AAV 2/8 (dose 3×10$^9$ gc) delivering vectors bearing eGFP under the control of different promoters, according to preferred embodiments of the invention. Mice were sacrificed after 15 days. In particular, the figure shows the eGFP expression driven by the hRHOs wt promoter and three modified promoters, according to a preferred embodiment of the invention, having stronger activity compared to the wt. The promoter activities are all normalized to that of hRHOs-wt whose value is set to 100.
Figure 4:
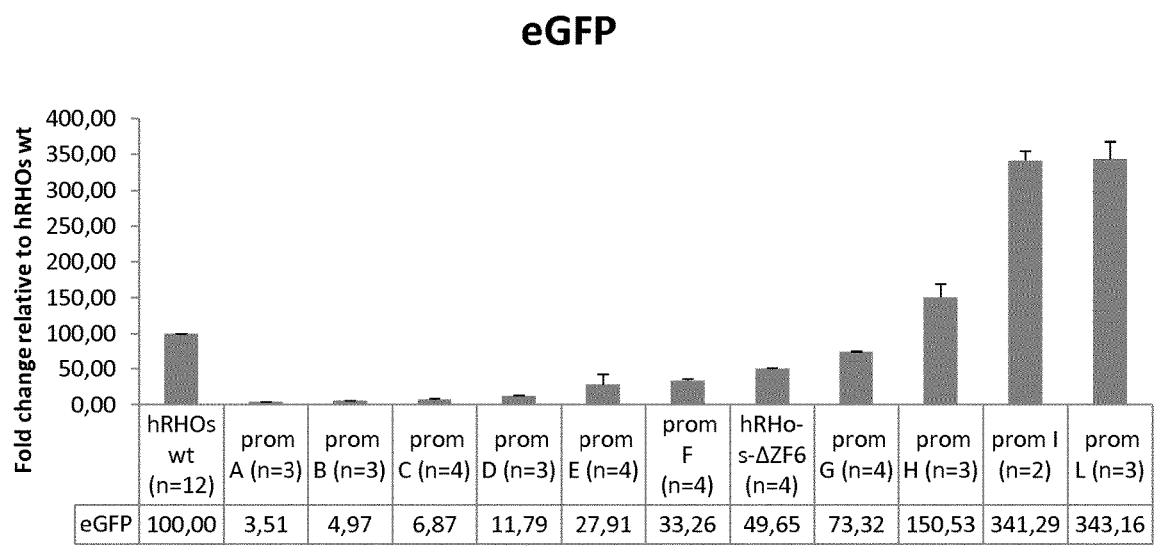
FIG. 4: Histogram from quantitative RT-PCR analysis of retinae of five weeks old C57 Bl6/J mice injected with AAV 2/8 (dose 3×10$^9$ gc) delivering vectors bearing eGFP under the control of different promoters, according to preferred embodiments of the invention. Mice were sacrificed after 15 days. In particular, the image shows the eGFP expression driven by the hRHOs wt promoter and the eleven modified promoters of the invention. The promoter activities are all normalized to that of hRHOs-wt whose value is set to 100.

Modified sequences of hRHO short promoter have been prepared, in order to modulate its activity, by mutagenizing the hRHO short wt promoter (SEQ ID No. 1) in the region from nucleotide 77 to nucleotide 102 of SEQ ID NO. 1 (corresponding to region ranging from −88-63 bp to TSS of hRHO promoter). Eleven modified promoters have been obtained (FIG. 1). Sub-retinal injection was performed of all the constructs (injected 1 at the time) driving the eGFP under the control of different hRHO short promoters, delivered by AAV8 viral vectors in five weeks old C57 Bl6/J mice with a dose of $3 \times 10^9$ gc. After 15 days the animals were sacrificed and the eGFP transcript level were analysed in retinae by quantitative Real Time PCR (FIGS. 2-4). The promoters of the invention show reduced/increased strength (activity weaker/stronger, respectively) compared to the wt hRHO short promoter of SEQ ID No. 1.

The promoter strength is determined in terms of levels of expression of the downstream transgene (eGFP in the instant example). In particular, FIG. 2 shows promoters according to the invention having weaker activity compared to the wt hRHO short promoter, as assessed by decreased levels of eGFP transcripts. FIG. 3 shows promoters according to the invention having stronger activity compared to the wt hRHO short promoter, as assessed by increased levels of eGFP transcripts. FIG. 4 shows the activity of the entire set of promoters of the invention.

According to the previous definitions of "Promoter ACTIVITY WEAKER" and "Promoter ACTIVITY STRONGER", the ranked list of the promoters of the present invention, from the weaker to the stronger is thus:

Promoter A (Prom A; SEQ ID No. 13), Promoter B (Prom B; SEQ ID No. 14), Promoter C (Prom C; SEQ ID No. 15), Promoter D (Prom D; SEQ ID No. 16), Promoter E (Prom E; SEQ ID No. 17), Promoter F (Prom F; SEQ ID No. 18), Promoter hRHO-s-ΔZF6 (Prom hRHO-s-ΔZF6; SEQ ID No. 23), Promoter G (Prom G; SEQ ID No. 19), Promoter H (Prom H; SEQ ID No. 20), Promoter I (Prom I; SEQ ID No. 21), Promoter L (Prom L; SEQ ID No. 22), wherein Promoters A to G and promoter hRHO-s-ΔZF6 have weaker activity than wild-type hRHO short promoter (hRHOs wt), while Promoters H to L have stronger activity than hRHOs wt promoter (FIGS. 2-4).

Figure 5:
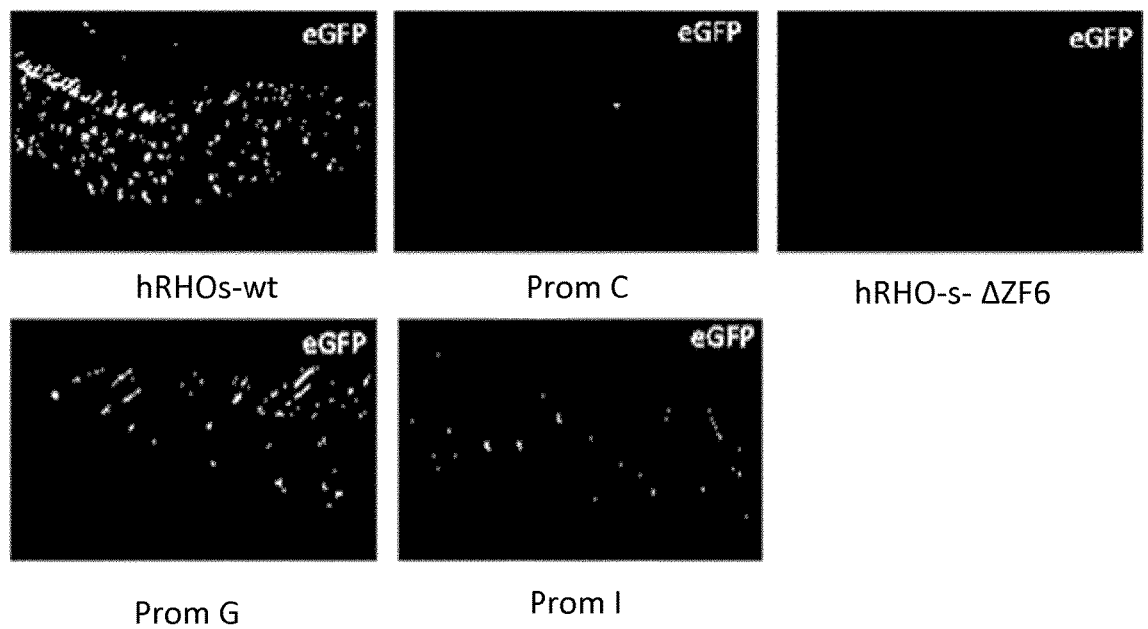
FIG. 5: Histological analysis of C57 Bl6/J five weeks old mice retinae injected with AAV2/8 carrying eGFP under control of hRHOs wt promoter, Prom C, Prom G, Prom I or Prom hRHO-s-ΔZF6 promoters (dose 3×10$^9$ gc), according to preferred embodiments of the invention. Mice were sacrificed after 15 days. The images show the eGFP-positive retinal portion transduced. Magnification 20×.

The results thus show that it is possible to fine-tune, increase or reduce, the activity of rhodopsin promoter by the 11 different mutagenesis, according to the invention. In this way it is possible to provide novel promoter elements with differential promoter strength to be used as modulators of expression of one or more transgenes for advantageous use in gene therapy. Furthermore, the histological analysis demonstrates the rod-specific localization of eGFP expression, driven by the promoters of the invention, indicating that the mutagenesis of RHO promoter doesn't alter the specificity of transgene expression driving in retinal cells, in particular rods (FIG. 5).

Example 2

In Vivo Testing in Gene Therapy Silencing-Replacement Strategy

Gene therapy by silencing-replacement strategy, according to a preferred embodiment of the invention, has been carried out in porcine retina, by coupling porcine Rho (pRho) transcriptional repression by means of ZF6-DBD (SEQ ID No. 24) and concurrent replacement of human RHO (hRHO CDS; SEQ ID NO 49), to complement Rho transcriptional repression. Pig is a valuable large animal model for preclinical studies (Mussolino et al, Gen Ther 2011). It is noted that due to high conservation between sequences of pig and human ZF6-DBD target region, repression by ZF6-DBD is suitable for hRHO as well as for pRho.

Figure 7:
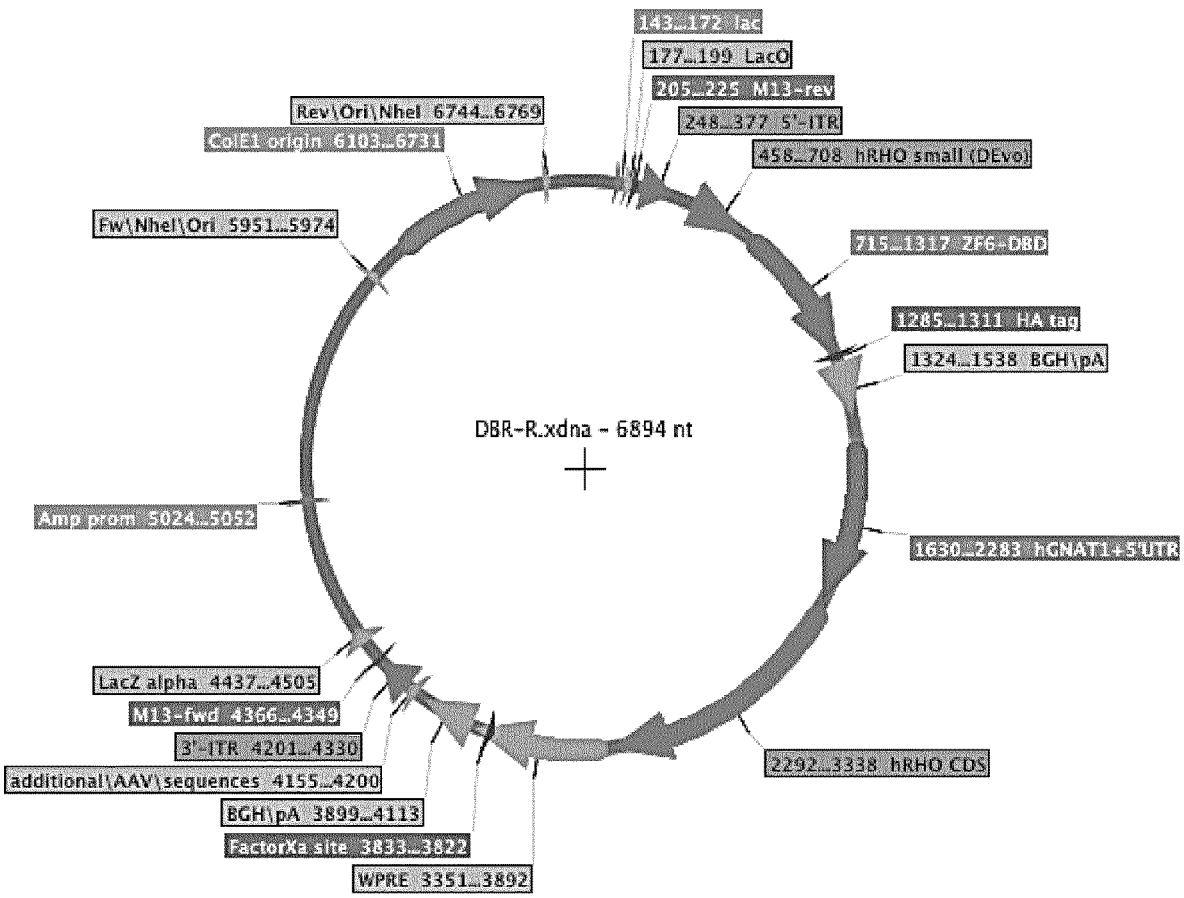
FIG. 7: Plasmid map of DBD-R construct (SEQ ID No. 32) for gene therapy by DNA-binding repression-replacement of Rhodopsin, according to a preferred embodiment of the invention.
Figure 8:
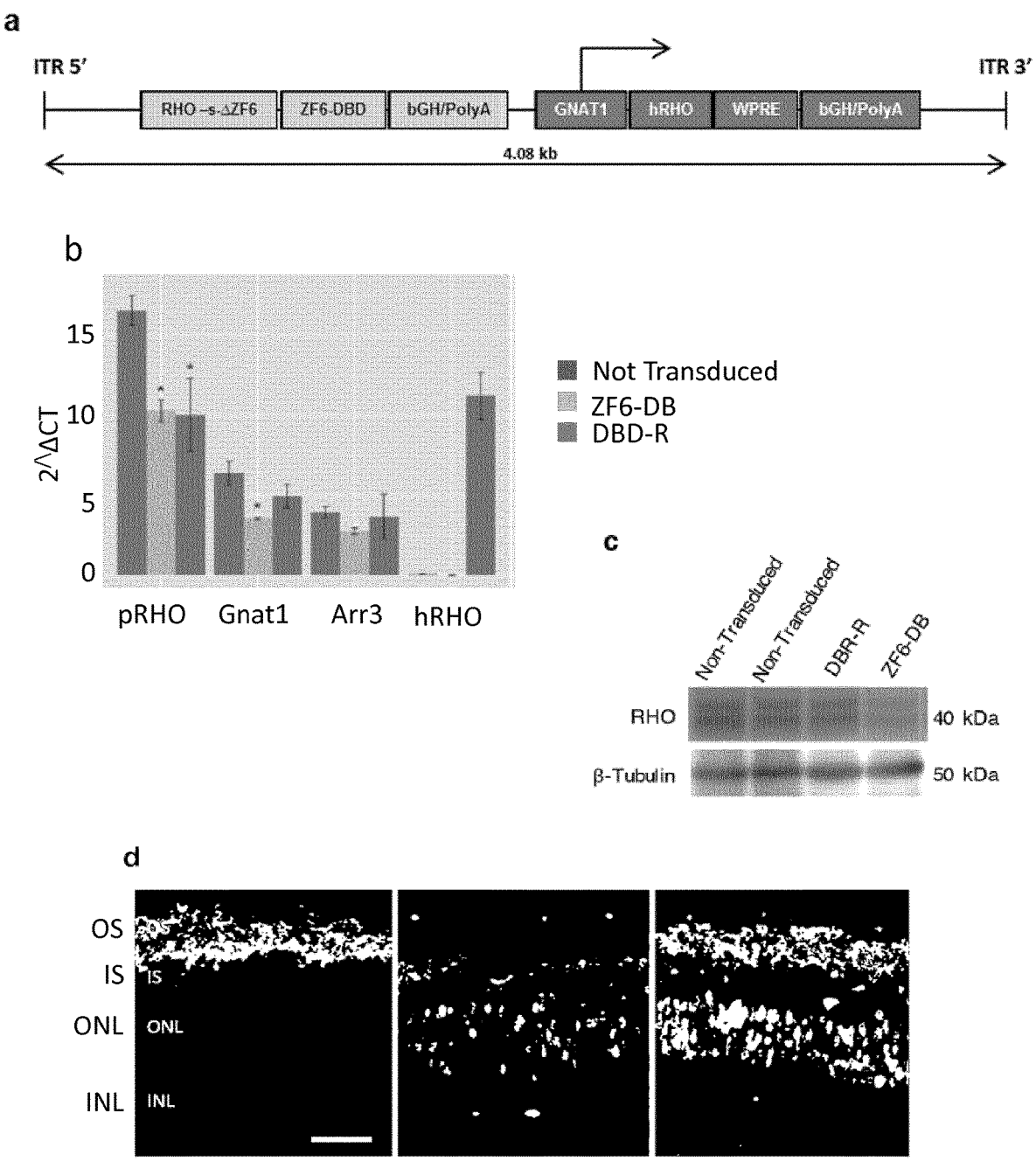
FIG. 8: DNA-binding repression-replacement of Rhodopsin in the porcine retina, according to a preferred embodiment of the invention: (a) DBR-R construct features, including the two expression cassettes: RHO-s-ΔZF6-ZF6-DBD cassette encoding for the DNA-binding repressor ZF6-DBD under the control of hRHO-s-ΔZF6 promoter, for repression of endogenous porcine Rhodopsin (pRho) and GNAT1-hRHO cassette encoding for hRHO under the control of hGNAT1 promoter, for replacement of hRHO. The size (kb) of the construct is indicated as a bar. (b) qReal Time PCR, mRNA levels (2^-ΔCT) 2 months after vector delivery of either AAV8-CMV-ZF6-DBD (ZF6-DB bars) or DBD-R (DBR-R bars), by AAV8 delivery, and non-transduced controls (non-transduced bars). pRho, porcine Rhodopsin; Gnat1, Guanine Nucleotide Binding Protein1; Arr3, Arrestin 3; hRHO, human Rhodopsin. The result is representative of two independent experiments. Error bars, means +/-s.e.m. n=; *p<0.05, p<0.01, *p<0.001; two-tailed Student's t test. (c) Western blot analysis on the retinas shown in (d). (d) Immunofluorescence double staining with Rho (green) and HA-ZF6-DBD (red) antibodies. Left panel, non-transduced control retina; middle panel, AAV8-CMV-ZF6-DBD treated retina; right panel, DBR-R treated retina, according to a preferred embodiment of the invention. OS, outer segment; IS, inner segment; ONL, outer nuclear layer; INL, inner nuclear layer; scale bar, 100 μm.

Two expression cassettes have been enclosed into a single vector (DNA-binding repression and replacement vector, DBR-R, SEQ ID NO 32; FIGS. 7 map of DBD-R vector and 8(a) expression cassette in DBD-R vector), according to a preferred embodiment of the invention, to warrant simultaneous photoreceptor transduction of both ZF6-DBD and hRHO (FIG. 8d). In order to achieve highly differential expression required for balanced simultaneous Rho repression and replacement by hRHO, the vector dose and promoter strength can be advantageously modulated.

Figure 6:
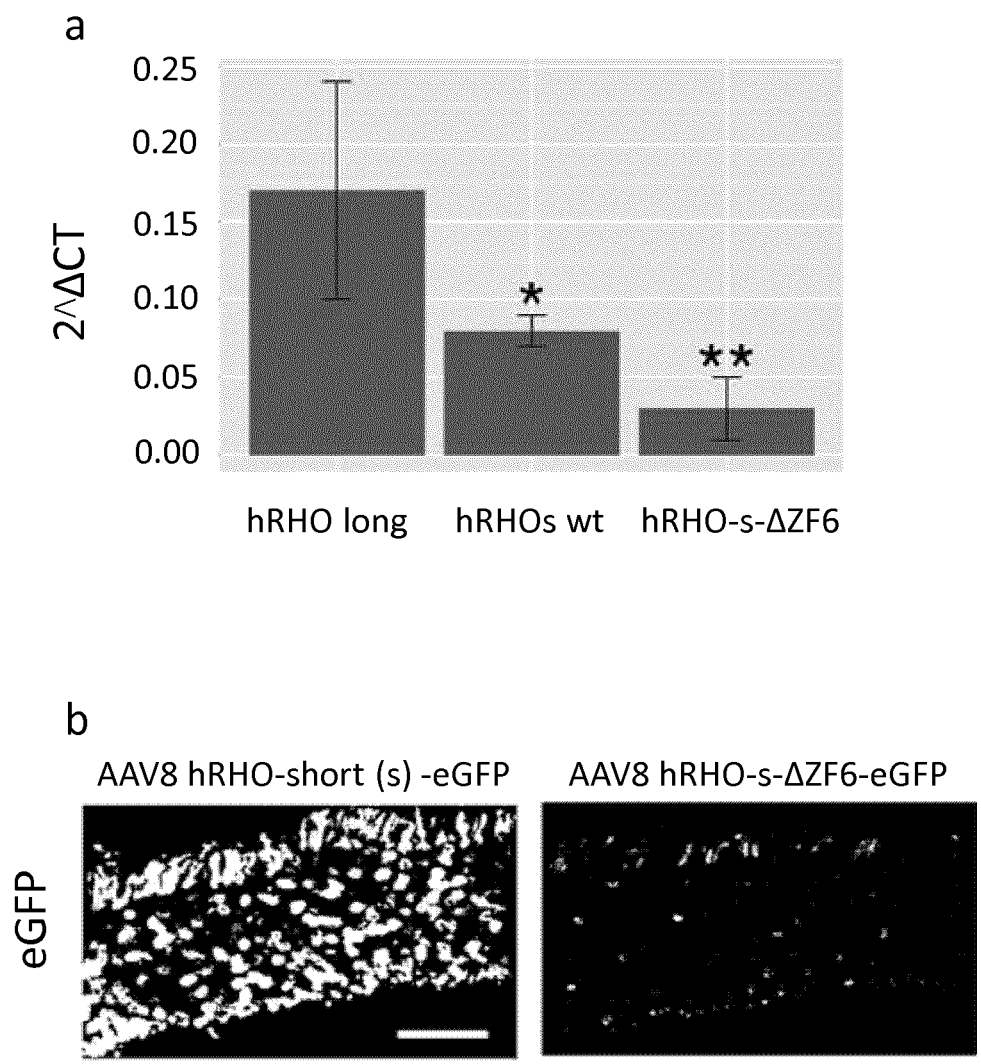
FIG. 6: Strength and tissue specificity of different promoters in murine retina: (a) eGFP mRNA levels by qReal Time PCR (2^-ΔCT) on the adult murine retina 15 days after AAV8-mediated delivery of vectors expressing eGFP under control of either full length hRHO wt promoter (hRHO long; SEQ ID NO 51) hRHO short wt promoter (hRHO short-eGFP) or hRHO short ΔZF6 promoter (hRHO-s-ΔZF6-eGFP), subretinally administered at a dose of 1×10$^9$ gc. AAV8-hRHO-s-ΔZF6-eGFP injection, according to a preferred embodiment of the invention, resulted in decreased expression of eGFP (about 10 fold) compared with AAV8-hRHO long injection. Error bars, means +/-s.e.m. n=; *p<0.05, **p<0.01; two-tailed Student's t test. (b) Histology demonstrating maintenance of rod-specific expression of eGFP driven by hRHO-s-ΔZF6 promoter (delivery by injection of AAV8-RHOΔZF6-eGFP). Scale bar, 50 μm.

It is noted that hRHO-s-ΔZF6 promoter-driven expression of eGFP, according to a preferred embodiment of the invention is strongly decreased compared to expression driven by wt RHO short promoter (hRHO short), or even more by hRHO long promoter; however, rod-specificity is kept with promoters of the invention (FIG. 6).

Figure 9:
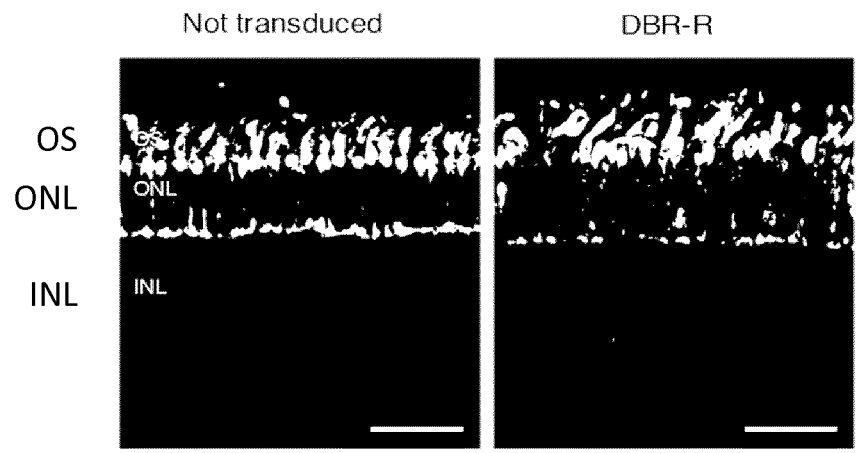
FIG. 9: Cone morphological integrity after DBR-R construct sub-retinal delivery. Rod-specific expression of DBR-R 2 month after vector delivery. Immunofluorescence double staining with human cone Arrestin 3 (hCAR; green) and HA-ZF6-DBD (red) antibodies show rod specific transduction. Left panel, non-transduced control retina; right panel, DBR-R treated retina. OS, outer segment; IS, inner segment; ONL, outer nuclear layer; IN L, inner nuclear layer. Scale bar, 50 μm.
Figure 10:
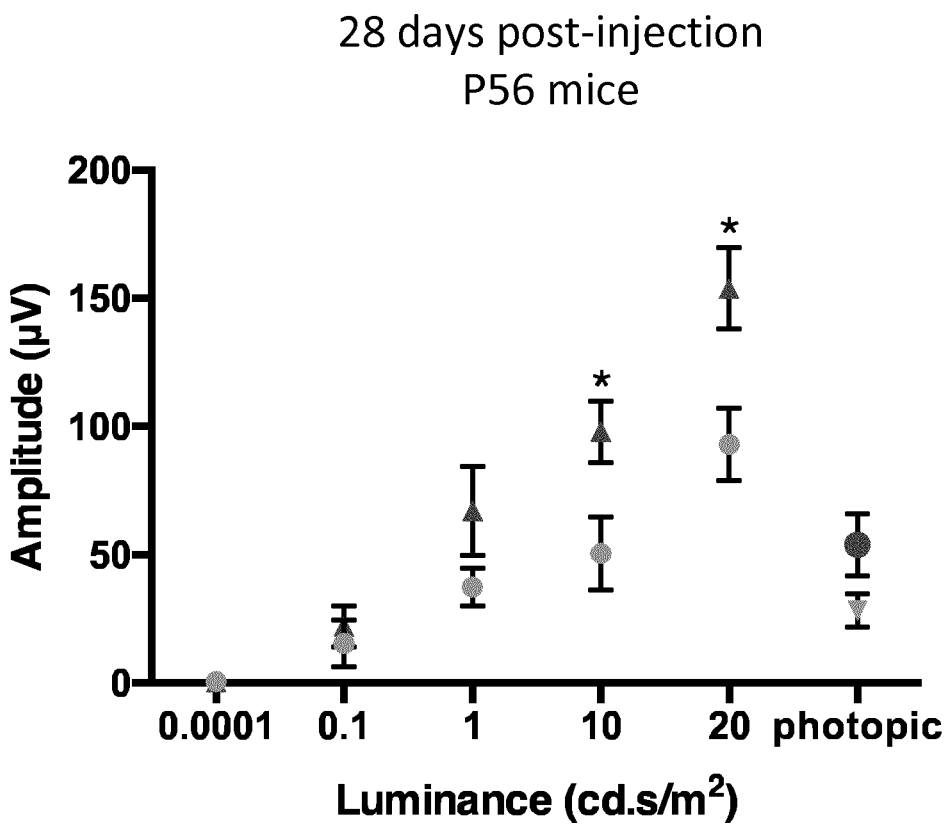
FIG. 10: Delivery of AAV2/8-hRHO-s-ΔZF6-ZF6 DBD viral vector into the retina of a mouse model of ADRP (P347S$^{+/-}$ mouse) resulting in preservation of the photoreceptor function (ERG analysis). P347S$^{+/-}$ mice 4 weeks old were injected with AAV 2/8-hRHOΔZF6-ZF6DBD (dose 7, 5×10$^9$ gc) and ERG analysis was performed 28 days post-injection.

In the instant example, a dose of $1\times10^{12}$ gc of DBR-R vector was administered to porcine retina by AAV8 delivery (AAV8-RHOA-ZF6-DBD-GNAT1-hRHO viral vector, DBD-R in FIGS. 8b, 8c and FIG. 9). The vector dose used of $1\times10^{12}$ gc was sufficient to produce Rho replacement by the GNAT1-hRHO cassette. However, the ZF6-DBD repressor at $1\times10^{12}$ gc would had been overexpressed, beyond the levels showed necessary to silence endogenous porcine Rho (AAV8-CMV-ZF6-DBD at $1\times10^{10}$ gc viral vector, ZF6-DB in FIGS. 8b and 8c). Therefore, the DBD under the hRHO-s-ΔZF6 promoter (SEQ ID No. 23), whose expression is strongly decreased compared to expression driven by wt hRHO promoter (SEQ ID No. 1), was advantageously used. As control, the contralateral eye received a vector comprising the sole ZF6-DBD repressor under the control of CMV promoter (AAV8-CMV-ZF6-DBD at $1\times10^{10}$ gc viral vector, ZF6-DB in FIGS. 8b and 8c). AAV8-CMV-eGFP was co-administrated to label the transduced areas.

Administration of the DBR-R vector resulted in concomitant rod-specific transcriptional repression of the porcine Rho (35%) and in balanced replacement with the exogenous hRHO (45%), as assessed by transcripts levels, protein expression and integrity of photoreceptor outer segments (FIG. 8b-d and FIG. 9).

The use of the strong ubiquitous CMV promoter led to a robust Rho repression but an uneven expression. In contrast, the use of hRHO-s-ΔZF6 promoter (SEQ ID No. 23), according to a preferred embodiment of the invention allowed the specific expression of the repressor ZF6-DB to rods, combined to an even (uniformly distributed) ZF6-DB expression, and similar Rho repression levels compared to the use of an unmodified promoter (such as the CMV promoter), but notably avoiding potential side effect due to extra-rods expression such as in cone cells (see FIG. 9).

The silencing and replacement approach demonstrated in vivo that the use of a rod specific promoter according to the invention enables fine regulation of levels of expression of the downstream gene. To ensure high and rod-specific hRHO replacement, a high vector dose was used and hRHO was cloned under the control of human GNAT1 promoter elements.

At the same time, to decrease ZF6-DBD expression levels at the high vector dose used, achieving Rho repression, still keeping rod-specificity, hRHO-s-ΔZF6 promoter (SEQ ID No. 23) was advantageously used (FIG. 8a).

The use of a rod specific promoter according to the invention in a single vector further comprising a second gene under a different promoter allows differential expression levels of two (or more) genes (e.g. in the instant example 36 fold range between hGNAT1 and hRHO-s-ΔZF6 promoters), while maintaining rod photoreceptor-specificity.

Furthermore the short length of hRHO-s-ΔZF6 promoter gives the advantage of generating constructs with two or more expression cassettes avoiding size limitations.

Example 3

In Vivo Testing in Gene Therapy Method of RHO Transcriptional Silencing

Subretinal injection of a viral vector (AAV2/8-hRHO-s-ΔZF6-ZF6DBD) comprising transcriptional repressor ZF6-DBD, under the control of a promoter according to the invention (Promoter hRHO-s-ΔZF6) into the retina of a mouse model of ADRP (P347S$^{+/-}$ mouse, n=6) results in an improvement of retinal function 28 days after injection, indicated by a statistically significant increase in b-wave ERG amplitude (P<0.05), compared to P347S$^{+/-}$ untreated mice (N=8). The instant example demonstrates that promoters according to the invention, allowing regulated transcription of can be advantageously and efficiently used in gene therapy for the treatment of a retinal diseases, since they provide cell-specific expression of a transgene at controlled levels.

Materials and Methods

| Sequences |
|---|
| Nucleotide sequence of hRHO short promoter wild-type (SEQ ID No. 1) |
| Nucleotide sequence of substituted fragment in Prom A (SEQ ID NO. 2) |
| Nucleotide sequence of substituted fragment in Prom B (SEQ ID NO. 3) |
| Nucleotide sequence of substituted fragment in Prom C (SEQ ID NO. 4) |
| Nucleotide sequence of substituted fragment in Prom D (SEQ ID NO. 5) |
| Nucleotide sequence of substituted fragment in Prom E (SEQ ID NO. 6) |
| Nucleotide sequence of substituted fragment in Prom F (SEQ ID NO. 7) |
| Nucleotide sequence of substituted fragment in Prom G (SEQ ID NO. 8) |
| Nucleotide sequence of substituted fragment in Prom H (SEQ ID NO. 9) |
| Nucleotide sequence of substituted fragment in Prom I (SEQ ID NO. 10) |
| Nucleotide sequence of substituted fragment in Prom L (SEQ ID NO. 11) |
| Nucleotide sequence of substituted fragment in Prom hRHO-s-ΔZF6 (SEQ ID NO. 12) |
| Nucleotide sequence of Prom A (SEQ ID No. 13) |
| Nucleotide sequence of Prom B (SEQ ID No. 14) |
| Nucleotide sequence of Prom C (SEQ ID No. 15) |
| Nucleotide sequence of Prom D (SEQ ID No. 16) |
| Nucleotide sequence of Prom E (SEQ ID No. 17) |
| Nucleotide sequence of Prom F (SEQ ID No. 18) |
| Nucleotide sequence of Prom G (SEQ ID No. 19) |
| Nucleotide sequence of Prom H (SEQ ID No. 20) |
| Nucleotide sequence of Prom I (SEQ ID No. 21) |
| Nucleotide sequence of Prom L (SEQ ID No. 22) |
| Nucleotide sequence of Prom hRHO-s-ΔZF6 (SEQ ID No. 23) |
| Nucleotide sequence of ZF6-DBD (SEQ ID No. 24) |
| Protein Sequence of ZF6-DBD (SEQ ID No. 25) |
| Nucleotide sequence of ZF2 (SEQ ID No. 26) |
| Proteic sequence of ZF2 (SEQ ID No. 27) |
| Nucleotide sequence of TAL01 (SEQ ID No. 28) |
| Proteic Sequence of TAL01 (SEQ ID No. 29) |
| Nucleotide sequence of TAL02 (SEQ ID No. 30) |
| Proteic Sequence of TAL02 (SEQ ID No. 31) |
| Nucleotide sequence of DBD-R (SEQ ID No. 32) Agcgcccaatacgcaaaccgcctctccccgcgcgttggccgattcattaatgcagctggcacgacaggtttcccga ctggaaagcgggcagtgagcgcaacgcaattaatgtgagttagctcactcattaggcaccccaggctttacacttt atgcttccggctcgtatgttgtgtggaattgtgagcggataacaatttcacacaggaaacagctatgaccatgatt acgccagatttaattaaggctgcgcgctcgctcgctcactgaggccgcccgggcaaagcccgggcgtcgggcgacc |

| Sequences |
| --- |
| tttggtcgcccggcctcagtgagcgagcgagcgcgcagagagggagtggccaactccatcactaggggttccttgt |
| agttaatgattaacccgccatgctacttatctacgtagccatgctctaggaagatcggaattcgcccttaaGCTAG |
| CTcctcctagtgtcaccttggcccctcttagaagccaattaggccctcagtttctgcagcggggattaatatgatt |
| ataaaatctcccaaatgctaattcaaccaaaagcttaaaaaaaggaagtcactttataaaaatctaaaaaaatcaa |
| aacccagagtcatccagctggaaccctgagtggctgagctcaggccttcgcagcattcttgggtaaaaacaaccac |
| gggtcagccacaagggccacagccCAATTGAtgatcgatctggaacctggcgaaaaaccgtataagtgcccagaat |
| gcggcaagtcttttttcccagtctggccacctgacggaacatcagcgcactcacaccggcgagaaaccatataaatg |
| tccggagtgcggcaagagctttagccagaatagcaccctgaccgaacatcagcgtacgcacacgggtgaaaagcca |
| tataaatgccctgagtgcggcaaatcctttagcacctctggccatctggtccgtcaccagcgcacccaccagaata |
| agaagggcggttctggtgacggtaaaaagaaacagcacgcctgtccagagtgtggcaaatcttttcccgtgaaga |
| caacctgcacactcaccagcgcactcatactggcgagaaaccttacaagtgtccggaatgtggtaagagcttctcc |
| acttccggccatctggttcgtcaccagcgcacgcacaccggcgaaaaaccatacaagtgcccggaatgcggcaaat |
| cattctcccgtagcgacaaactggttcgtcaccaacgtacgcataccggtaaaaagacttcctctagatacccgta |
| cgacgttccagactatgcatcttgaCATATGGcctcgactgtgccttctagttgccagccatctgttgtttgcccc |
| tccccgtgccttccttgaccctggaaggtgccactcccactgtcctttcctaataaaatgaggaaattgcatcgc |
| attgtctgagtaggtgtcattctattctgggggtggggtggggcaggacagcaaggggggaggattgggaagacaa |
| tagcaggcatgctggggaACTAGTgtagttaatgattaacccgccatgctacttatctacgtagccatgctctag |
| gaagatcggaattcgcccttaaGTTACGCTAGCtccctgcaggtcataaaatcccagtccagagtcaccagcccctt |
| cttaaccacttcctactgtgtgacccttcagcctttacttcctcatcagtaaaatgaggctgatgatatgggcat |
| ccatactccagggccagtgtgagcttacaacaagataaggagtggtgctgagcctggtgccgggcaggcagcaggc |
| atgtttctcccaattatgccctctcactgccagccccacctccattgtcctcaccccagggctcaaggttctgcc |
| ttcccctttctcagccctgaccctactgaacatgtctccccactccaggcagtgccagggcctctcctggagggt |
| tgcggggacagaaggacagccggagtgcagagtcagcggttgagggattggggctatgccagcTAatCCgaagggt |
| tgggggggctgagctggattcacctgtccttgtctctgattggctcttggacacccctagccccaaatcccacta |
| agcagcccaccagggattgcacaggtccgtagagagccagTTGATTGCAGGTCCTCCTGGGGCCAGAAGGGTGCC |
| TGGGAGGCCAGGTTCTGGGGATCCCCTCCATCCAGAAGAACCACCTGCTCACTCTGTCCCTTCGCCTGCTGCTGGG |
| ACCGCGGCCGCATGAATGGCACAGAAGGCCCTAACTTCTACGTGCCCTTCTCCAATGCGACGGGTGTGGTACGCAG |
| CCCCTTCGAGTACCCACAGTACTACCTGGCTGAGCCATGGCAGTTCTCCATGCTGGCCGCCTACATGTTTCTGCTG |
| ATCGTGCTGGGCTTCCCCATCAACTTCCTCACGCTCTACGTCACCGTCCAGCACAAGAAGCTGCGCACGCCTCTCA |
| ACTACATCCTGCTCAACCTAGCCGTGGCTGACCTCTTCATGGTCCTAGGTGGCTTCACCAGCACCCTCTACACCTC |
| TCTGCATGGATACTTCGTCTTCGGGCCCACAGGATGCAATTTGGAGGGCTTCTTTGCCACCCTGGGCGGTGAAATT |
| GCCCTGTGGTCCTTGGTGGTCCTGGCCATCGAGCGGTACGTGGTGGTGTGTAAGCCCATGAGCAACTTCCGCTTCG |
| GGGAGAACCATGCCATCATGGGCGTTGCCTTCACCTGGGTCATGGCGCTGGCCTGCGCCGCACCCCCACTCGCCGG |
| CTGGTCCAGGTACATCCCCGAGGGCCTGCAGTGCTCGTGTGGAATCGACTACTACACGCTCAAGCCGGAGGTCAAC |
| AACGAGTCTTTTGTCATCTACATGTTCGTGGTCCACTTCACCATCCCCATGATTATCATCTTTTTCTGCTATGGGC |
| AGCTCGTCTTCACCGTCAAGGAGGCCGCTGCCCAGCAGCAGGAGTCAGCCACCACACAGAAGGCAGAGAAGGAGGT |
| CACCCGCATGGTCATCATCATGGTCATCGCTTTCCTGATCTGCTGGGTGCCCTACGCCAGCGTGGCATTCTACATC |
| TTCACCCACCAGGGCTCCAACTTCGGTCCCATCTTCATGACCATCCCAGCGTTCTTTGCCAAGAGCGCCGCCATCT |
| ACAACCCTGTCATCTATATCATGATGAACAAGCAGTTCCGGAACTGCATGCTCACCACCATCTGCTGCGGCAAGAA |

| Sequences |
| --- |
| <u>CCCACTGGGTGACGATGAGGCCTCTGCTACCGTGTCCAAGACGGAGACGAGCCAGGTGGCCCCGGCCTAA</u>Aagctt ggatccaatcaacctctggattacaaaatttgtgaaagattgactggtattcttaactatgttgctccttttacgc tatgtggatacgctgctttaatgcctttgtatcatgctattgcttcccgtatggctttcattttctcctccttgta taaatcctggttgctgtctctttatgaggagttgtggcccgttgtcaggcaacgtggcgtggtgtgcactgtgttt gctgacgcaaccccactggttggggcattgccaccacctgtcagctcctttccgggactttcgctttccccctcc ctattgccacggcggaactcatcgccgcctgccttgccgctgctggacaggggctcggctgttgggcactgacaa ttccgtggtgttgtcggggaagctgacgtcctttccatggctgctcgcctgtgttgccacctggattctgcgcggg acgtccttctgctacgtcccttcggccctcaatccagcggaccttccttcccgcggcctgctgccggctctgcggc ctcttccgcgtcttcgagatctgcctcgactgtgccttctagttgccagccatctgttgtttgccctccccgtg ccttccttgaccctggaaggtgccactcccactgtcctttcctaataaaatgaggaaattgcatcgcattgtctga gtaggtgtcattctattctgggggtggggtggggcaggacagcaaggggggaggattgggaagacaatagcaggca tgctggggactcgagttaagggcgaattcccgattaggatcttcctagagcatggctacgtagataagtagcatgg cgggttaatcattaactacaaggaaccctagtgatggagttggccactccctctctgcgcgctcgctcgctcact gaggccgggcgaccaaaggtcgcccgacgcccgggctttgcccgggcggcctcagtgagcgagcgagcgcgcagcc ttaattaacctaattcactggccgtcgttttacaacgtcgtgactgggaaaaccctggcgttacccaacttaatcg ccttgcagcacatccccctttcgccagctggcgtaatagcgaagaggcccgcaccgatcgcccttcccaacagttg cgcagcctgaatggcgaatgggacgcgccctgtagcggcgcattaagcgcggcgggtgtggtggttacgcgcagcg tgaccgctacacttgccagcgccctagcgcccgctcctttcgctttcttcccttcctttctcgccacgttcgccgg ctttccccgtcaagctctaaatcgggggctccctttagggttccgatttagtgctttacggcacctcgaccccaaa aaacttgattagggtgatggttcacgtagtgggccatcgccccgatagacggtttttcgccctttgacgctggagt tcacgttcctcaatagtggactcttgttccaaactggaacaacactcaaccctatctcggtctattcttttgattt ataagggattttccgatttcggcctattggttaaaaaatgagctgatttaacaaaaatttaacgcgaattttaac aaaatattaacgtttataatttcaggtggcatctttcggggaaatgtgcgcggaaccccctatttgttattttttct aaatacattcaaatatgtatccgctcatgagacaataaccctgataaatgcttcaataatattgaaaaaggaagag tatgagtattcaacatttccgtgtcgcccttattccctttttttgcggcattttgccttcctgttttttgctcaccca gaaacgctggtgaaagtaaaagatgctgaagatcagttgggtgcacgagtgggttacatcgaactggatctcaata gtggtaagatccttgagagttttcgccccgaagaacgttttccaatgatgagcacttttaaagttctgctatgtgg cgcggtattatcccgtattgacgccgggcaagagcaactcggtcgccgcatacactattctcagaatgacttggtt gagtactcaccagtcacagaaaagcatcttacggatggcatgacagtaagagaattatgcagtgctgccataacca tgagtgataacactgcggccaacttacttctgacaacgatcggaggaccgaaggagctaaccgcttttttgcacaa catggggatcatgtaactcgccttgatcgttgggaaccggagctgaatgaagccataccaaacgacgagcgtgac accacgatgcctgtagtaatggtaacaacgttgcgcaaactattaactggcgaactacttactctagcttcccggc aacaattaatagactggatggaggcggataaagttgcaggaccacttctgcgctcggcccttccggctggctggtt tattgctgataaatctggagccggtgagcgtgggtctcgcggtatcattgcagcactggggccagatggtaagccc tcccgtatcgtagttatctacacgacggggagtcaggcaactatggatgaacgaaatagacagatcgctgagatag gtgcctcactgattaagcattggtaactgtcagaccaagtttactcatatatactttagattgatttaaaacttca tttttaatttaaaaggatctaggtgaagatcctttttgataatctcatgaccaaaatcccttaacgtgagttttcg ttccactgagcgtcagacccgtagaaaagatcaaaggatcttcttgagatcctttttttctgcgcgtaatctgct |

| Sequences |
|---|
| gcttgcaaacaaaaaaaccaccgctaccagcggtggtttgtttgccggatcaagagctaccaactcttttttccgaa |
| ggtaactggcttcagcagagcgcagataccaaatactgtccttctagtgtagccgtagttaggccaccacttcaag |
| aactctgtagcaccgcctacatacctcgctctgctaatcctgttaccagtggctgctgccagtggcgataagtcgt |
| gtcttaccgggttggactcaagacgatagttaccggataaggcgcagcggtcgggctgaacggggggttcgtgcac |
| acagcccagcttggagcgaacgacctacaccgaactgagatacctacagcgtgagctatgagaaagcgccacgctt |
| cccgaagggagaaaggcggacaggtatccggtaagcggcagggtcggaacaggagagcgcacgagggagcttccag |
| ggggaaacgcctggtatctttatagtcctgtcgggtttcgccacctctgacttgagcgtcgattttgtgatgctc |
| gtcagggggcggagcctatggaaaaacgccagcaacgcggccttttacggttcctggccttttgctgcggtttt |
| gctcacatgttctttcctgcgttatcccctgattctgtggataaccgtattaccgcctttgagtgagctgataccg |
| ctcgccgcagccgaacgaccgagcgcagcgagtcagtgagcgaggaagcggaag |

Features costrutto:
5'-ITR:[248:377-CW]

3'-ITR:[4201:4330-CW]

additional\AAV\sequences:[4155:4200-CW]

WPRE:[3351:3892-CW]

BGH\pA:[3899:4113-CW]

Rev\Ori\NheI:[6744:6769-CW]

Fw\NheI\Ori:[5951:5974-CW]

hGNAT1 + 5'UTR:[1630:2283-CW]

hRHO_CDS:[2292:3338-CW]

hRHO_small_(DEvo):[458:708-CW]

ZF6-DBD:[715:1317-CW]

BGH\pA:[1324:1538-CW]

M13-fwd:[4366:4349-CCW]

M13-rev:[205:225-CW]

ColE1 origin:[6103:6731-CW]

LacZ alpha:[4437:4505-CW]

LacO:[177:199-CW]

Amp prom:[5024:5052-CW]

lac:[143:172-CW]

HA tag:[1285:1311-CW]

FactorXa site:[3833:3822-CCW]

RHO proximal promoter target region 1 (SEQ ID No. 33)

RHO proximal promoter target region 2 (SEQ ID No. 34)

RHO proximal promoter target region 3 (SEQ ID No. 35)

RHO proximal promoter target region 4 (SEQ ID No. 36)

RHO proximal promoter target region 5 (SEQ ID No. 37)

RHO proximal promoter target region 6 (SEQ ID No. 38)

RHO proximal promoter target region 7 (SEQ ID No. 39),

-continued

| Sequences |
|---|
| RHO proximal promoter target region 8 (SEQ ID No. 40) |
| RHO proximal promoter target region 9 (SEQ ID No. 41) |
| RHO proximal promoter target region 10 (SEQ ID No 42) |
| Nucleotide sequence of ZF6-5F (also called ZF6-5) (SEQ ID No. 43) |
| Protein sequence of ZF6-5F (also called ZF6-5) (SEQ ID No. 44) |
| Nucleotide sequence of TAL7-DBD (SEQ ID No. 45) |
| Protein sequence of TAL7-DBD (SEQ ID No. 46) |
| Nucleotide sequence of TALRHO(02)DBD (SEQ ID No. 47) |
| Protein sequence of TALRHO02DBD (SEQ ID No. 48) |
| hRHO CDS (SEQ ID No. 49) |
| KRAB sequence (SEQ ID No. 50) |
| Nucleotide sequence of human rhodopsin promoter with its 5'UTR (SEQ ID No. 51) |
| Nucleotide sequence of the human transducin 1 (GNAT1) promoter (SEQ ID No. 52) |

Plasmid Construction.

The human rhodopsin short promoter (hRHO-short-(s), 164 bp from the transcription starting site (TSS)+5'UTR), was generated by gene synthesis of Eurofins MWG® and cloned in pAAV2.1 using NheI and NotI restriction enzymes. All modified promoters (prom A, prom B, prom C, prom D, prom E, prom F, hRHO-s-ΔZF6, prom G, prom H, prom I, prom L) were generated by gene synthesis of Eurofins MWG® and cloned in pAAV2.1 using NheI and NotI restriction enzymes.

AAV Vector Preparations.

AAV vectors were produced by the TIGEM AAV Vector Core, by triple transfection of HEK293 cells followed by two rounds of CsCl2 purification. For each viral preparation, physical titers [genome copies (GC)/mL] were determined by averaging the titer achieved by dot-blot analysis and by PCR quantification using TaqMan (Applied Biosystems, Carlsbad, Calif., USA).

Vector Administration and Animal Models.

All procedures were performed in accordance with institutional guidelines for animal research and all of the animal studies were approved by the inventors.

C57BL/6 mice (Charles Rivers Laboratories, Calco, Italy) were bred in the animal facility of the Biotechnology Centre of the Cardarelli Hospital (Naples, Italy).

P347S$^{+/+}$ animals (Mussolino et al., 2011a; Li et al., 1996) were bred in the animal facility of the Biotechnology Centre of the Cardarelli Hospital (Naples, Italy) with C57Bl/6 mice (Charles Rivers Laboratories, Calco, Italy), to obtain the P347S$^{+/-}$ mice.

Mice. Intraperitoneal injection of ketamine and medetomidine (100 mg/kg and 0.25 mg/kg respectively), then AAV vectors were delivered sub-retinally via a trans-scleral transchoroidal approach as described by Liang et al.

Eleven-week-old Large White (LW) female piglets were utilized. Pigs were fasted overnight leaving water ad libitum. The anesthetic and surgical procedures for pigs were previously described in Mussolino et al. AAV vectors were inoculated sub-retinally in the avascular nasal area of the posterior pole between the two main vascular arches, as performed in Mussolino et al. This retinal region is crossed by a streak-like region that extends from the nasal to the temporal edge parallel to the horizontal meridian, where cone density is high, reaching 20000 to 35000 cone cells mm2. Each viral vector was injected in a total volume of 100 μl, resulting in the formation of a subretinal bleb with a typical 'dome-shaped' retinal detachment, with a size corresponding to 5 optical discs.

qReal Time PCR.

RNAs from tissues were isolated using RNAeasy Mini Kit (Qiagen), according to the manufacturer protocol. cDNA was amplified from 1 μg isolated RNA using QuantiTect Reverse Transcription Kit (Qiagen), as indicated in the manufacturer instructions.

The PCRs with cDNA were carried out in a total volume of 20 μl, using 10 μl LightCycler 480 SYBR Green I Master Mix (Roche) and 400 nM primers under the following conditions: pre-Incubation, 50° C. for 5 min, cycling: 45 cycles of 95° C. for 10 s, 60° C. for 20 s and 72° C. for 20 s. Each sample was analysed in duplicate in two-independent experiments. Transcript levels of murine retinae were measured by real-time PCR using the LightCycler 480 (Roche) and the following primers: eGFP_forward (ACGTAAACGGCCACAAGTTC (SEQ ID No. 53)) and eGFP_reverse (AAGTCGTGCTGCTTCATGTG, (SEQ ID No. 54)). All of the reactions were standardized against murine Actβ and murine Gapdh using the following primers: Act_forward (CAAGATCATTGCTCCTCCTGA, (SEQ ID No. 55)) and Act_reverse (CATCGTACTCCTGC-TTGCTGA, (SEQ ID No. 56)), Gapdh_forward (GTCGGTGTGAACGGATTTG, (SEQ ID No. 57)) and Gapdh_reverse (CAATGAAGGGGTCGTTGATG, (SEQ ID No. 58)).

Histological Analysis.

For morphological studies, the eyecups were harvested, fixed by immersion in 4% paraformaldehyde, and then embedded in OCT (KalteK). For each eye, 150 to 200 serial sections (5-μm thick) were cut along the horizontal plane; the sections were progressively distributed on 10 glass slides so that each slide contained 15 to 20 sections representative of the whole eye at different levels. Slides were coverslipped with Vectashield containing DAPI (4',6-diamidino-2-phenylindole; Vector laboratories, Burlingame, Calif., USA) to stain cells nuclei and retinal histology was analyzed a Leica Fluorescence Microscope System (Leica Microsystems GmbH, Wetzlar, Germany).

Electrophysiological Testing.

Mice were dark reared for three hours and anesthetized. Flash electroretinograms (ERGs) were evoked by 10-ms light flashes generated through a Ganzfeld stimulator (CSO, Costruzione Strumenti Oftalmici, Florence, Italy) and registered as previously described. ERGs and b-wave thresholds were assessed using the following protocol. Eyes were stimulated with light flashes increasing from −5.2 to +1.3 log cd*s/m2 (which correspond to 1×10-5.2 to 20.0 cd*s/m2) in scotopic conditions. The log unit interval between stimuli was 0.3 log from −5.4 to 0.0 log cd*s/m2, and 0.6 log from 0.0 to +1.3 log cd*s/m2. For ERG analysis in scotopic conditions the responses evoked by 11 stimuli (from −4 to +1.3 log cd*s/m2) with an interval of 0.6 log unit were considered. To minimize the noise, three ERG responses were averaged at each 0.6 log unit stimulus from −4 to 0.0 log cd*s/m2 while one ERG response was considered for higher (0.0−+1.3 log cd*s/m2) stimuli. The time interval between stimuli was 10 seconds from −5.4 to 0.7 log cd*s/m2, 30 sec from 0.7 to +1 log cd*s/m2, or 120 seconds from +1 to +1.3 log cd*s/m2. a- and b-waves amplitudes recorded in scotopic conditions were plotted as a function of increasing light intensity (from −4 to +1.3 log cd*s/m2). The photopic ERG was recorded after the scotopic session by stimulating the eye with ten 10 ms flashes of 20.0 cd*s/m2 over a constant background illumination of 50 cd/m2.

Data Management.

All the analyses, except for the reads quality filtering, alignment and expression estimates, were performed in the R statistical environment (v.3.2.0) (35, 36). Plots were generated with ggplot2 R/Bioconductor package (v.1.0.1).

Statistical analyses. Data are presented as mean±Error bars indicate standard error mean (SEM).

Statistical significance was computed using the Student's two-sided t-test and p-values <0.05 were considered significant. No statistical methods were used to estimate the sample size and no animals were excluded.

REFERENCES

1. Joseph C Corbo, Expert Opinion on Biological Therapy 2008, 8(5), 599-608
2. Papadakis E D, et al. Current Gene Therapy, 2004, 4, 89-113
3. Li T, Snyder W K, Olsson J E, Dryja T P. Proc Natl Acad Sci USA. 1996; 93(24):14176-81
4. Li L. et al. Mol. Plant 6, 1318-1330; 2013
5. Mussolino C, et al. EMBO Mol Med. 2011 March; 3(3):118-28
6. C Mussolino, et al. Gene Ther (2011) 18: 637-645
7. Liang F Q, Anand V, Maguire A M, Bennett J. Methods Mol Med. 2001; 47:125-39
8. Seipel K, Georgiev O, Schaffner W (1992) EMBO J 11: 4961-4968
9. Margolin J F, et al. Proc Natl Acad Sci USA. 1994 May 10; 91(10):4509-13

The invention claimed is:

1. A polynucleotide promoter or a variant thereof consisting of the sequence (SEQ ID No. 1)
TCCTCCTAGTGTCACCTTGGCCCCTCTTAGAAGCCAATTAGGCCCTCA

GTTTCTGCAGCGGGGATTAATATGATTATGAACACCCCCAATCTCCCA

GATGCTGATTCAGCCAGGAGCTTAGGAGGGGAGGTCACTTTATAAGG

GTCTGGGGGGTCAGAACCCAGAGTCATCCAGCTGGAGCCCTGAGTGG

CTGAGCTCAGGCCTTCGCAGCATTCTTGGGTGGGAGCAGCCACGGGTC

AGCCACAAGGGCCACAGCC wherein the fragment TGAACACCCCCAATCTCCCAGATGCT (sequence from nucleotide 77 to nucleotide 102 of SEQ ID NO. 1) is substituted with a sequence selected from the group consisting of:

a) (Prom A)
(SEQ ID NO. 2)
TGAACACCCCCAATCGATGCT;

b) (Prom B)
(SEQ ID NO. 3)
TGAACACCCCCAATCTCAACTCGTAG;

c) (Prom C)
(SEQ ID NO. 4)
TGAACACCCCCACGAGAAACTCTGCT;

d) (Prom D)
(SEQ ID NO. 5)
GTCCACACCCCACGAGAAACTCTGCT;

e) (Prom E)
(SEQ ID NO. 6)
TGAACACATGATATCTCCCAGATGCT;

f) (Prom F)
(SEQ ID NO. 7)
TGAACACATCTCCCAGATGCT;

g) (Prom G)
(SEQ ID NO. 8)
GTCCACACCCCAATCTCCCAGATGCT;

h) (Prom H)
(SEQ ID NO. 9)
CGACCGTATCGGGGTTAGGGAGTGCT;

i) (Prom I)
(SEQ ID NO. 10)
TCCCCCAATCTCCCAGATGCT;

j) (Prom L)
(SEQ ID NO. 11)
GAGGGATTGGTGCTATGCCAGCTGCT;

k) (hRHO-s-ΔZF6)
(SEQ ID NO. 12)
TGAAATCTCCCAGATGCT;

and l) a sequence having an identity of at least 90% with a sequence selected from the group consisting of SEQ ID NO. 2 to 11 and wherein the variant has at least 80% identity with any of SEQ ID NO. 13 to 22.

2. The polynucleotide or a variant thereof according to claim 1 wherein the fragment is substituted with a sequence selected from the group consisting of:

a) (Prom A)
(SEQ ID NO. 2)
TGAACACCCCCAATCGATGCT;

b) (Prom B)
(SEQ ID NO. 3)
TGAACACCCCCAATCTCAACTCGTAG;

c) (Prom C)
(SEQ ID NO. 4)
TGAACACCCCCACGAGAAACTCTGCT;

d) (Prom D)
(SEQ ID NO. 5)
GTCCACACCCCACGAGAAACTCTGCT;

e) (Prom E)
(SEQ ID NO. 6)
TGAACACATGATATCTCCCAGATGCT;

f) (Prom F)
(SEQ ID NO. 7)
TGAACACATCTCCCAGATGCT;

g) (Prom G)
(SEQ ID NO. 8)
GTCCACACCCCAATCTCCCAGATGCT;

and h) a sequence having an identity of at least 90% with a sequence selected from the group consisting of SEQ ID NO. 2 to 8.

and wherein said polynucleotide or a variant thereof has a promoter activity weaker than SEQ ID No. 1.

3. The polynucleotide or a variant thereof according to claim 1 wherein the fragment is substituted with a sequence selected from the group consisting of:

```
a) (Prom H)
                                    (SEQ ID NO. 9)
CGACCGTATCGGGGTTAGGGAGTGCT;

b) (Prom I)
                                    (SEQ ID NO. 10)
TCCCCCAATCTCCCAGATGCT;

c) (Prom L)
                                    (SEQ ID NO. 11)
GAGGGATTGGTGCTATGCCAGCTGCT;
```
and
  d) a sequence having an identity of at least 90% with a sequence selected from the group consisting of SEQ ID NO. 9 to 11 and wherein said polynucleotide or a variant thereof has a promoter activity stronger than SEQ ID No. 1.

4. The polynucleotide or a variant thereof according to claim 1 wherein said polynucleotide or a variant thereof shows a promoter activity in retina cells, photoreceptors, or rods.

5. A vector comprising the polynucleotide or a variant thereof according to claim 1.

6. The polynucleotide promoter or a variant thereof according to claim 1 wherein the fragment TGAACACCCCCAATCTCCCAGATGCT (sequence from nucleotide 77 to nucleotide 102 of SEQ ID NO. 1) is substituted with a sequence selected from the group consisting of:

```
a) (hRHO-s-ΔZF6)
                                    (SEQ ID NO. 12)
TGAAATCTCCCAGATGCT
```
and
  b) a sequence having an identity of at least 90% with sequence SEQ ID NO. 12.

7. A vector comprising a first expression cassette comprising the polynucleotide or a variant thereof according to claim 1 and a first transgene under the control of said polynucleotide.

8. The vector of claim 7, wherein said first transgene encodes for a transcriptional repressor.

9. The vector according to claim 8 wherein said transcriptional repressor is selected from the group consisting of: an antisense oligonucleotide, a siRNA, a shRNA or a miRNA, targeting a RHO transcript; an artificial transcription factor (ATF) comprising a DNA Binding domain coupled to one or more effector domains, targeting a sequence of the hRHO promoter; an isolated DNA Binding domain (DNA binding domain or DBD), and targeting a sequence of the hRHO promoter.

10. The vector according to claim 7, comprising a further expression cassette, said further expression cassette comprises a further promoter and a further transgene under control of said further promoter, optionally wherein said further promoter is a polynucleotide which is the same or it is different from the polynucleotide of the first expression cassette.

11. The vector according to claim 10 wherein the further transgene is a nucleotide sequence encoding a protein able to correct a retinal disease.

12. The vector according to claim 10 wherein the further promoter is a retina specific promoter, or a rod-specific promoter, optionally being the rhodopsin kinase (RHOK), the GNAT1 promoter, or GNAT1 promoter of sequence SEQ ID NO. 52.

13. The vector according to claim 10, wherein the further transgene is the coding sequence of a gene selected from the group consisting of: GUCY2D (locus name: LCA1), RPE65 (LCA2), SPATA7 (LCA3), AIPL1 (LCA4), LCA5 (LCA5), RPGRIP1 (LCA6), CRX (LCA7), CRB1 (LCA8), CEP290 (LCA10), IMPDH1 (LCA11), RD3 (LCA12), NMNAT1 (LCA9), LRAT (LCA14), TULP1 (LCA15), and RDH12 (LCA13), BEST1, CA4, RP17, CRX, FSCN2, RP30, GUCA1B, RP48, IMPDH1, RP10, KLHL7, RP42, NR2E3, NRL, RP27, ORP1, DCDC4A, RP1, PRPF3, RP18, PRPF31, PRPF6,rp60, PRPF8, PRPH2, RDS, RP7, RHO, ROM1, RP1, L1, RP63, RP9, RPE65, RP20, SEMA4A, RP35, MERTK, RP33, TOPORS, HK1, PRPF4, RDH12, LCA13, RP53, SNRNP200, ASCC3L1, BRR2, HECIC2, and RP33.

14. The vector according to claim 7 wherein the first expression cassette comprises SEQ ID No. 23 and SEQ ID No. 24.

15. The vector of claim 10 having sequence SEQ ID NO. 32 or having a sequence having an identity of at least 90% with SEQ ID NO. 32.

16. A vector system comprising:
  a) the vector according to claim 7; and
  b) a second vector containing the at least one further expression cassette.

17. The vector system according-to claim 16, wherein the vectors are viral vectors, optionally adeno virus vectors or adeno-associated virus (AAV) vectors.

18. The vector system according to claim 16, wherein the first and second vector are adeno-associated virus (AAV) vectors selected from the same or different AAV serotypes.

19. A host cell transformed with the vector of claim 5.

20. A pharmaceutical composition comprising the polynucleotide of claim 1.

21. A method for treating and/or preventing a retinal disease comprising administering to a subject in need thereof an effective amount of the polynucleotide or a variant thereof according to claim 1.

22. The method of claim 21, wherein the retinal disease is characterized by a retinal degeneration, or retinal disease is inherited.

23. The method of claim 21, wherein the retinal disease is selected from the group consisting of: retinitis pigmentosa (RP), Leber congenital amaurosis (LCA), rod-cone dystrophy and cone dystrophy.

24. The polynucleotide promoter or a variant thereof according to claim 1, wherein said promoter has a promoter activity at least 40% higher or at least 25% lower than the wild-type promoter of SEQ ID No. 1.

25. A vector comprising the polynucleotide or a variant thereof according to claim 6.

* * * * *

SEQUENCE LISTING

```
<160> NUMBER OF SEQ ID NOS: 58

<210> SEQ ID NO 1
<211> LENGTH: 259
<212> TYPE: DNA
<213> ORGANISM: Artificial Sequence
<220> FEATURE:
<223> OTHER INFORMATION: synthetic

<400> SEQUENCE: 1
tcctcctagt gtcaccttgg cccctcttag aagccaatta ggccctcagt ttctgcagcg      60
gggattaata tgattatgaa caccccccaat ctcccagatg ctgattcagc caggagctta     120 ggaggggag gtcactttat aagggtctgg ggggggtcaga acccagagtc atccagctgg     180
agccctgagt ggctgagctc aggccttcgc agcattcttg ggtgggagca gccacgggtc     240
agccacaagg gccacagcc                                                   259

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
tgaacacccc caatcgatgc t                                                21

<210> SEQ ID NO 3
<211> LENGTH: 26
<212> TYPE: DNA
<213> ORGANISM: Artificial Sequence
<220> FEATURE:
<223> OTHER INFORMATION: synthetic
```

<400> SEQUENCE: 3
tgaacacccc caatctcaac tcgtag					26

<210> SEQ ID NO 4
<211> LENGTH: 26
<212> TYPE: DNA
<213> ORGANISM: Artificial Sequence
<220> FEATURE:
<223> OTHER INFORMATION: synthetic

<400> SEQUENCE: 4
tgaacacccc cacgagaaac tctgct					26

<210> SEQ ID NO 5
<211> LENGTH: 26
<212> TYPE: DNA
<213> ORGANISM: Artificial Sequence
<220> FEATURE:
<223> OTHER INFORMATION: synthetic

<400> SEQUENCE: 5
gtccacaccc cacgagaaac tctgct					26

<210> SEQ ID NO 6
<211> LENGTH: 26
<212> TYPE: DNA
<213> ORGANISM: Artificial Sequence
<220> FEATURE:
<223> OTHER INFORMATION: synthetic

<400> SEQUENCE: 6
tgaacacatg atatctccca gatgct					26

<210> SEQ ID NO 7
<211> LENGTH: 21
<212> TYPE: DNA
<213> ORGANISM: Artificial Sequence
<220> FEATURE:
<223> OTHER INFORMATION: synthetic

<400> SEQUENCE: 7
tgaacacatc tcccagatgc t						21

<210> SEQ ID NO 8
<211> LENGTH: 26
<212> TYPE: DNA
<213> ORGANISM: Artificial Sequence
<220> FEATURE:
<223> OTHER INFORMATION: synthetic

<400> SEQUENCE: 8
gtccacaccc caatctccca gatgct					26

<210> SEQ ID NO 9
<211> LENGTH: 26
<212> TYPE: DNA
<213> ORGANISM: Artificial Sequence
<220> FEATURE:
<223> OTHER INFORMATION: synthetic

<400> SEQUENCE: 9
cgaccgtatc ggggttaggg agtgct					26

<210> SEQ ID NO 10

```
<211> LENGTH: 21
<212> TYPE: DNA
<213> ORGANISM: Artificial Sequence
<220> FEATURE:
<223> OTHER INFORMATION: synthetic

<400> SEQUENCE: 10
tcccccaatc tcccagatgc t                                                  21

<210> SEQ ID NO 11
<211> LENGTH: 26
<212> TYPE: DNA
<213> ORGANISM: Artificial Sequence
<220> FEATURE:
<223> OTHER INFORMATION: synthetic

<400> SEQUENCE: 11
gagggattgg tgctatgcca gctgct                                             26

<210> SEQ ID NO 12
<211> LENGTH: 18
<212> TYPE: DNA
<213> ORGANISM: Artificial Sequence
<220> FEATURE:
<223> OTHER INFORMATION: synthetic

<400> SEQUENCE: 12
tgaaatctcc cagatgct                                                      18

<210> SEQ ID NO 13
<211> LENGTH: 254
<212> TYPE: DNA
<213> ORGANISM: Artificial Sequence
<220> FEATURE:
<223> OTHER INFORMATION: synthetic

<400> SEQUENCE: 13
tcctcctagt gtcaccttgg cccctcttag aagccaatta ggccctcagt ttctgcagcg        60
gggattaata tgattatgaa cacccccaat cgatgctgat tcagccagga gcttaggagg       120
gggaggtcac tttataaggg tctgggggggg tcagaaccca gagtcatcca gctggagccc      180
tgagtggctg agctcaggcc ttcgcagcat tcttgggtgg gagcagccac gggtcagcca      240
caagggccac agcc                                                        254

<210> SEQ ID NO 14
<211> LENGTH: 259
<212> TYPE: DNA
<213> ORGANISM: Artificial Sequence
<220> FEATURE:
<223> OTHER INFORMATION: synthetic

<400> SEQUENCE: 14
tcctcctagt gtcaccttgg cccctcttag aagccaatta ggccctcagt ttctgcagcg        60
gggattaata tgattatgaa cacccccaat ctcaactcgt aggattcagc caggagctta      120 ggaggggggag gtcactttat aagggtctgg ggggtcaga acccagagtc atccagctgg      180
agccctgagt ggctgagctc aggccttcgc agcattcttg ggtgggagca gccacgggtc      240
agccacaagg gccacagcc                                                   259

<210> SEQ ID NO 15
<211> LENGTH: 259
<212> TYPE: DNA
<213> ORGANISM: Artificial Sequence
```

<220> FEATURE:
<223> OTHER INFORMATION: synthetic

<400> SEQUENCE: 15

```
tcctcctagt gtcaccttgg cccctcttag aagccaatta ggccctcagt ttctgcagcg    60
gggattaata tgattatgaa cacccccacg agaaactctg ctgattcagc caggagctta   120
ggagggggag gtcactttat aagggtctgg ggggtcaga acccagagtc atccagctgg    180
agccctgagt ggctgagctc aggccttcgc agcattcttg ggtgggagca gccacgggtc   240
agccacaagg gccacagcc                                                259
```

<210> SEQ ID NO 16
<211> LENGTH: 259
<212> TYPE: DNA
<213> ORGANISM: Artificial Sequence
<220> FEATURE:
<223> OTHER INFORMATION: synthetic

<400> SEQUENCE: 16

```
tcctcctagt gtcaccttgg cccctcttag aagccaatta ggccctcagt ttctgcagcg    60
gggattaata tgattagtcc acccccacg agaaactctg ctgattcagc caggagctta   120
ggagggggag gtcactttat aagggtctgg ggggtcaga acccagagtc atccagctgg    180
agccctgagt ggctgagctc aggccttcgc agcattcttg ggtgggagca gccacgggtc   240
agccacaagg gccacagcc                                                259
```

<210> SEQ ID NO 17
<211> LENGTH: 259
<212> TYPE: DNA
<213> ORGANISM: Artificial Sequence
<220> FEATURE:
<223> OTHER INFORMATION: synthetic

<400> SEQUENCE: 17

```
tcctcctagt gtcaccttgg cccctcttag aagccaatta ggccctcagt ttctgcagcg    60
gggattaata tgattatgaa cacatgatat ctcccagatg ctgattcagc caggagctta   120
ggagggggag gtcactttat aagggtctgg ggggtcaga acccagagtc atccagctgg    180
agccctgagt ggctgagctc aggccttcgc agcattcttg ggtgggagca gccacgggtc   240
agccacaagg gccacagcc                                                259
```

<210> SEQ ID NO 18
<211> LENGTH: 254
<212> TYPE: DNA
<213> ORGANISM: Artificial Sequence
<220> FEATURE:
<223> OTHER INFORMATION: synthetic

<400> SEQUENCE: 18

```
tcctcctagt gtcaccttgg cccctcttag aagccaatta ggccctcagt ttctgcagcg    60
gggattaata tgattatgaa cacatctccc agatgctgat tcagccagga gcttaggagg   120
gggaggtcac tttataaggg tctgggggg tcagaaccca gagtcatcca gctggagccc    180
tgagtggctg agctcaggcc ttcgcagcat tcttggtgg gagcagccac gggtcagcca   240
caagggccac agcc                                                      254
```

<210> SEQ ID NO 19
<211> LENGTH: 259
<212> TYPE: DNA

<213> ORGANISM: Artificial Sequence
<220> FEATURE:
<223> OTHER INFORMATION: synthetic

<400> SEQUENCE: 19

```
tcctcctagt gtcaccttgg cccctcttag aagccaatta ggccctcagt ttctgcagcg    60
gggattaata tgattagtcc acccccaat ctcccagatg ctgattcagc caggagctta   120
ggagggggag gtcactttat aagggtctgg ggggtcaga acccagagtc atccagctgg   180
agccctgagt ggctgagctc aggccttcgc agcattcttg ggtgggagca gccacgggtc   240
agccacaagg gccacagcc                                                259
```

<210> SEQ ID NO 20
<211> LENGTH: 259
<212> TYPE: DNA
<213> ORGANISM: Artificial Sequence
<220> FEATURE:
<223> OTHER INFORMATION: synthetic

<400> SEQUENCE: 20

```
tcctcctagt gtcaccttgg cccctcttag aagccaatta ggccctcagt ttctgcagcg    60
gggattaata tgattacgac cgtatcgggg ttagggagtg ctgattcagc caggagctta   120
ggagggggag gtcactttat aagggtctgg ggggtcaga acccagagtc atccagctgg   180
agccctgagt ggctgagctc aggccttcgc agcattcttg ggtgggagca gccacgggtc   240
agccacaagg gccacagcc                                                259
```

<210> SEQ ID NO 21
<211> LENGTH: 254
<212> TYPE: DNA
<213> ORGANISM: Artificial Sequence
<220> FEATURE:
<223> OTHER INFORMATION: synthetic

<400> SEQUENCE: 21

```
tcctcctagt gtcaccttgg cccctcttag aagccaatta ggccctcagt ttctgcagcg    60
gggattaata tgattatccc ccaatctccc agatgctgat tcagccagga gcttaggagg   120
ggaggtcac tttataaggg tctgggggggg tcagaaccca gagtcatcca gctggagccc   180
tgagtggctg agctcaggcc ttcgcagcat tcttgggtgg gagcagccac gggtcagcca   240
caagggccac agcc                                                     254
```

<210> SEQ ID NO 22
<211> LENGTH: 259
<212> TYPE: DNA
<213> ORGANISM: Artificial Sequence
<220> FEATURE:
<223> OTHER INFORMATION: synthetic

<400> SEQUENCE: 22

```
tcctcctagt gtcaccttgg cccctcttag aagccaatta ggccctcagt ttctgcagcg    60
gggattaata tgattagagg gattggtgct atgccagctg ctgattcagc caggagctta   120
ggagggggag gtcactttat aagggtctgg ggggtcaga acccagagtc atccagctgg   180
agccctgagt ggctgagctc aggccttcgc agcattcttg ggtgggagca gccacgggtc   240
agccacaagg gccacagcc                                                259
```

<210> SEQ ID NO 23
<211> LENGTH: 251

<212> TYPE: DNA
<213> ORGANISM: Artificial Sequence
<220> FEATURE:
<223> OTHER INFORMATION: synthetic

<400> SEQUENCE: 23

```
tcctcctagt gtcaccttgg cccctcttag aagccaatta ggccctcagt ttctgcagcg      60
gggattaata tgattatgaa atctcccaga tgctgattca gccaggagct taggaggggg     120
aggtcacttt ataagggtct ggggggggtca gaacccagag tcatccagct ggagccctga   180
gtggctgagc tcaggccttc gcagcattct tgggtgggag cagccacggg tcagccacaa    240
gggccacagc c                                                         251
```

<210> SEQ ID NO 24
<211> LENGTH: 603
<212> TYPE: DNA
<213> ORGANISM: Artificial Sequence
<220> FEATURE:
<223> OTHER INFORMATION: synthetic

<400> SEQUENCE: 24

```
atgatcgatc tggaacctgg cgaaaaaccg tataagtgcc cagaatgcgg caagtctttt     60
tcccagtctg gccacctgac ggaacatcag cgcactcaca ccggcgagaa accatataaa    120
tgtccggagt gcggcaagag ctttagccag aatagcaccc tgaccgaaca tcagcgtacg   180
cacacgggtg aaaagccata taatgccct gagtgcggca atcctttag cacctctggc      240
catctggtcc gtcaccagcg cacccaccag aataagaagg gcggttctgg tgacggtaaa    300
aagaaacagc acgcctgtcc agagtgtggc aaatctttt cccgtgaaga caacctgcac     360
actcaccagc gcactcatac tggcgagaaa ccttacaagt gtccggaatg tggtaagagc    420
ttctccactt ccggccatct ggttcgtcac cagcgcacgc acaccggcga aaaaccatac    480
aagtgcccgg aatgcggcaa atcattctcc cgtagcgaca aactggttcg tcaccaacgt    540
acgcataccg gtaaaaagac ttcctctaga tacccgtacg acgttccaga ctatgcatct    600
tga                                                                  603
```

<210> SEQ ID NO 25
<211> LENGTH: 200
<212> TYPE: PRT
<213> ORGANISM: Artificial Sequence
<220> FEATURE:
<223> OTHER INFORMATION: synthetic

<400> SEQUENCE: 25

```
Met Ile Asp Leu Glu Pro Gly Glu Lys Pro Tyr Lys Cys Pro Glu Cys
1               5                   10                  15

Gly Lys Ser Phe Ser Gln Ser Gly His Leu Thr Glu His Gln Arg Thr
            20                  25                  30

His Thr Gly Glu Lys Pro Tyr Lys Cys Pro Glu Cys Gly Lys Ser Phe
        35                  40                  45

Ser Gln Asn Ser Thr Leu Thr Glu His Gln Arg Thr His Thr Gly Glu
    50                  55                  60

Lys Pro Tyr Lys Cys Pro Glu Cys Gly Lys Ser Phe Ser Thr Ser Gly
65                  70                  75                  80

His Leu Val Arg His Gln Arg Thr His Gln Asn Lys Lys Gly Gly Ser
                85                  90                  95

Gly Asp Gly Lys Lys Gln His Ala Cys Pro Glu Cys Gly Lys Ser
            100                 105                 110
```

Phe Ser Arg Glu Asp Asn Leu His Thr His Gln Arg Thr His Thr Gly
        115                 120                 125

Glu Lys Pro Tyr Lys Cys Pro Glu Cys Gly Lys Ser Phe Ser Thr Ser
        130                 135                 140

Gly His Leu Val Arg His Gln Arg Thr His Thr Gly Glu Lys Pro Tyr
145                 150                 155                 160

Lys Cys Pro Glu Cys Gly Lys Ser Phe Ser Arg Ser Asp Lys Leu Val
                165                 170                 175

Arg His Gln Arg Thr His Thr Gly Lys Lys Thr Ser Ser Arg Tyr Pro
            180                 185                 190

Tyr Asp Val Pro Asp Tyr Ala Ser
        195                 200

<210> SEQ ID NO 26
<211> LENGTH: 681
<212> TYPE: DNA
<213> ORGANISM: Artificial Sequence
<220> FEATURE:
<223> OTHER INFORMATION: synthetic

<400> SEQUENCE: 26
atgatcgatc tggaacctgg cgaaaaaccg tataagtgcc cagaatgcgg caagtctttt      60
tccacctctg gcaatctggt gcgccatcag cgcactcaca ccggcgagaa accatataaa     120
tgtccggagt gcggcaagag ctttagcact agcggcgagc tggtccgtca tcagcgtacg     180
cacacgggtg aaaagccata taatgccct gagtgcggca atcctttag cacctctggt      240 aacctggtac gtcaccagcg cacccacacg ggccgttctt ctgtagagtc tgcgtgcgtc     300
acctctgtac tggttgccct cctgccggct acctctgcac cgactcaggt gagcggtgaa     360
aagccataca atgtccaga gtgtggcaaa tcttttttcc agtctggcaa cctgactgaa      420
caccagcgca ctcatactgg cgagaaacct tacaagtgtc cggaatgtgg taagagcttc     480
tcctccaaaa agcatctggc tgagcaccag cgcacgcaca ccggcgaaaa accatacaag     540 tgccccggaat gcggcaaatc attcagctcc aaaaaggctc tgactgagca ccaacgtacg     600
cataccggta aaaagacttc ctctagaccg aaaaagaaac gcaaagttta cccatacgac     660
gtacctgatt atgcaagctg a                                                681

<210> SEQ ID NO 27
<211> LENGTH: 226
<212> TYPE: PRT
<213> ORGANISM: Artificial Sequence
<220> FEATURE:
<223> OTHER INFORMATION: synthetic

<400> SEQUENCE: 27

Met Ile Asp Leu Glu Pro Gly Glu Lys Pro Tyr Lys Cys Pro Glu Cys
1               5                   10                  15

Gly Lys Ser Phe Ser Thr Ser Gly Asn Leu Val Arg His Gln Arg Thr
            20                  25                  30

His Thr Gly Glu Lys Pro Tyr Lys Cys Pro Glu Cys Gly Lys Ser Phe
        35                  40                  45

Ser Thr Ser Gly Glu Leu Val Arg His Gln Arg Thr His Thr Gly Glu
    50                  55                  60

Lys Pro Tyr Lys Cys Pro Glu Cys Gly Lys Ser Phe Ser Thr Ser Gly
65                  70                  75                  80

Asn Leu Val Arg His Gln Arg Thr His Thr Gly Arg Ser Ser Val Glu

|  | | 85 | | | 90 | | | | 95 | | |
|---|---|---|---|---|---|---|---|---|---|---|---|
| Ser | Ala | Cys | Val | Thr | Ser | Val | Leu | Val | Ala | Leu | Leu | Pro | Ala | Thr | Ser |
|  |  |  | 100 |  |  |  | 105 |  |  |  | 110 |

Ala Pro Thr Gln Val Ser Gly Glu Lys Pro Tyr Lys Cys Pro Glu Cys
            115                 120                 125

Gly Lys Ser Phe Ser Gln Ser Gly Asn Leu Thr Glu His Gln Arg Thr
        130                 135                 140

His Thr Gly Glu Lys Pro Tyr Lys Cys Pro Glu Cys Gly Lys Ser Phe
145                 150                 155                 160

Ser Ser Lys Lys His Leu Ala Glu His Gln Arg Thr His Thr Gly Glu
                165                 170                 175

Lys Pro Tyr Lys Cys Pro Glu Cys Gly Lys Ser Phe Ser Ser Lys Lys
            180                 185                 190

Ala Leu Thr Glu His Gln Arg Thr His Thr Gly Lys Lys Thr Ser Ser
        195                 200                 205

Arg Pro Lys Lys Arg Lys Val Tyr Pro Tyr Asp Val Pro Asp Tyr
    210                 215                 220

Ala Ser
225

<210> SEQ ID NO 28
<211> LENGTH: 3021
<212> TYPE: DNA
<213> ORGANISM: Artificial Sequence
<220> FEATURE:
<223> OTHER INFORMATION: synthetic

<400> SEQUENCE: 28

```
atgtacccat acgatgtccc agactacgcg aatttaatgt cgcggacccg gctcccttcc      60
ccacccgcac ccagcccagc gttttcggcc gactcgttct cagacctgct taggcagttc     120
gacccctcac tgtttaacac atcgttgttc gactcccttc ctccgtttgg ggcgcaccat     180
acggaggcgg ccaccgggga gtgggatgag gtgcagtcgg gattgagagc tgcggatgca     240
ccacccccaa ccatgcgggt ggccgtcacc gctgcccgac cgccgagggc gaagcccgca     300
ccaaggcgga gggcagcgca accgtccgac gcaagccccg cagcgcaagt agatttgaga     360
actttgggat attcacagca gcagcaggaa aagatcaagc ccaaagtgag gtcgacagtc     420
gcgcagcatc acgaagcgct ggtgggtcat gggtttacac atgcccacat cgtagccttg     480
tcgcagcacc ctgcagccct tggcacggtc gccgtcaagt accaggacat gattgcggcg     540
ttgccggaag ccacacatga ggcgatcgtc ggtgtgggga acagtggagc ggagcccga     600
gcgcttgagg ccctgttgac ggtcgcggga gagctgagag gcctcccct tcagctggac     660
acgggccagt tgctgaagat cgcgaagcgg ggaggagtca cggcggtcga ggcggtgcac     720
gcgtggcgca atgcgctcac gggagcaccc ctcaacctga ccccagagca ggtcgtggca     780
attgcgagcc atgacggggg aaaagcaggc actcgaaaccg tccagaggtt gctgcctgtg     840
ctgtgccaag cgcacggact tacgccagag caggtcgtgg caattgcgag caacatcggg     900
ggaaagcagg cactcgaaac cgtccagagg ttgctgcctg tgctgtgcca agcgcacgga     960
ctaaccccag agcaggtcgt ggcaattgcg agcaacaacg ggggaaagca ggcactcgaa    1020
accgtccaga ggttgctgcc tgtgctgtgc caagcgcacg ggttgacccc agagcaggtc    1080
gtggcaattg cgagccatga cgggggaaag caggcactcg aaaccgtcca gaggttgctg    1140
cctgtgctgt gccaagcgca cggcctgacc ccagagcagg tcgtggcaat tgcgagcaac    1200
```

| | |
|---|---|
| atcgggggaa agcaggcact cgaaaccgtc cagaggttgc tgcctgtgct gtgccaagcg | 1260 |
| cacggactga caccgagca ggtcgtggca attgcgagca acggagggg aaagcaggca | 1320 |
| ctcgaaaccg tccagaggtt gctgcctgtg ctgtgccaag cgcacggact tacacccgaa | 1380 |
| caagtcgtgg caattgcgag ccatgacggg gaaagcagg cactcgaaac cgtccagagg | 1440 |
| ttgctgcctg tgctgtgcca agcgcacgga cttacgccag agcaggtcgt ggcaattgcg | 1500 |
| agcaacggag ggggaaagca ggcactcgaa accgtccaga ggttgctgcc tgtgctgtgc | 1560 |
| caagcgcacg gactaacccc agagcaggtc gtggcaattg cgagcaacaa cggggggaaag | 1620 |
| caggcactcg aaaccgtcca gaggttgctg cctgtgctgt gccaagcgca cgggttgacc | 1680 |
| ccagagcagg tcgtggcaat tgcgagcaac aacggggggaa agcaggcact cgaaaccgtc | 1740 |
| cagaggttgc tgcctgtgct gtgccaagcg cacggcctga ccccagagca ggtcgtggca | 1800 |
| attgcgagca acaacggggg aaagcaggca ctcgaaaccg tccagaggtt gctgcctgtg | 1860 |
| ctgtgccaag cgcacggact gacaccagag caggtcgtgg caattgcgag caacatcggg | 1920 |
| ggaaagcagg cactcgaaac cgtccagagg ttgctgcctg tgctgtgcca agcgcacggc | 1980 |
| ctcaccccag agcaggtcgt ggcaattgcg agcaacaacg ggggaaagca ggcactcgaa | 2040 |
| accgtccaga ggttgctgcc tgtgctgtgc aagcgcacg gacttacgcc agagcaggtc | 2100 |
| gtggcaattg cgagcaacat cggggggaaag caggcactcg aaaccgtcca gaggttgctg | 2160 |
| cctgtgctgt gccaagcgca cggactaacc ccagagcagg tcgtggcaat tgcgagcaac | 2220 |
| ggaggggggaa agcaggcact cgaaaccgtc cagaggttgc tgcctgtgct gtgccaagcg | 2280 |
| cacgggttga ccccagagca ggtcgtggca attgcgagca acggagggggg aaagcaggca | 2340 |
| ctcgaaaccg tccagaggtt gctgcctgtg ctgtgccaag cgcacggact cacgcctgag | 2400 |
| caggtagtgg ctattgcatc caataacggg ggcagacccg cactggagtc aatcgtggcc | 2460 |
| cagctttcga ggccggaccc cgcgctggcc gcactcacta atgatcatct tgtagcgctg | 2520 |
| gcctgcctcg gcggacgacc cgccttggat gcggtgaaga agggggctccc gcacgcgcct | 2580 |
| gcattgatta agcggaccaa cagaaggatt cccgagagga catcacatcg agtggcagat | 2640 |
| cacgcgcaag tggtccgcgt gctcggattc ttccagtgtc actccacccc cgcacaagcg | 2700 |
| ttcgatgacg ccatgactca atttggtatg tcgagacacg gactgctgca gctctttcgt | 2760 |
| agagtcggtg tcacagaact cgaggcccgc tcgggcacac tgcctcccgc ctcccagcgg | 2820 |
| tgggacagga ttctccaagc gagcggtatg aaacgcgcga agccttcacc tacgtcaact | 2880 |
| cagacacctg accaggcgag ccttcatgcg ttcgcagact cgctggagag ggatttggac | 2940 |
| gcgccctcgc ccatgcatga aggggaccaa actcgcgcgt cagctagccc caagaagaag | 3000 |
| agaaaggtgg aggccagctg a | 3021 |

<210> SEQ ID NO 29
<211> LENGTH: 1006
<212> TYPE: PRT
<213> ORGANISM: Artificial Sequence
<220> FEATURE:
<223> OTHER INFORMATION: synthetic

<400> SEQUENCE: 29

Met Tyr Pro Tyr Asp Val Pro Asp Tyr Ala Asn Leu Met Ser Arg Thr
1               5                   10                  15

Arg Leu Pro Ser Pro Ala Pro Ser Pro Ala Phe Ser Ala Asp Ser
            20                  25                  30

Phe Ser Asp Leu Leu Arg Gln Phe Asp Pro Ser Leu Phe Asn Thr Ser

```
             35                  40                  45
Leu Phe Asp Ser Leu Pro Pro Phe Gly Ala His His Thr Glu Ala Ala
 50                  55                  60
Thr Gly Glu Trp Asp Glu Val Gln Ser Gly Leu Arg Ala Ala Asp Ala
 65                  70                  75                  80
Pro Pro Pro Thr Met Arg Val Ala Val Thr Ala Ala Arg Pro Pro Arg
                 85                  90                  95
Ala Lys Pro Ala Pro Arg Arg Arg Ala Ala Gln Pro Ser Asp Ala Ser
            100                 105                 110
Pro Ala Ala Gln Val Asp Leu Arg Thr Leu Gly Tyr Ser Gln Gln Gln
            115                 120                 125
Gln Glu Lys Ile Lys Pro Lys Val Arg Ser Thr Val Ala Gln His His
            130                 135                 140
Glu Ala Leu Val Gly His Gly Phe Thr His Ala His Ile Val Ala Leu
145                 150                 155                 160
Ser Gln His Pro Ala Ala Leu Gly Thr Val Ala Val Lys Tyr Gln Asp
                165                 170                 175
Met Ile Ala Ala Leu Pro Glu Ala Thr His Glu Ala Ile Val Gly Val
            180                 185                 190
Gly Lys Gln Trp Ser Gly Ala Arg Ala Leu Glu Ala Leu Leu Thr Val
            195                 200                 205
Ala Gly Glu Leu Arg Gly Pro Pro Leu Gln Leu Asp Thr Gly Gln Leu
210                 215                 220
Leu Lys Ile Ala Lys Arg Gly Gly Val Thr Ala Val Glu Ala Val His
225                 230                 235                 240
Ala Trp Arg Asn Ala Leu Thr Gly Ala Pro Leu Asn Leu Thr Pro Glu
                245                 250                 255
Gln Val Val Ala Ile Ala Ser His Asp Gly Gly Lys Gln Ala Leu Glu
            260                 265                 270
Thr Val Gln Arg Leu Leu Pro Val Leu Cys Gln Ala His Gly Leu Thr
            275                 280                 285
Pro Glu Gln Val Val Ala Ile Ala Ser Asn Ile Gly Gly Lys Gln Ala
            290                 295                 300
Leu Glu Thr Val Gln Arg Leu Leu Pro Val Leu Cys Gln Ala His Gly
305                 310                 315                 320
Leu Thr Pro Glu Gln Val Val Ala Ile Ala Ser Asn Asn Gly Gly Lys
                325                 330                 335
Gln Ala Leu Glu Thr Val Gln Arg Leu Leu Pro Val Leu Cys Gln Ala
            340                 345                 350
His Gly Leu Thr Pro Glu Gln Val Val Ala Ile Ala Ser His Asp Gly
            355                 360                 365
Gly Lys Gln Ala Leu Glu Thr Val Gln Arg Leu Leu Pro Val Leu Cys
            370                 375                 380
Gln Ala His Gly Leu Thr Pro Glu Gln Val Val Ala Ile Ala Ser Asn
385                 390                 395                 400
Ile Gly Gly Lys Gln Ala Leu Glu Thr Val Gln Arg Leu Leu Pro Val
                405                 410                 415
Leu Cys Gln Ala His Gly Leu Thr Pro Glu Gln Val Val Ala Ile Ala
            420                 425                 430
Ser Asn Gly Gly Gly Lys Gln Ala Leu Glu Thr Val Gln Arg Leu Leu
            435                 440                 445
Pro Val Leu Cys Gln Ala His Gly Leu Thr Pro Glu Gln Val Val Ala
            450                 455                 460
```

-continued

Ile Ala Ser His Asp Gly Gly Lys Gln Ala Leu Glu Thr Val Gln Arg
465                 470                 475                 480

Leu Leu Pro Val Leu Cys Gln Ala His Gly Leu Thr Pro Glu Gln Val
            485                 490                 495

Val Ala Ile Ala Ser Asn Gly Gly Lys Gln Ala Leu Glu Thr Val
        500                 505                 510

Gln Arg Leu Leu Pro Val Leu Cys Gln Ala His Gly Leu Thr Pro Glu
            515                 520                 525

Gln Val Val Ala Ile Ala Ser Asn Asn Gly Gly Lys Gln Ala Leu Glu
530                 535                 540

Thr Val Gln Arg Leu Leu Pro Val Leu Cys Gln Ala His Gly Leu Thr
545                 550                 555                 560

Pro Glu Gln Val Val Ala Ile Ala Ser Asn Asn Gly Gly Lys Gln Ala
                565                 570                 575

Leu Glu Thr Val Gln Arg Leu Leu Pro Val Leu Cys Gln Ala His Gly
            580                 585                 590

Leu Thr Pro Glu Gln Val Val Ala Ile Ala Ser Asn Asn Gly Gly Lys
        595                 600                 605

Gln Ala Leu Glu Thr Val Gln Arg Leu Leu Pro Val Leu Cys Gln Ala
610                 615                 620

His Gly Leu Thr Pro Glu Gln Val Val Ala Ile Ala Ser Asn Ile Gly
625                 630                 635                 640

Gly Lys Gln Ala Leu Glu Thr Val Gln Arg Leu Leu Pro Val Leu Cys
                645                 650                 655

Gln Ala His Gly Leu Thr Pro Glu Gln Val Val Ala Ile Ala Ser Asn
            660                 665                 670

Asn Gly Gly Lys Gln Ala Leu Glu Thr Val Gln Arg Leu Leu Pro Val
        675                 680                 685

Leu Cys Gln Ala His Gly Leu Thr Pro Glu Gln Val Val Ala Ile Ala
690                 695                 700

Ser Asn Ile Gly Gly Lys Gln Ala Leu Glu Thr Val Gln Arg Leu Leu
705                 710                 715                 720

Pro Val Leu Cys Gln Ala His Gly Leu Thr Pro Glu Gln Val Val Ala
                725                 730                 735

Ile Ala Ser Asn Gly Gly Gly Lys Gln Ala Leu Glu Thr Val Gln Arg
            740                 745                 750

Leu Leu Pro Val Leu Cys Gln Ala His Gly Leu Thr Pro Glu Gln Val
        755                 760                 765

Val Ala Ile Ala Ser Asn Gly Gly Gly Lys Gln Ala Leu Glu Thr Val
770                 775                 780

Gln Arg Leu Leu Pro Val Leu Cys Gln Ala His Gly Leu Thr Pro Glu
785                 790                 795                 800

Gln Val Val Ala Ile Ala Ser Asn Asn Gly Gly Arg Pro Ala Leu Glu
                805                 810                 815

Ser Ile Val Ala Gln Leu Ser Arg Pro Asp Pro Ala Leu Ala Ala Leu
            820                 825                 830

Thr Asn Asp His Leu Val Ala Leu Ala Cys Leu Gly Gly Arg Pro Ala
835                 840                 845

Leu Asp Ala Val Lys Lys Gly Leu Pro His Ala Pro Ala Leu Ile Lys
850                 855                 860

Arg Thr Asn Arg Arg Ile Pro Glu Arg Thr Ser His Arg Val Ala Asp
865                 870                 875                 880

```
His Ala Gln Val Val Arg Val Leu Gly Phe Gln Cys His Ser His
                885                 890                 895

Pro Ala Gln Ala Phe Asp Asp Ala Met Thr Gln Phe Gly Met Ser Arg
            900                 905                 910

His Gly Leu Leu Gln Leu Phe Arg Arg Val Gly Val Thr Glu Leu Glu
        915                 920                 925

Ala Arg Ser Gly Thr Leu Pro Pro Ala Ser Gln Arg Trp Asp Arg Ile
    930                 935                 940

Leu Gln Ala Ser Gly Met Lys Arg Ala Lys Pro Ser Pro Thr Ser Thr
945                 950                 955                 960

Gln Thr Pro Asp Gln Ala Ser Leu His Ala Phe Ala Asp Ser Leu Glu
                965                 970                 975

Arg Asp Leu Asp Ala Pro Ser Pro Met His Glu Gly Asp Gln Thr Arg
            980                 985                 990

Ala Ser Ala Ser Pro Lys Lys Lys  Arg Lys Val Glu Ala Ser
        995                 1000                 1005

<210> SEQ ID NO 30
<211> LENGTH: 2085
<212> TYPE: DNA
<213> ORGANISM: Artificial Sequence
<220> FEATURE:
<223> OTHER INFORMATION: synthetic

<400> SEQUENCE: 30
```

| | | | | | |
|---|---|---|---|---|---|
| atgtacccat | acgatgtccc | agactacgcg | aatttaaacc | ccaagaagaa | gcggaaggtg | 60 |
| cacgggaatt | ctgcgagcgc | gccgcgccgc | gcgcggcgc | agccgagcga | tgcgagcccg | 120 |
| gcggcgcagg | tggatctgcg | caccctgggc | tatagccagc | agcagcagga | aaaaattaaa | 180 |
| ccgaaagtgc | gcagcaccgt | ggcgcagcat | catgaagcgc | tggtgggcca | tggctttacc | 240 |
| catgcgcata | ttgtggcgct | gagccagcat | ccggcggcgc | tgggcaccgt | ggcggtgaaa | 300 |
| tatcaggata | tgattgcggc | gctgccggaa | gcgacccatg | aagcgattgt | gggcgtgggc | 360 |
| aaacagtgga | gcggcgcgcg | cgcgctggaa | gcgctgctga | ccgtggcggg | cgaactgcgc | 420 |
| ggcccgccgc | tgcagctgga | taccggccag | ctgctgaaaa | ttgcgaaacg | cggcggcgtg | 480 |
| accgcggtgg | aagcggtgca | tgcgtggcgc | aacgcgctga | ccggcgcgcc | gctgaacctg | 540 |
| accccgcagc | aggtggtggc | gattgcgagc | catgatggcg | gcaaacaggc | gctggaaacc | 600 |
| gtgcagcgcc | tgctgccggt | gctgtgccag | gcgcatggcc | tgaccccgga | acaggtggtg | 660 |
| gcgattgcga | gcaacggcgg | cggcaaacag | gcgctggaaa | ccgtgcagcg | cctgctgccg | 720 |
| gtgctgtgcc | aggcgcatgg | cctgaccccg | gaacaggtgg | tggcgattgc | gagcaacaac | 780 |
| ggcggcaaac | aggcgctgga | accgtgcag | cgcctgctgc | cggtgctgtg | ccaggcgcat | 840 |
| ggcctgaccc | cggaacaggt | ggtggcgatt | gcgagcaaca | acggcggcaa | acaggcgctg | 900 |
| gaaaccgtgc | agcgcctgct | gccggtgctg | tgccaggcgc | atggcctgac | cccggaacag | 960 |
| gtggtggcga | ttgcgagcaa | caacggcggc | aaacaggcgc | tggaaaccgt | gcagcgcctg | 1020 |
| ctgccggtgc | tgtgccaggc | gcatggcctg | accccggaac | aggtggtggc | gattgcgagc | 1080 |
| aacattggcg | gcaaacaggc | gctggaaacc | gtgcagcgcc | tgctgccggt | gctgtgccag | 1140 |
| gcgcatggcc | tgaccccgca | gcaggtggtg | gcgattgcga | gcaacaacgg | cggcaaacag | 1200 |
| gcgctggaaa | ccgtgcaggc | gctgctgccg | gtgctgtgcc | aggcgcatgg | cctgaccccg | 1260 |
| gaacaggtgg | tggcgattgc | gagcaacatt | ggcggcaaac | aggcgctgga | aaccgtgcag | 1320 |
| gcgctgctgc | cggtgctgtg | ccaggcgcat | ggcctgaccc | cggaacaggt | ggtggcgatt | 1380 |

```
gcgagcaacg gcggcggcaa acaggcgctg gaaaccgtgc agcgcctgct gccggtgctg   1440
tgccaggcgc atggcctgac cccgcagcag gtggtggcga ttgcgagcaa cggcggcggc   1500
aaacaggcgc tggaaaccgt gcagcgcctg ctgccggtgc tgtgccaggc gcatggcctg   1560
accccgcagc aggtggtggc gattgcgagc aacaacggcg gcaaacaggc gctggaaacc   1620
gtgcagcgcc tgctgccggt gctgtgccag gcgcatggcc tgaccccgga acaggtggtg   1680
gcgattgcga gcaacaacgg cggcaaacag gcgctggaaa ccgtgcagcg cctgctgccg   1740
gtgctgtgcc aggcgcatgg cctgaccccg aacaggtgg tggcgattgc gagcaacaac   1800
ggcggcaaac aggcgctgga aaccgtgcag cgcctgctgc cggtgctgtg ccaggcgcat   1860
ggcctgaccc cggaacaggt ggtggcgatt gcgagcaaca acggcggcaa acaggcgctg   1920
gaaaccgtgc agcgcctgct gccggtgctg tgccaggcgc atggcctgac cccgcagcag   1980
gtggtggcga ttgcgagcaa caacggcggc cgcccggcgc tggaaagcat gtgtgcgcag   2040
ctgagccgcc cggatccggc gctggcggcg ctgaccggca gctga             2085
```

<210> SEQ ID NO 31
<211> LENGTH: 694
<212> TYPE: PRT
<213> ORGANISM: Artificial Sequence
<220> FEATURE:
<223> OTHER INFORMATION: synthetic

<400> SEQUENCE: 31

```
Met Tyr Pro Tyr Asp Val Pro Asp Tyr Ala Asn Leu Asn Pro Lys Lys
1               5                   10                  15

Lys Arg Lys Val His Gly Asn Ser Ala Ser Ala Pro Arg Arg Arg Ala
            20                  25                  30

Ala Gln Pro Ser Asp Ala Ser Pro Ala Ala Gln Val Asp Leu Arg Thr
        35                  40                  45

Leu Gly Tyr Ser Gln Gln Gln Glu Lys Ile Lys Pro Lys Val Arg
    50                  55                  60

Ser Thr Val Ala Gln His His Glu Ala Leu Val Gly His Gly Phe Thr
65                  70                  75                  80

His Ala His Ile Val Ala Leu Ser Gln His Pro Ala Ala Leu Gly Thr
                85                  90                  95

Val Ala Val Lys Tyr Gln Asp Met Ile Ala Ala Leu Pro Glu Ala Thr
            100                 105                 110

His Glu Ala Ile Val Gly Val Gly Lys Gln Trp Ser Gly Ala Arg Ala
        115                 120                 125

Leu Glu Ala Leu Leu Thr Val Ala Gly Glu Leu Arg Gly Pro Pro Leu
    130                 135                 140

Gln Leu Asp Thr Gly Gln Leu Leu Lys Ile Ala Lys Arg Gly Gly Val
145                 150                 155                 160

Thr Ala Val Glu Ala Val His Ala Trp Arg Asn Ala Leu Thr Gly Ala
                165                 170                 175

Pro Leu Asn Leu Thr Pro Gln Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Ala His Gly Leu Thr Pro Glu Gln Val Val Ala Ile Ala Ser
    210                 215                 220

Asn Gly Gly Gly Lys Gln Ala Leu Glu Thr Val Gln Arg Leu Leu Pro
225                 230                 235                 240
```

-continued

```
Val Leu Cys Gln Ala His Gly Leu Thr Pro Glu Gln Val Val Ala Ile
                245                 250                 255
Ala Ser Asn Asn Gly Gly Lys Gln Ala Leu Glu Thr Val Gln Arg Leu
            260                 265                 270
Leu Pro Val Leu Cys Gln Ala His Gly Leu Thr Pro Glu Gln Val Val
        275                 280                 285
Ala Ile Ala Ser Asn Asn Gly Gly Lys Gln Ala Leu Glu Thr Val Gln
    290                 295                 300
Arg Leu Leu Pro Val Leu Cys Gln Ala His Gly Leu Thr Pro Glu Gln
305                 310                 315                 320
Val Val Ala Ile Ala Ser Asn Asn Gly Gly Lys Gln Ala Leu Glu Thr
                325                 330                 335
Val Gln Arg Leu Leu Pro Val Leu Cys Gln Ala His Gly Leu Thr Pro
            340                 345                 350
Glu Gln Val Val Ala Ile Ala Ser Asn Ile Gly Gly Lys Gln Ala Leu
        355                 360                 365
Glu Thr Val Gln Arg Leu Leu Pro Val Leu Cys Gln Ala His Gly Leu
    370                 375                 380
Thr Pro Gln Gln Val Val Ala Ile Ala Ser Asn Asn Gly Gly Lys Gln
385                 390                 395                 400
Ala Leu Glu Thr Val Gln Ala Leu Leu Pro Val Leu Cys Gln Ala His
                405                 410                 415
Gly Leu Thr Pro Glu Gln Val Val Ala Ile Ala Ser Asn Ile Gly Gly
            420                 425                 430
Lys Gln Ala Leu Glu Thr Val Gln Ala Leu Leu Pro Val Leu Cys Gln
        435                 440                 445
Ala His Gly Leu Thr Pro Glu Gln Val Val Ala Ile Ala Ser Asn Gly
    450                 455                 460
Gly Gly Lys Gln Ala Leu Glu Thr Val Gln Arg Leu Leu Pro Val Leu
465                 470                 475                 480
Cys Gln Ala His Gly Leu Thr Pro Gln Gln Val Val Ala Ile Ala Ser
                485                 490                 495
Asn Gly Gly Gly Lys Gln Ala Leu Glu Thr Val Gln Arg Leu Leu Pro
            500                 505                 510
Val Leu Cys Gln Ala His Gly Leu Thr Pro Gln Gln Val Val Ala Ile
        515                 520                 525
Ala Ser Asn Asn Gly Gly Lys Gln Ala Leu Glu Thr Val Gln Arg Leu
    530                 535                 540
Leu Pro Val Leu Cys Gln Ala His Gly Leu Thr Pro Glu Gln Val Val
545                 550                 555                 560
Ala Ile Ala Ser Asn Asn Gly Gly Lys Gln Ala Leu Glu Thr Val Gln
                565                 570                 575
Arg Leu Leu Pro Val Leu Cys Gln Ala His Gly Leu Thr Pro Glu Gln
            580                 585                 590
Val Val Ala Ile Ala Ser Asn Asn Gly Gly Lys Gln Ala Leu Glu Thr
        595                 600                 605
Val Gln Arg Leu Leu Pro Val Leu Cys Gln Ala His Gly Leu Thr Pro
    610                 615                 620
Glu Gln Val Val Ala Ile Ala Ser Asn Asn Gly Gly Lys Gln Ala Leu
625                 630                 635                 640
Glu Thr Val Gln Arg Leu Leu Pro Val Leu Cys Gln Ala His Gly Leu
                645                 650                 655
```

Thr Pro Gln Gln Val Val Ala Ile Ala Ser Asn Asn Gly Gly Arg Pro
          660                 665                 670

Ala Leu Glu Ser Ile Val Ala Gln Leu Ser Arg Pro Asp Pro Ala Leu
      675                 680                 685

Ala Ala Leu Thr Gly Ser
    690

<210> SEQ ID NO 32
<211> LENGTH: 6894
<212> TYPE: DNA
<213> ORGANISM: Artificial Sequence
<220> FEATURE:
<223> OTHER INFORMATION: synthetic

<400> SEQUENCE: 32

| | | | | | |
|---|---|---|---|---|---|
| agcgcccaat | acgcaaaccg | cctctccccg | cgcgttggcc | gattcattaa | tgcagctggc | 60 |
| acgacaggtt | tcccgactgg | aaagcgggca | gtgagcgcaa | cgcaattaat | gtgagttagc | 120 |
| tcactcatta | ggcaccccag | gctttacact | ttatgcttcc | ggctcgtatg | ttgtgtggaa | 180 |
| ttgtgagcgg | ataacaattt | cacacaggaa | acagctatga | ccatgattac | gccagattta | 240 |
| attaaggctg | cgcgctcgct | cgctcactga | ggccgcccgg | gcaaagcccg | ggcgtcgggc | 300 |
| gacctttggt | cgcccggcct | cagtgagcga | gcgagcgcgc | agagagggag | tggccaactc | 360 |
| catcactagg | ggttccttgt | agttaatgat | taaccccgcca | tgctactat | ctacgtagcc | 420 |
| atgctctagg | aagatcggaa | ttcgccctta | agctagctcc | tcctagtgtc | accttggccc | 480 |
| ctcttagaag | ccaattaggc | cctcagtttc | tgcagcgggg | attaatatga | ttatgaaatc | 540 |
| tcccagatgc | tgattcagcc | aggagcttag | gaggggagg | tcactttata | agggtctggg | 600 |
| ggggtcagaa | cccagagtca | tccagctgga | gccctgagtg | gctgagctca | ggccttcgca | 660 |
| gcattcttgg | gtgggagcag | ccacgggtca | gccacaaggg | ccacagccca | attgatgatc | 720 |
| gatctggaac | ctggcgaaaa | accgtataag | tgcccagaat | gcggcaagtc | ttttttcccag | 780 |
| tctggccacc | tgacggaaca | tcagcgcact | cacaccggcg | agaaaccata | taaatgtccg | 840 |
| gagtgcggca | agagctttag | ccagaatagc | accctgaccg | aacatcagcg | tacgcacacg | 900 |
| ggtgaaaagc | catataaatg | ccctgagtgc | ggcaaatcct | ttagcacctc | tggccatctg | 960 |
| gtccgtcacc | agcgcacccca | ccagaataag | aagggcggtt | ctggtgacgg | taaaaagaaa | 1020 |
| cagcacgcct | gtccagagtg | tggcaaatct | tttccccgtg | aagacaacct | gcacactcac | 1080 |
| cagcgcactc | atactggcga | gaaaccttac | aagtgtccgg | aatgtggtaa | gagcttctcc | 1140 |
| acttccggcc | atctggttcg | tcaccagcgc | acgcacaccg | cgaaaaacc | atacaagtgc | 1200 |
| ccggaatgcg | gcaaatcatt | ctcccgtagc | gacaaactgg | ttcgtcacca | acgtacgcat | 1260 |
| accggtaaaa | agacttcctc | tagatacccg | tacgacgttc | cagactatgc | atcttgacat | 1320 |
| atggcctcga | ctgtgccttc | tagttgccag | ccatctgttg | tttgcccctc | cccgtgcct | 1380 |
| tccttgaccc | tggaaggtgc | cactcccact | gtcctttcct | aataaaatga | ggaaattgca | 1440 |
| tcgcattgtc | tgagtaggtg | tcattctatt | ctggggggtg | gggtggggca | ggacagcaag | 1500 |
| ggggaggatt | gggaagacaa | tagcaggcat | gctggggaac | tagttgtagt | taatgattaa | 1560 |
| cccgccatgc | tacttatcta | cgtagccatg | ctctaggaag | atcggaattc | gcccttaagt | 1620 |
| tacgctagct | ccctgcaggt | cataaaatcc | cagtccagag | tcaccagccc | ttcttaacca | 1680 |
| cttcctactg | tgtgaccctt | tcagccttta | cttcctcatc | agtaaaatga | ggctgatgat | 1740 |
| atgggcatcc | atactccagg | gccagtgtga | gcttacaaca | agataaggag | tggtgctgag | 1800 |

```
cctggtgccg ggcaggcagc aggcatgttt ctcccaatta tgccctctca ctgccagccc   1860
cacctccatt gtcctcaccc ccagggctca aggttctgcc ttcccctttc tcagccctga   1920
ccctactgaa catgtctccc cactcccagg cagtgccagg gcctctcctg gagggttgcg   1980
gggacagaag gacagccgga gtgcagagtc agcggttgag ggattggggc tatgccagct   2040
aatccgaagg gttggggggg ctgagctgga ttcacctgtc cttgtctctg attggctctt   2100
ggacacccct agcccccaaa tcccactaag cagccccacc agggattgca caggtccgta   2160
gagagccagt tgattgcagg tcctcctggg gccagaaggg tgcctgggag gccaggttct   2220
ggggatcccc tccatccaga agaaccacct gctcactctg tcccttcgcc tgctgctggg   2280
accgcggccg catgaatggc acagaaggcc ctaacttcta cgtgcccttc tccaatgcga   2340
cgggtgtggt acgcagcccc ttcgagtacc acagtactac cctggctgag ccatggcagt   2400
tctccatgct ggccgcctac atgtttctgc tgatcgtgct gggcttcccc atcaacttcc   2460
tcacgctcta cgtcaccgtc agcacaagaa agctgcgcac gcctctcaac tacatcctgc   2520
tcaacctagc cgtggctgac ctcttcatgg tcctaggtgg cttcaccagc ccctctaca   2580
cctctctgca tggatacttc gtcttcgggc ccacaggatg caatttggag ggcttctttg   2640
ccaccctggg cggtgaaatt gccctgtggt ccttggtggt cctggccatc gagcggtacg   2700
tggtggtgtg taagcccatg agcaacttcc gcttcgggga gaaccatgcc atcatgggcg   2760
ttgccttcac ctgggtcatg gcgctggcct gcgccgcacc cccactcgcc ggctggtcca   2820
ggtacatccc cgagggcctg cagtgctcgt gtggaatcga ctactacacg ctcaagccgg   2880
aggtcaacaa cgagtctttt gtcatctaca tgttcgtggt ccacttcacc atccccatga   2940
ttatcatctt tttctgctat gggcagctcg tcttcaccgt caaggaggcc gctgcccagc   3000
agcaggagtc agccaccaca cagaaggcag agaaggaggt cacccgcatg gtcatcatca   3060
tggtcatcgc tttcctgatc tgctgggtgc cctacgccag cgtggcattc tacatcttca   3120
cccaccaggg ctccaacttc ggtcccatct tcatgaccat cccagcgttc tttgccaaga   3180
gcgccgccat ctacaaccct gtcatctata tcatgatgaa caagcagttc cggaactgca   3240
tgctcaccac catctgctgc ggcaagaacc cactgggtga cgatgaggcc tctgctaccg   3300
tgtccaagac ggagacgagc caggtggccc cggcctaaaa gcttggatcc aatcaacctc   3360
tggattacaa aatttgtgaa agattgactg gtattcttaa ctatgttgct ccttttacgc   3420
tatgtggata cgctgcttta atgcctttgt atcatgctat tgcttcccgt atggctttca   3480
ttttctcctc cttgtataaa tcctggttgc tgtctcttta tgaggagttg tggcccgttg   3540
tcaggcaacg tggcgtggtg tgcactgtgt ttgctgacgc aaccccact ggttggggca   3600
ttgccaccac ctgtcagctc ctttccggga ctttcgcttt cccctccct attgccacgg   3660
cggaactcat cgccgcctgc cttgcccgct gctggacagg gctcggctg ttgggcactg   3720
acaattccgt ggtgttgtcg gggaagctga cgtcctttcc atggctgctc gcctgtgttg   3780
ccacctggat tctgcgcggg acgtccttct gctacgtccc ttcggccctc aatccagcgg   3840
accttccttc ccgcggcctg ctgccggctc tgcggcctct tccgcgtctt cgagatctgc   3900
ctcgactgtg ccttctagtt gccagccatc tgttgtttgc ccctccccg tgccttcctt   3960
gaccctggaa ggtgccactc ccactgtcct ttcctaataa aatgaggaaa ttgcatcgca   4020
ttgtctgagt aggtgtcatt ctattctggg gggtggggtg gggcaggaca gcaaggggga   4080
ggattgggaa gacaatagca ggcatgctgg ggactcgagt taagggcgaa ttcccgatta   4140
ggatcttcct agagcatggc tacgtagata agtagcatgg cgggttaatc attaactaca   4200
```

```
aggaacccct agtgatggag ttggccactc cctctctgcg cgctcgctcg ctcactgagg    4260
ccgggcgacc aaaggtcgcc cgacgcccgg gctttgcccg gcggcctca gtgagcgagc     4320 gagcgcgcag ccttaattaa cctaattcac tggccgtcgt tttacaacgt cgtgactggg    4380
aaaaccctgg cgttacccaa cttaatcgcc ttgcagcaca tcccccttc gccagctggc     4440 gtaatagcga agaggcccgc accgatcgcc cttcccaaca gttgcgcagc ctgaatggcg    4500
aatgggacgc gccctgtagc ggcgcattaa gcgcggcggg tgtggtggtt acgcgcagcg    4560
tgaccgctac acttgccagc gccctagcgc ccgctccttt cgctttcttc ccttcctttc    4620
tcgccacgtt cgccggcttt ccccgtcaag ctctaaatcg gggctccct ttagggttcc     4680 gatttagtgc tttacggcac ctcgacccca aaaaacttga ttagggtgat ggttcacgta    4740
gtgggccatc gccccgatag acggtttttc gccctttgac gctggagttc acgttcctca    4800
atagtggact cttgttccaa actggaacaa cactcaaccc tatctcggtc tattcttttg    4860
atttataagg gatttttccg atttcggcct attggttaaa aaatgagctg atttaacaaa    4920
aatttaacgc gaattttaac aaaatattaa cgtttataat ttcaggtggc atctttcggg    4980
gaaatgtgcg cggaaccccct atttgtttat ttttctaaat acattcaaat atgtatccgc    5040
tcatgagaca ataaccctga taaatgcttc aataatattg aaaaaggaag agtatgagta    5100
ttcaacattt ccgtgtcgcc cttattccct tttttgcggc attttgcctt cctgtttttg    5160
ctcacccaga aacgctggtg aaagtaaaag atgctgaaga tcagttgggt gcacgagtgg    5220
gttacatcga actggatctc aatagtggta agatccttga gagttttcgc cccgaagaac    5280
gttttccaat gatgagcact tttaaagttc tgctatgtgg cgcggtatta tcccgtattg    5340
acgccgggca agagcaactc ggtcgccgca tacactattc tcagaatgac ttggttgagt    5400
actcaccagt cacagaaaag catcttacgg atggcatgac agtaagagaa ttatgcagtg    5460
ctgccataac catgagtgat aacactgcgg ccaacttact tctgacaacg atcggaggac    5520
cgaaggagct aaccgctttt ttgcacaaca tgggggatca tgtaactcgc cttgatcgtt    5580
gggaaccgga gctgaatgaa gccataccaa acgacgagcg tgacaccacg atgcctgtag    5640
taatggtaac aacgttgcgc aaactattaa ctggcgaact acttactcta gcttcccggc    5700
aacaattaat agactggatg gaggcggata aagttgcagg accacttctg cgctcggccc    5760
ttccggctgg ctggtttatt gctgataaat ctggagccgg tgagcgtggg tctcgcggta    5820
tcattgcagc actggggcca gatggtaagc cctcccgtat cgtagttatc tacacgacgg    5880
ggagtcaggc aactatggat gaacgaaata gacagatcgc tgagataggt gcctcactga    5940
ttaagcattg gtaactgtca gaccaagttt actcatatat actttagatt gatttaaaac    6000 ttcatttta atttaaaagg atctaggtga agatcctttt tgataatctc atgaccaaaa    6060
tcccttaacg tgagttttcg ttccactgag cgtcagaccc cgtagaaaag atcaaaggat    6120
cttcttgaga tccttttttt ctgcgcgtaa tctgctgctt gcaaacaaaa aaaccaccgc    6180
taccagcggt ggtttgtttg ccggatcaag agctaccaac tcttttccg aaggtaactg     6240 gcttcagcag agcgcagata ccaaatactg tccttctagt gtagccgtag ttaggccacc    6300
acttcaagaa ctctgtagca ccgcctacat acctcgctct gctaatcctg ttaccagtgg    6360
ctgctgccag tggcgataag tcgtgtctta ccgggttgga ctcaagacga tagttaccgg    6420
ataaggcgca gcggtcgggc tgaacggggg gttcgtgcac acagcccagc ttggagcgaa    6480
cgacctacac cgaactgaga tacctacagc gtgagctatg agaaagcgcc acgcttcccg    6540
```

-continued

```
aagggagaaa ggcggacagg tatccggtaa gcggcagggt cggaacagga gagcgcacga   6600
gggagcttcc aggggggaaac gcctggtatc tttatagtcc tgtcgggttt cgccacctct   6660
gacttgagcg tcgattttg tgatgctcgt caggggggcg gagcctatgg aaaaacgcca    6720
gcaacgcggc cttttttacgg ttcctggcct ttttgctgcgg ttttgctcac atgttctttc   6780
ctgcgttatc ccctgattct gtggataacc gtattaccgc ctttgagtga gctgataccg   6840
ctcgccgcag ccgaacgacc gagcgcagcg agtcagtgag cgaggaagcg gaag         6894
```

<210> SEQ ID NO 33
<211> LENGTH: 29
<212> TYPE: DNA
<213> ORGANISM: Artificial Sequence
<220> FEATURE:
<223> OTHER INFORMATION: synthetic

<400> SEQUENCE: 33 gaacacccc aatctcccag atgctgatt                                       29

<210> SEQ ID NO 34
<211> LENGTH: 29
<212> TYPE: DNA
<213> ORGANISM: Artificial Sequence
<220> FEATURE:
<223> OTHER INFORMATION: synthetic

<400> SEQUENCE: 34 gaacacccc aatctcccag atgctgatt                                       29

<210> SEQ ID NO 35
<211> LENGTH: 29
<212> TYPE: DNA
<213> ORGANISM: Artificial Sequence
<220> FEATURE:
<223> OTHER INFORMATION: synthetic

<400> SEQUENCE: 35 cttgtgggggg ttagagggtc tacgactaa                                     29

<210> SEQ ID NO 36
<211> LENGTH: 29
<212> TYPE: DNA
<213> ORGANISM: Artificial Sequence
<220> FEATURE:
<223> OTHER INFORMATION: synthetic

<400> SEQUENCE: 36 cttgtgggggg ttagagggtc tacgactaa                                     29

<210> SEQ ID NO 37
<211> LENGTH: 29
<212> TYPE: DNA
<213> ORGANISM: Artificial Sequence
<220> FEATURE:
<223> OTHER INFORMATION: synthetic

<400> SEQUENCE: 37 cttgtgggggg ttagagggtc tacgactaa                                     29

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
cttaggaggg ggaggtcact                                              20

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
cttaggaggg ggaggtcact                                              20

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
gaatcctccc cctccagtga                                              20

<210> SEQ ID NO 41
<211> LENGTH: 29
<212> TYPE: DNA
<213> ORGANISM: Artificial Sequence
<220> FEATURE:
<223> OTHER INFORMATION: synthetic

<400> SEQUENCE: 41
gaacaccccc aatctcccag atgctgatt                                    29

<210> SEQ ID NO 42
<211> LENGTH: 29
<212> TYPE: DNA
<213> ORGANISM: Artificial Sequence
<220> FEATURE:
<223> OTHER INFORMATION: synthetic

<400> SEQUENCE: 42
gaacaccccc aatctcccag atgctgatt                                    29

<210> SEQ ID NO 43
<211> LENGTH: 522
<212> TYPE: DNA
<213> ORGANISM: Artificial Sequence
<220> FEATURE:
<223> OTHER INFORMATION: synthetic

<400> SEQUENCE: 43
atgatcgatc tggagccagg tgaaaagcct tataagtgcc ctgaatgcgg gaaatcattc      60
agccagaact ccacacttac cgagcaccag agaaccccata ctggggagaa acccctataag   120 tgcccagaat gtgggaagtc tttctctacc agcggacact tggtcaggca ccagagaacg    180
caccagaaca agaaaggagg ttctggtgat ggcaagaaga agcagcatgc ttgtcccgaa    240
tgcggcaagt cctttagcag ggaggacaat ctgcacactc accaacgcac atatactggc    300
gagaagccgt acaagtgtcc cgaatgtggc aaaagtttct ccacaagtgg acatctcgtt    360
cgtcaccagc gaacccacac cggagagaaa ccctacaaat gcccagagtg tgggaaatcc    420
ttttcacgga gcgacaaact ggtgagacat caacgcactc atacaggcaa gaaaacgagc    480
tcacggtacc cttacgatgt gcctgactat gccagttaat aa          522

<210> SEQ ID NO 44
<211> LENGTH: 172
<212> TYPE: PRT
<213> ORGANISM: Artificial Sequence
<220> FEATURE:
<223> OTHER INFORMATION: synthetic

<400> SEQUENCE: 44

```
Met Ile Asp Leu Glu Pro Gly Glu Lys Pro Tyr Lys Cys Pro Glu Cys
1               5                   10                  15

Gly Lys Ser Phe Ser Gln Asn Ser Thr Leu Thr Glu His Gln Arg Thr
            20                  25                  30

His Thr Gly Glu Lys Pro Tyr Lys Cys Pro Glu Cys Gly Lys Ser Phe
        35                  40                  45

Ser Thr Ser Gly His Leu Val Arg His Gln Arg Thr His Gln Asn Lys
    50                  55                  60

Lys Gly Gly Ser Gly Asp Gly Lys Lys Gln His Ala Cys Pro Glu
65                  70                  75                  80

Cys Gly Lys Ser Phe Ser Arg Glu Asp Asn Leu His Thr His Gln Arg
                85                  90                  95

Thr His Thr Gly Glu Lys Pro Tyr Lys Cys Pro Glu Cys Gly Lys Ser
            100                 105                 110

Phe Ser Thr Ser Gly His Leu Val Arg His Gln Arg Thr His Thr Gly
        115                 120                 125

Glu Lys Pro Tyr Lys Cys Pro Glu Cys Gly Lys Ser Phe Ser Arg Ser
    130                 135                 140

Asp Lys Leu Val Arg His Gln Arg Thr His Thr Gly Lys Lys Thr Ser
145                 150                 155                 160

Ser Arg Tyr Pro Tyr Asp Val Pro Asp Tyr Ala Ser
                165                 170
```

<210> SEQ ID NO 45
<211> LENGTH: 2049
<212> TYPE: DNA
<213> ORGANISM: Artificial Sequence
<220> FEATURE:
<223> OTHER INFORMATION: synthetic

<400> SEQUENCE: 45
gcaagtgccc caagaaggcg ggccgcccag ccttctgacg ctagccccgc tgcccaggtg     60
gatctgcgaa cgctgggtta ttctcagcag cagcaagaga agattaagcc taaggtccgg    120
agtactgtgg cacagcacca tgaggctctg gtcgggcacg gcttcacgca cgcacacatc    180
gttgcactct cccagcaccc tgccgcgctg ggcacagtgg cagtgaagta ccaagatatg    240
attgcggcac ttcccgaagc tactcacgag gccatcgtcg gcgttgggaa gcagtggtca    300
ggcgctaggg cactggaggc actgctgact gtggccgggg agcttcgcgg accccccctg    360
cagttggaca caggccagct gctgaagata gcaaaacgag gaggcgtcac agctgtagag    420
gccgtgcatg cgtggcgcaa tgcccttacc ggggcccctc tgaatctgac cccgcagcaa    480
gtggtagcca ttgcgtctaa caacggaggg aaacaggcac tcgagacagt tcaacggctg    540
ctccccgtgc tttgccaggc gcacggactg accccagaac aagtggtggc gatcgcctca    600
aataacggcg gcaaacaggc tcttgaaacc gtgcagagac tgctgccagt actgtgccag    660
gctcatggcc tgaccccaga gcaggttgtg gccatcgctt caaacaatgg cggtaaacag    720

```
gcgctcgaga ctgtccagag gctgttgcct gtgctctgcc aagctcatgg cctgacgccc      780
gaacaggtgg ttgccatcgc tagcaacatc ggcggcaagc aagctctcga gacagtgcaa      840
cggctgctgc ccgtactctg ccaggcacat gggctgactc ccgagcaagt ggttgctatt      900
gcatctaaca acggcggaaa gcaggcgctg gagactgtcc agcgtttgct tcctgttttg      960
tgtcaggctc acggcttgac gcccgaacag gtagtggcca tagcctccaa catcggagga     1020
aaacaggcac ttgaaacagt ccagaggctt ctccccgtcc tgtgccaagc ccatggcctc     1080
actccacagc aagtagtggc tattgcatcc aatggaggcg ggaaacaagc cttggaaacc     1140
gtccaggccc tgctgcctgt cctgtgccag gcacacgggc tgacacctga caggtggtc      1200 gcaattgcca gtaatggtgg cgggaagcaa gccctggaga ctgttcaggc tttgctgccc     1260
gttctgtgtc aagcacacgg tctgactcca gaacaggttg tggctatcgc ctccaataat     1320
ggtggcaaac aggctctcga aacagtgcag aggctgctgc ccgtgctgtg tcaagcccat     1380
ggcctgaccc cacagcaggt cgtggccatt gcctctaata atggaggtaa acaggccctg     1440
gagacagtcc agagattgct tccagttctg tgtcaggccc acgggctgac ccctcaacag     1500
gtcgtcgcca tcgcctcaaa caacggtggc aagcaggcac tcgagactgt gcagcggctc     1560
ttgcctgtgc tgtgtcaagc ccatggactg accccgaaac aggtggttgc cattgccagc     1620
aacaacggtg gaaacaggc tttggaaacc gtgcaacgcc tgctgccggt tctgtgccag     1680
gctcacgggc ttaccccgga acaggtggta gctatcgcta gcaataatgg agggaagcag     1740
gccctggaaa cagtgcagag actgctcccc gtcctctgcc aggcacacgg actcaccccg     1800
gagcaagtgg tcgccatagc ctccaacggt ggagggaagc aggcactgga gacagtgcag     1860
agacttctcc cagtgctctg tcaggctcat gggctcaccc ctcaacaggt agtagccata     1920
gctagtaaca atggaggtcg tccagcattg gagagcatcg tggcgcagct gagccgccca     1980
gacccagcgc ttgccgcctt gaccggaagc tatccctacg acgtgcctga ttacgcttaa     2040
taaaagctt                                                             2049
```

<210> SEQ ID NO 46
<211> LENGTH: 689
<212> TYPE: PRT
<213> ORGANISM: Artificial Sequence
<220> FEATURE:
<223> OTHER INFORMATION: synthetic

<400> SEQUENCE: 46

Met Pro Lys Lys Lys Arg Lys Val Thr Ser Ala Ser Ala Pro Arg Arg
1               5                   10                  15

Arg Ala Ala Gln Pro Ser Asp Ala Ser Pro Ala Ala Gln Val Asp Leu
            20                  25                  30

Arg Thr Leu Gly Tyr Ser Gln Gln Gln Gln Glu Lys Ile Lys Pro Lys
        35                  40                  45

Val Arg Ser Thr Val Ala Gln His His Glu Ala Leu Val Gly His Gly
    50                  55                  60

Phe Thr His Ala His Ile Val Ala Leu Ser Gln His Pro Ala Ala Leu
65                  70                  75                  80

Gly Thr Val Ala Val Lys Tyr Gln Asp Met Ile Ala Ala Leu Pro Glu
                85                  90                  95

Ala Thr His Glu Ala Ile Val Gly Val Gly Lys Gln Trp Ser Gly Ala
            100                 105                 110

Arg Ala Leu Glu Ala Leu Leu Thr Val Ala Gly Glu Leu Arg Gly Pro
        115                 120                 125

```
Pro Leu Gln Leu Asp Thr Gly Gln Leu Leu Lys Ile Ala Lys Arg Gly
    130                 135                 140

Gly Val Thr Ala Val Glu Ala Val His Ala Trp Arg Asn Ala Leu Thr
145                 150                 155                 160

Gly Ala Pro Leu Asn Leu Thr Pro Gln Gln Val Val Ala Ile Ala Ser
                165                 170                 175

Asn Asn Gly Gly Lys Gln Ala Leu Glu Thr Val Gln Arg Leu Leu Pro
            180                 185                 190

Val Leu Cys Gln Ala His Gly Leu Thr Pro Glu Gln Val Val Ala Ile
        195                 200                 205

Ala Ser Asn Asn Gly Gly Lys Gln Ala Leu Glu Thr Val Gln Arg Leu
    210                 215                 220

Leu Pro Val Leu Cys Gln Ala His Gly Leu Thr Pro Glu Gln Val Val
225                 230                 235                 240

Ala Ile Ala Ser Asn Asn Gly Gly Lys Gln Ala Leu Glu Thr Val Gln
                245                 250                 255

Arg Leu Leu Pro Val Leu Cys Gln Ala His Gly Leu Thr Pro Glu Gln
            260                 265                 270

Val Val Ala Ile Ala Ser Asn Ile Gly Gly Lys Gln Ala Leu Glu Thr
        275                 280                 285

Val Gln Arg Leu Leu Pro Val Leu Cys Gln Ala His Gly Leu Thr Pro
    290                 295                 300

Glu Gln Val Val Ala Ile Ala Ser Asn Asn Gly Gly Lys Gln Ala Leu
305                 310                 315                 320

Glu Thr Val Gln Arg Leu Leu Pro Val Leu Cys Gln Ala His Gly Leu
                325                 330                 335

Thr Pro Glu Gln Val Val Ala Ile Ala Ser Asn Ile Gly Gly Lys Gln
            340                 345                 350

Ala Leu Glu Thr Val Gln Arg Leu Leu Pro Val Leu Cys Gln Ala His
        355                 360                 365

Gly Leu Thr Pro Gln Gln Val Val Ala Ile Ala Ser Asn Gly Gly Gly
    370                 375                 380

Lys Gln Ala Leu Glu Thr Val Gln Ala Leu Leu Pro Val Leu Cys Gln
385                 390                 395                 400

Ala His Gly Leu Thr Pro Glu Gln Val Val Ala Ile Ala Ser Asn Gly
                405                 410                 415

Gly Gly Lys Gln Ala Leu Glu Thr Val Gln Ala Leu Leu Pro Val Leu
            420                 425                 430

Cys Gln Ala His Gly Leu Thr Pro Glu Gln Val Val Ala Ile Ala Ser
        435                 440                 445

Asn Asn Gly Gly Lys Gln Ala Leu Glu Thr Val Gln Arg Leu Leu Pro
    450                 455                 460

Val Leu Cys Gln Ala His Gly Leu Thr Pro Gln Gln Val Val Ala Ile
465                 470                 475                 480

Ala Ser Asn Asn Gly Gly Lys Gln Ala Leu Glu Thr Val Gln Arg Leu
                485                 490                 495

Leu Pro Val Leu Cys Gln Ala His Gly Leu Thr Pro Gln Gln Val Val
            500                 505                 510

Ala Ile Ala Ser Asn Asn Gly Gly Lys Gln Ala Leu Glu Thr Val Gln
        515                 520                 525

Arg Leu Leu Pro Val Leu Cys Gln Ala His Gly Leu Thr Pro Glu Gln
    530                 535                 540
```

Val Val Ala Ile Ala Ser Asn Asn Gly Gly Lys Gln Ala Leu Glu Thr
545                 550                 555                 560

Val Gln Arg Leu Leu Pro Val Leu Cys Gln Ala His Gly Leu Thr Pro
            565                 570                 575

Glu Gln Val Val Ala Ile Ala Ser Asn Asn Gly Gly Lys Gln Ala Leu
        580                 585                 590

Glu Thr Val Gln Arg Leu Leu Pro Val Leu Cys Gln Ala His Gly Leu
    595                 600                 605

Thr Pro Glu Gln Val Val Ala Ile Ala Ser Asn Gly Gly Gly Lys Gln
610                 615                 620

Ala Leu Glu Thr Val Gln Arg Leu Leu Pro Val Leu Cys Gln Ala His
625                 630                 635                 640

Gly Leu Thr Pro Gln Gln Val Val Ala Ile Ala Ser Asn Asn Gly Gly
            645                 650                 655

Arg Pro Ala Leu Glu Ser Ile Val Ala Gln Leu Ser Arg Pro Asp Pro
        660                 665                 670

Ala Leu Ala Ala Leu Thr Gly Ser Tyr Pro Tyr Asp Val Pro Asp Tyr
    675                 680                 685

Ala

<210> SEQ ID NO 47
<211> LENGTH: 2315
<212> TYPE: DNA
<213> ORGANISM: Artificial Sequence
<220> FEATURE:
<223> OTHER INFORMATION: synthetic

<400> SEQUENCE: 47
ctagcgcccc cagaagaagg gccgctcagc cttccgatgc ctctcctgcc gcccaggtgg     60
acctgagaac cctgggctac agccagcagc agcaggaaaa gatcaagccc aaagtgcgga    120
gcaccgtggc ccagcaccac gaagccctcg tgggccacgg cttacccac gctcacatcg     180 tggccctgag ccagcatcct gccgctctgg gaaccgtggc cgtgaagtac caggacatga    240
tcgccgccct gcccgaggcc acacacgagg ctatcgtggg cgtgggcaag cagtggtccg    300
gcgctagagc actcgaggcc ttgctgacag tggccgcga gctgagaggc cctccactgc    360
agctggacac cggccagctg ctgaagatcg ccaagcgggg aggcgtgaca gccgtggaag    420
ccgtgcacgc ttggcggaat gccctgacag gcgctcccct gaaccttacg ccgcagcagg    480
tggtggccat cgccagccac gatggcggca agcaggcgct ggagacggtg cagcggctgc    540
ttccggtgct gtgccaggcc catggcctga ccccggagca ggtggtggcc atcgccagca    600
atattggtgg caagcaggcg ctggagacgg tgcagcgatt gttgccggtg ctgtgccagg    660
cccatggcct gaccccggag caggtggtgg ccatcgccag ccacgacggt ggcaagcagg    720
cgctggagac tgtccagcgg ctgttgccgg tgctgtgcca ggcccatggc ctgaccccgg    780
agcaggtggt ggccatcgcc agcaatggcg gtggcaagca ggcgcttgag acggtgcagc    840
ggctgttgcc ggtgctgtgc caggcccatg gcctgacccc ggagcaggtg gtggccatcg    900
ccagcaatgg cggtgcaag caggctctgg agacggtgca gcggctgttg ccggtgctgt    960
gccaggccca tggcctgacc ccggagcagg tggtggccat cgccagcaat ggcggggca    1020 agcaggcgct ggagacggtg cagcggctgt tgccggtgct gtgccaggcc catggcctga    1080
ccccgcagca ggtggtggcc atcgccagca atattggcgg caagcaggcg ctggagacgg    1140
tgcaggcgct gttgccggtg ctgtgccagg cccatggcct gaccccggag caggtggtgg    1200

```
ccatcgcaag caatggcggt ggcaagcagg cgctggagac ggtgcaggcg ctgttgccgg      1260
tgctgtgcca ggcccatggc ctgaccccgg agcaggtggt ggcaatcgcc agcaatattg      1320
gtggcaagca ggcgctggag acggtgcagc ggctgttgcc ggtgctgtgc caggcccatg      1380
gcctgacccc gcaacaggtg gtagccatcg ccagcaatat tggtggcaag caggcgctgg      1440
agacggtgca gcggctgttg ccggtgctgt gccaggccca tggcctgaca ccccagcagg      1500
tggtagcgat cgccagcaat aagggtggca agcaggcgct ggagacggtg cagcggctgc      1560
ttccggtgct gtgccaggcc catggcctga ccccggagca ggtggtggcc atcgccagca      1620
ataagggtgg caagcaggcg ctggagacgt gcagcgatt gttgccggtg ctgtgccagg       1680
cccatggcct gaccccggag caggtggtgg ccatcgccag caataagggt ggcaagcagg      1740
cgctggagac tgtccagcgg ctgttgccgg tgctgtgcca ggcccatggc ctgaccccgg      1800
agcaggtggt ggccatcgcc agcaatggcg gtggcaagca ggcgcttgag acggtgcagc      1860
ggctgttgcc ggtgctgtgc caggcccatg gcctgacccc gcagcaggtg gtggccatcg      1920
ccagccacga cggtggcaag caggctctgg agacggtgca gcggctgttg ccggtgctgt      1980
gccaggccca tggcctgacc ccggagcagg tggtggccat cgccagcaat ggcgggggca      2040
agcaggcgct ggagacggtg cagcggctgt tgccggtgct gtgccaggcc catggcctga      2100
ccccgcagca ggtggtggcc atcgccagca ataagggcgg caagcaggcg ctggagacgg      2160
tgcaggcgct gttgccggtg ctgtgccagg cccatggcct gacacccag caggtcgtgg       2220 ccattgccag caacaaggga ggcagacccg ccctggaatc tattgtggcc cagctgagca      2280
gacccgaccc agctctggcc gccctgacag gatcc                                 2315
```

<210> SEQ ID NO 48
<211> LENGTH: 790
<212> TYPE: PRT
<213> ORGANISM: Artificial Sequence
<220> FEATURE:
<223> OTHER INFORMATION: synthetic

<400> SEQUENCE: 48

```
Met Pro Lys Lys Arg Lys Val Thr Ser Ala Pro Arg Arg Arg Ala
1               5                   10                  15

Ala Gln Pro Ser Asp Ala Ser Pro Ala Ala Gln Val Asp Leu Arg Thr
            20                  25                  30

Leu Gly Tyr Ser Gln Gln Gln Glu Lys Ile Lys Pro Lys Val Arg
        35                  40                  45

Ser Thr Val Ala Gln His His Glu Ala Leu Val Gly His Gly Phe Thr
    50                  55                  60

His Ala His Ile Val Ala Leu Ser Gln His Pro Ala Ala Leu Gly Thr
65                  70                  75                  80

Val Ala Val Lys Tyr Gln Asp Met Ile Ala Ala Leu Pro Glu Ala Thr
                85                  90                  95

His Glu Ala Ile Val Gly Val Gly Lys Gln Trp Ser Gly Ala Arg Ala
            100                 105                 110

Leu Glu Ala Leu Leu Thr Val Ala Gly Glu Leu Arg Gly Pro Pro Leu
        115                 120                 125

Gln Leu Asp Thr Gly Gln Leu Leu Lys Ile Ala Lys Arg Gly Gly Val
    130                 135                 140

Thr Ala Val Glu Ala Val His Ala Trp Arg Asn Ala Leu Thr Gly Ala
145                 150                 155                 160

Pro Leu Asn Leu Thr Pro Gln Gln Val Val Ala Ile Ala Ser His Asp
```

```
                    165                 170                 175
Gly Gly Lys Gln Ala Leu Glu Thr Val Gln Arg Leu Leu Pro Val Leu
                180                 185                 190

Cys Gln Ala His Gly Leu Thr Pro Glu Gln Val Val Ala Ile Ala Ser
                195                 200                 205

Asn Ile Gly Gly Lys Gln Ala Leu Glu Thr Val Gln Arg Leu Leu Pro
    210                 215                 220

Val Leu Cys Gln Ala His Gly Leu Thr Pro Glu Gln Val Val Ala Ile
225                 230                 235                 240

Ala Ser His Asp Gly Gly Lys Gln Ala Leu Glu Thr Val Gln Arg Leu
                    245                 250                 255

Leu Pro Val Leu Cys Gln Ala His Gly Leu Thr Pro Glu Gln Val Val
                260                 265                 270

Ala Ile Ala Ser Asn Gly Gly Lys Gln Ala Leu Glu Thr Val Gln
                275                 280                 285

Arg Leu Leu Pro Val Leu Cys Gln Ala His Gly Leu Thr Pro Glu Gln
290                 295                 300

Val Val Ala Ile Ala Ser Asn Gly Gly Lys Gln Ala Leu Glu Thr
305                 310                 315                 320

Val Gln Arg Leu Leu Pro Val Leu Cys Gln Ala His Gly Leu Thr Pro
                325                 330                 335

Glu Gln Val Val Ala Ile Ala Ser Asn Gly Gly Lys Gln Ala Leu
                340                 345                 350

Glu Thr Val Gln Arg Leu Leu Pro Val Leu Cys Gln Ala His Gly Leu
                355                 360                 365

Thr Pro Gln Gln Val Val Ala Ile Ala Ser Asn Ile Gly Gly Lys Gln
370                 375                 380

Ala Leu Glu Thr Val Gln Ala Leu Leu Pro Val Leu Cys Gln Ala His
385                 390                 395                 400

Gly Leu Thr Pro Glu Gln Val Val Ala Ile Ala Ser Asn Gly Gly Gly
                405                 410                 415

Lys Gln Ala Leu Glu Thr Val Gln Ala Leu Leu Pro Val Leu Cys Gln
                420                 425                 430

Ala His Gly Leu Thr Pro Glu Gln Val Val Ala Ile Ala Ser Asn Ile
                435                 440                 445

Gly Gly Lys Gln Ala Leu Glu Thr Val Gln Arg Leu Leu Pro Val Leu
                450                 455                 460

Cys Gln Ala His Gly Leu Thr Pro Glu Gln Val Val Ala Ile Ala Ser
465                 470                 475                 480

Asn Ile Gly Gly Lys Gln Ala Leu Glu Thr Val Gln Arg Leu Leu Pro
                485                 490                 495

Val Leu Cys Gln Ala His Gly Leu Thr Pro Gln Gln Val Val Ala Ile
                500                 505                 510

Ala Ser Asn Lys Gly Gly Lys Gln Ala Leu Glu Thr Val Gln Arg Leu
                515                 520                 525

Leu Pro Val Leu Cys Gln Ala His Gly Leu Thr Pro Glu Gln Val Val
                530                 535                 540

Ala Ile Ala Ser Asn Lys Gly Gly Lys Gln Ala Leu Glu Thr Val Gln
545                 550                 555                 560

Arg Leu Leu Pro Val Leu Cys Gln Ala His Gly Leu Thr Pro Glu Gln
                565                 570                 575

Val Val Ala Ile Ala Ser Asn Lys Gly Gly Lys Gln Ala Leu Glu Thr
                580                 585                 590
```

Val Gln Arg Leu Leu Pro Val Leu Cys Gln Ala His Gly Leu Thr Pro
            595                 600                 605

Glu Gln Val Val Ala Ile Ala Ser Asn Gly Gly Lys Gln Ala Leu
    610                 615                 620

Glu Thr Val Gln Arg Leu Leu Pro Val Leu Cys Gln Ala His Gly Leu
625                 630                 635                 640

Thr Pro Gln Gln Val Val Ala Ile Ala Ser His Asp Gly Gly Lys Gln
                645                 650                 655

Ala Leu Glu Thr Val Gln Arg Leu Leu Pro Val Leu Cys Gln Ala His
            660                 665                 670

Gly Leu Thr Pro Glu Gln Val Val Ala Ile Ala Ser Asn Gly Gly Gly
        675                 680                 685

Lys Gln Ala Leu Glu Thr Val Gln Arg Leu Leu Pro Val Leu Cys Gln
    690                 695                 700

Ala His Gly Leu Thr Pro Gln Gln Val Val Ala Ile Ala Ser Asn Lys
705                 710                 715                 720

Gly Gly Lys Gln Ala Leu Glu Thr Val Gln Ala Leu Leu Pro Val Leu
                725                 730                 735

Cys Gln Ala His Gly Leu Thr Pro Gln Gln Val Val Ala Ile Ala Ser
            740                 745                 750

Asn Lys Gly Gly Arg Pro Ala Leu Glu Ser Ile Val Ala Gln Leu Ser
        755                 760                 765

Arg Pro Asp Pro Ala Leu Ala Ala Leu Thr Gly Ser Tyr Pro Tyr Asp
    770                 775                 780

Val Pro Asp Tyr Ala Ser
785                 790

<210> SEQ ID NO 49
<211> LENGTH: 1047
<212> TYPE: DNA
<213> ORGANISM: Artificial Sequence
<220> FEATURE:
<223> OTHER INFORMATION: synthetic

<400> SEQUENCE: 49
atgaatggca cagaaggccc taacttctac gtgcccttct ccaatgcgac gggtgtggta      60
cgcagcccct tcgagtaccc acagtactac ctggctgagc catggcagtt ctccatgctg     120
gccgcctaca tgtttctgct gatcgtgctg ggcttcccca tcaacttcct cacgctctac     180
gtcaccgtcc agcacaagaa gctgcgcacg cctctcaact catcctgct caacctagcc      240 gtggctgacc tcttcatggt cctaggtggc ttcaccagca ccctctacac ctctctgcat     300
ggatacttcg tcttcgggcc cacaggatgc aatttggagg cttctttgc caccctgggc      360 ggtgaaattg ccctgtggtc cttggtggtc ctggccatcg agcggtacgt ggtggtgtgt     420
aagcccatga gcaacttccg cttcggggag aaccatgcca tcatgggcgt tgccttcacc      480
tgggtcatgg cgctggcctg cgccgcaccc ccactcgccg gctggtccag gtacatcccc     540
gagggcctgc agtgctcgtg tggaatcgac tactacacgc tcaagccgga ggtcaacaac      600 gagtctttg tcatctacat gttcgtggtc cacttcacca tccccatgat tatcatcttt     660
ttctgctatg gcagctcgt cttcaccgtc aaggaggccg ctgcccagca gcaggagtca     720
gccaccacac agaaggcaga gaaggaggtc acccgcatgg tcatcatcat ggtcatcgct      780
ttcctgatct gctgggtgcc ctacgccagc gtggcattct acatcttcac ccaccagggc     840
tccaacttcg gtcccatctt catgaccatc ccagcgttct tgccaagag cgccgccatc      900

```
tacaaccctg tcatctatat catgatgaac aagcagttcc ggaactgcat gctcaccacc    960
atctgctgcg gcaagaaccc actgggtgac gatgaggcct ctgctaccgt gtccaagacg   1020
gagacgagcc aggtggcccc ggcctaa                                       1047
```

<210> SEQ ID NO 50
<211> LENGTH: 288
<212> TYPE: DNA
<213> ORGANISM: Artificial Sequence
<220> FEATURE:
<223> OTHER INFORMATION: synthetic

<400> SEQUENCE: 50

```
gatgctaaat cactcactgc atggtcccgt actctggtta cttttaaaga tgtgttcgtg     60
gatttcactc gtgaagaatg gaaactgctg gacaccgcac agcaaattct gtatcgtaac    120
gttatgctgg agaactataa aaacctcgtc tcactgggtt accagctgac caagcctgat    180
gtaatcctgc gcctggaaaa aggtgaagaa ccgtggctgg tcgaacgcga gatccaccaa    240
gaaacccacc cggactcaga accgcattc gagatcaaaa gctccgtc                 288
```

<210> SEQ ID NO 51
<211> LENGTH: 891
<212> TYPE: DNA
<213> ORGANISM: Artificial Sequence
<220> FEATURE:
<223> OTHER INFORMATION: synthetic

<400> SEQUENCE: 51

```
cagatcttcc ccacctagcc acctggcaaa ctgctccttc tctcaaaggc ccaaacatgg     60
cctcccagac tgcaaccccc aggcagtcag gccctgtctc cacaacctca cagccaccct    120
ggacggaatc tgcttcttcc cacatttgag tcctcctcag cccctgagct cctctgggca    180
gggctgtttc tttccatctt tgtattccca ggggcctgca ataaatgtt taatgaacga    240 acaagagagt gaattccaat tccatgcaac aaggattggg ctcctgggcc ctaggctatg    300
tgtctggcac cagaaacgga agctgcaggt tgcagcccct gccctcatgg agctcctcct    360
gtcagaggag tgtggggact ggatgactcc agaggtaact tgtggggaa cgaacaggta    420 agggggctgtg tgacgagatg agagactggg agaataaacc agaaagtctc tagctgtcca    480
gaggacatag cacagaggcc catggtccct atttcaaacc caggccacca gactgagctg    540
ggaccttggg acagacaagt catgcagaag ttaggggacc ttctcctccc ttttcctgga    600
tcctgagtac ctctcctccc tgacctcagg cttcctccta gtgtcacctt ggcccctctt    660
agaagccaat taggccctca gtttctgcag cggggattaa tatgattatg aacaccccca    720
atctcccaga tgctgattca gccaggagct taggaggggg aggtcacttt ataagggtct    780
gggggggtca gaacccagag tcatccagct ggagccctga gtggctgagc tcaggccttc    840
gcagcattct tgggtgggag cagccacggg tcagccacaa gggccacagc c            891
```

<210> SEQ ID NO 52
<211> LENGTH: 662
<212> TYPE: DNA
<213> ORGANISM: Artificial Sequence
<220> FEATURE:
<223> OTHER INFORMATION: synthetic

<400> SEQUENCE: 52

```
tccctgcagg tcataaaatc ccagtccaga gtcaccagcc cttcttaacc acttcctact     60
```

-continued

```
gtgtgaccct tcagccttt acttcctcat cagtaaaatg aggctgatga tatgggcatc    120
catactccag ggccagtgtg agcttacaac aagataagga gtggtgctga gcctggtgcc    180
gggcaggcag caggcatgtt tctcccaatt atgccctctc actgccagcc ccacctccat    240
tgtcctcacc cccagggctc aaggttctgc cttcccttt ctcagccctg accctactga    300
acatgtctcc ccactcccag gcagtgccag ggcctctcct ggagggttgc ggggacagaa    360
ggacagccgg agtgcagagt cagcggttga gggattgggg ctatgccagc taatccgaag    420
ggttgggggg gctgagctgg attcacctgt ccttgtctct gattggctct tggacacccc    480 tagccccaa  atcccactaa gcagcccac  cagggattgc acaggtccgt agagagccag    540
ttgattgcag gtcctcctgg ggccagaagg gtgcctggga ggccaggttc tggggatccc    600
ctccatccag aagaaccacc tgctcactct gtcccttcgc ctgctgctgg accgcggcc    660 gc                                                                  662
```

<210> SEQ ID NO 53
<211> LENGTH: 20
<212> TYPE: DNA
<213> ORGANISM: Artificial Sequence
<220> FEATURE:
<223> OTHER INFORMATION: synthetic

<400> SEQUENCE: 53
acgtaaacgg ccacaagttc                                               20

<210> SEQ ID NO 54
<211> LENGTH: 20
<212> TYPE: DNA
<213> ORGANISM: Artificial Sequence
<220> FEATURE:
<223> OTHER INFORMATION: synthetic

<400> SEQUENCE: 54
aagtcgtgct gcttcatgtg                                               20

<210> SEQ ID NO 55
<211> LENGTH: 21
<212> TYPE: DNA
<213> ORGANISM: Artificial Sequence
<220> FEATURE:
<223> OTHER INFORMATION: synthetic

<400> SEQUENCE: 55
caagatcatt gctcctcctg a                                             21

<210> SEQ ID NO 56
<211> LENGTH: 21
<212> TYPE: DNA
<213> ORGANISM: Artificial Sequence
<220> FEATURE:
<223> OTHER INFORMATION: synthetic

<400> SEQUENCE: 56
catcgtactc ctgcttgctg a                                             21

<210> SEQ ID NO 57
<211> LENGTH: 19
<212> TYPE: DNA
<213> ORGANISM: Artificial Sequence
<220> FEATURE:
<223> OTHER INFORMATION: synthetic

<400> SEQUENCE: 57

```
gtcggtgtga acggatttg                                                    19

<210> SEQ ID NO 58
<211> LENGTH: 20
<212> TYPE: DNA
<213> ORGANISM: Artificial Sequence
<220> FEATURE:
<223> OTHER INFORMATION: synthetic

<400> SEQUENCE: 58
caatgaaggg gtcgttgatg                                                   20
```